United States Patent
Badawi et al.

(10) Patent No.: US 8,529,622 B2
(45) Date of Patent: Sep. 10, 2013

(54) INTRAOCULAR IMPLANTS AND RELATED KITS AND METHODS

(75) Inventors: David Y. Badawi, Northbrook, IL (US); Paul Badawi, San Francisco, CA (US)

(73) Assignee: Sight Sciences, Inc., San Francisco, CA (US)

( * ) Notice: Subject to any disclaimer, the term of this patent is extended or adjusted under 35 U.S.C. 154(b) by 0 days.

(21) Appl. No.: 13/020,706

(22) Filed: Feb. 3, 2011

(65) Prior Publication Data

US 2011/0196487 A1    Aug. 11, 2011

Related U.S. Application Data

(60) Provisional application No. 61/301,874, filed on Feb. 5, 2010.

(51) Int. Cl.
*A61F 2/14* (2006.01)
(52) U.S. Cl.
USPC ............. 623/4.1; 623/1.22; 623/23.69; 604/8
(58) Field of Classification Search
USPC .................................... 604/8; 623/4.1, 23.69
See application file for complete search history.

(56) References Cited

U.S. PATENT DOCUMENTS

| | | | |
|---|---|---|---|
| 3,159,161 A | 12/1964 | Ness | |
| 4,068,664 A | 1/1978 | Sharp et al. | |
| 4,457,757 A | 7/1984 | Molteno | |
| 4,553,545 A * | 11/1985 | Maass et al. | 606/198 |
| 4,936,825 A | 6/1990 | Ungerleider | |
| 4,957,505 A | 9/1990 | McDonald | |
| 5,486,165 A | 1/1996 | Stegmann | |
| 5,569,197 A | 10/1996 | Helmus et al. | |
| 5,626,558 A | 5/1997 | Suson | |
| 5,639,278 A | 6/1997 | Dereume et al. | |
| 5,868,697 A | 2/1999 | Richter et al. | |
| 6,050,970 A | 4/2000 | Baerveldt | |
| 6,375,642 B1 | 4/2002 | Grieshaber et al. | |

(Continued)

FOREIGN PATENT DOCUMENTS

| | | |
|---|---|---|
| JP | 2002-541976 A | 12/2002 |
| JP | 2005-510317 A | 4/2005 |

(Continued)

OTHER PUBLICATIONS

Boyle, E.L. (Feb. 1, 2006). "New Glaucoma Devices Take Different Approaches to IOP Lowering," *Ocular Surgery News U.S. Edition*, located at <http://www.osnsupersite.com/view.aspx?rid=12436>, last visited on Apr. 23, 2012, 4 pages.

(Continued)

*Primary Examiner* — William H Matthews
(74) *Attorney, Agent, or Firm* — Morrison & Foerster LLP

(57) ABSTRACT

Devices, methods and kits are described for reducing intraocular pressure. The devices include a support that is implantable within Schlemm's canal and that may restore or maintain at least partial patency of the canal without substantially interfering with transmural or transluminal fluid flow across the canal. The devices utilize the natural drainage process of the eye and may be implanted with minimal trauma to the eye. Kits may include a support and an introducer for implanting the support within Schlemm's canal. Methods may include implanting a support within Schlemm's canal, where the support is capable of restoring or maintaining at least partial patency of the canal without substantial interference with transmural or transluminal fluid flow across the canal.

10 Claims, 43 Drawing Sheets

(56) References Cited

U.S. PATENT DOCUMENTS

| | | | |
|---|---|---|---|
| 6,494,857 | B1 | 12/2002 | Neuhann |
| 6,508,779 | B1 | 1/2003 | Suson |
| 6,616,996 | B1 | 9/2003 | Keith et al. |
| 7,207,980 | B2 | 4/2007 | Christian et al. |
| 7,909,789 | B2 | 3/2011 | Badawi et al. |
| 7,951,155 | B2 | 5/2011 | Smedley et al. |
| 7,967,772 | B2 | 6/2011 | McKenzie et al. |
| 8,075,511 | B2 | 12/2011 | Tu et al. |
| 8,287,482 | B2 | 10/2012 | Badawi et al. |
| 2002/0013546 | A1 | 1/2002 | Grieshaber et al. |
| 2002/0133168 | A1 | 9/2002 | Smedley et al. |
| 2004/0193262 | A1 | 9/2004 | Shadduck |
| 2004/0254521 | A1 | 12/2004 | Simon |
| 2004/0260228 | A1 | 12/2004 | Lynch et al. |
| 2005/0267555 | A1 | 12/2005 | Marnfeldt et al. |
| 2006/0069340 | A1 | 3/2006 | Simon |
| 2006/0195187 | A1 | 8/2006 | Stegman et al. |
| 2007/0298068 | A1 | 12/2007 | Badawi et al. |
| 2009/0132040 | A1 | 5/2009 | Frion et al. |
| 2009/0227934 | A1 | 9/2009 | Euteneuer et al. |
| 2010/0191329 | A1 | 7/2010 | Badawi et al. |
| 2011/0098809 | A1 | 4/2011 | Wardle et al. |
| 2011/0130831 | A1 | 6/2011 | Badawi et al. |
| 2012/0059461 | A1 | 3/2012 | Badawi et al. |
| 2012/0197176 | A1 | 8/2012 | Badawi et al. |

FOREIGN PATENT DOCUMENTS

| | | | |
|---|---|---|---|
| JP | 2005-538809 | A | 12/2005 |
| WO | WO-00/64393 | A1 | 11/2000 |
| WO | WO-03/045582 | A1 | 6/2003 |
| WO | WO-2004/026361 | A1 | 4/2004 |
| WO | WO-2005/105197 | A2 | 11/2005 |
| WO | WO-2005/105197 | A3 | 11/2005 |
| WO | WO-2005/107664 | A2 | 11/2005 |
| WO | WO-2005/107664 | A3 | 11/2005 |
| WO | WO-2005/117752 | A1 | 12/2005 |
| WO | WO-2006/066103 | A2 | 6/2006 |
| WO | WO-2006/066103 | A3 | 6/2006 |
| WO | WO-2008/002377 | A1 | 1/2008 |
| WO | WO-2011/097408 | A1 | 8/2011 |

OTHER PUBLICATIONS

Final Office Action mailed on Nov. 1, 2010, for U.S. Appl. No. 11/475,523, filed Jun. 26, 2006, 12 pages.
International Search Report mailed on Nov. 30, 2007, for PCT Application No. PCT/US2007/013038, filed on May 31, 2007, five pages.
International Search Report mailed on Apr. 5, 2011, for PCT Application No. PCT/US2011/023643, filed on Feb. 3, 2011, 2 pages.
Non-Final Office Action mailed on May 17, 2010, for U.S. Appl. No. 11/475,523, filed Jun. 26, 2006, 10 pages.
Non-Final Office Action mailed on Jan. 26, 2012, for U.S. Appl. No. 12/695,053, filed Jan. 27, 2010, 10 pages.
Non-Final Office Action mailed on Mar. 15, 2012, for U.S. Appl. No. 13/245,811, filed Sep. 26, 2011, 4 pages.
Restriction Requirement mailed on Sep. 30, 2009, for U.S. Appl. No. 11/475,523, filed Jun. 26, 2006, 9 pages.
Restriction Requirement mailed on Feb. 23, 2010, for U.S. Appl. No. 11/475,523, filed Jun. 26, 2006, 6 pages.
Written Opinion mailed on Nov. 30, 2007, for PCT Application No. PCT/US2007/013038, filed on May 31, 2007, 6 pages.
Written Opinion mailed on Apr. 5, 2011, for PCT Application No. PCT/US2011/023643, filed on Feb. 3, 2011, 5 pages.
Final Office Action mailed on Jul. 19, 2012, for U.S. Appl. No. 13/245,811, filed Sep. 26, 2011, 6 pages.
Notice of Allowance mailed on Feb. 2, 2011, for U.S. Appl. No. 11/475,523, filed Jun. 26, 2006, 6 pages.
Notice of Allowance mailed on Jun. 11, 2012, for U.S. Appl. No. 12/695,053, filed Jan. 27, 2010, 7 pages.
Non-Final Office Action mailed on Nov. 9, 2012, for U.S. Appl. No. 13/245,811, filed Sep. 26, 2011, 5 pages.
Notice of Allowance mailed on Apr. 2, 2013, for U.S. Appl. No. 13/245,811, filed Sep. 26, 2011, 6 pages.

* cited by examiner

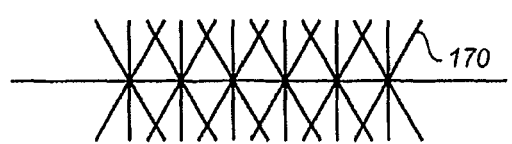
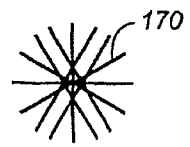
FIG. 8A  FIG. 8B
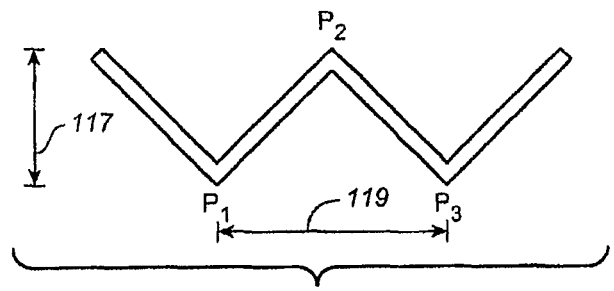
FIG. 8C  FIG. 8D
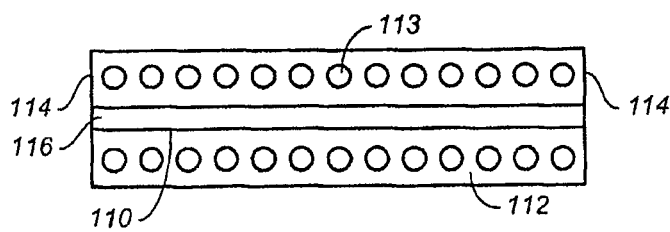
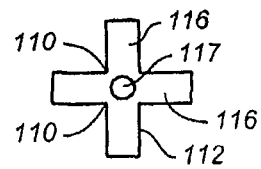
FIG. 8E  FIG. 8F
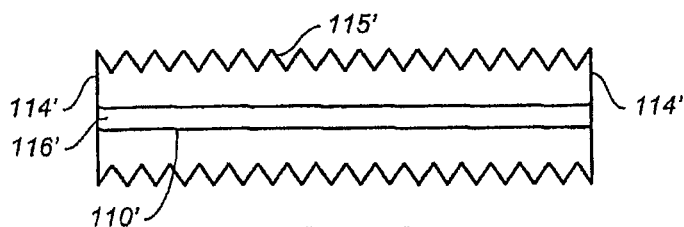
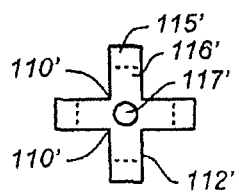
FIG. 8G  FIG. 8H

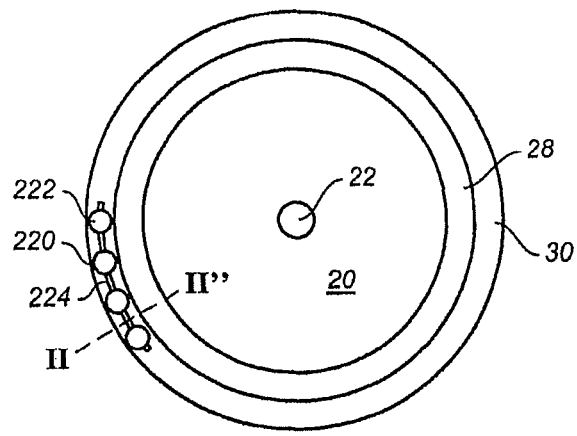 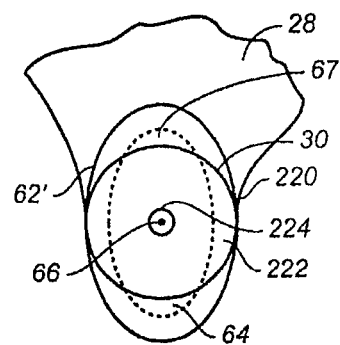
FIG. 12A     FIG. 12B
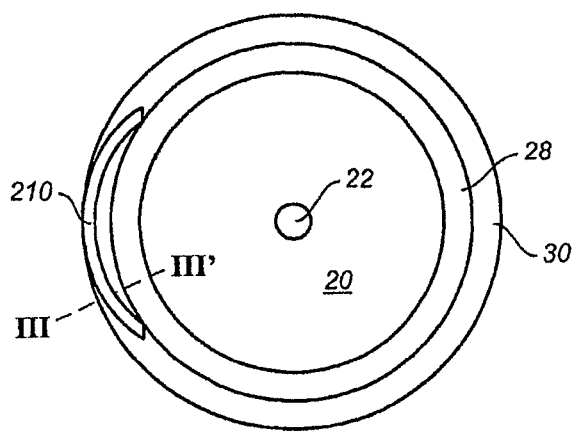 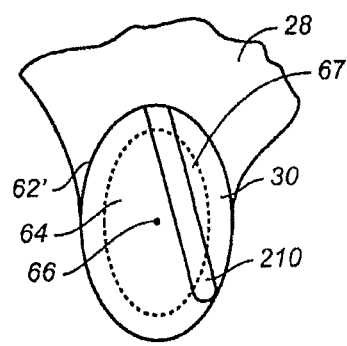
FIG. 12C     FIG. 12D

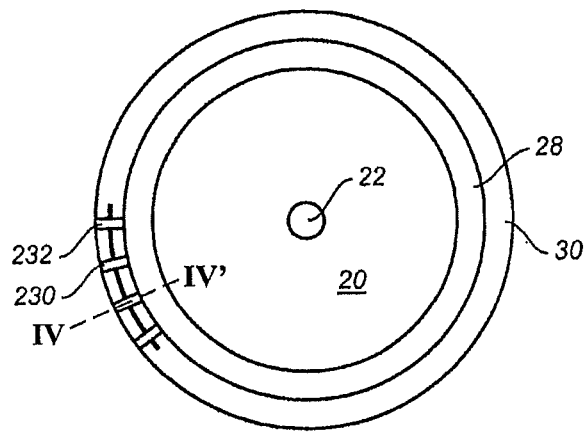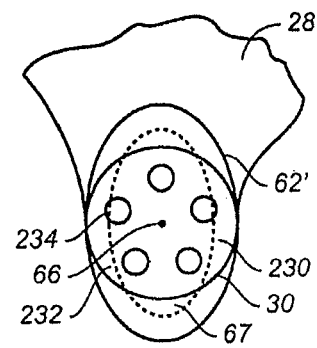
FIG. 12E  FIG. 12F
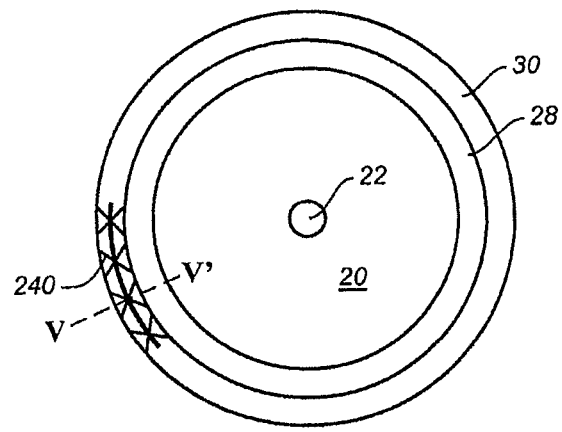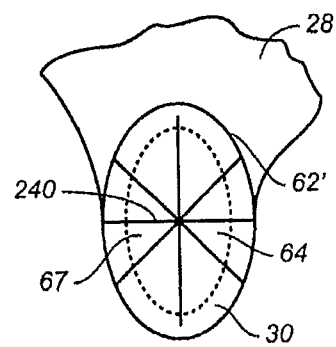
FIG. 12G  FIG. 12H

INTRAOCULAR IMPLANTS AND RELATED KITS AND METHODS

CROSS-REFERENCE TO RELATED APPLICATIONS

This application claims the benefit of U.S. Provisional Application No. 61/301,874, filed on Feb. 5, 2010, the disclosure of which is incorporated herein by reference in its entirety.

FIELD

The devices, kits and methods described herein relate generally to intraocular pressure reduction. More particularly, the devices, kits and methods relate to intraocular implants implantable into Schlemm's canal that can reduce intraocular pressure without substantially interfering with fluid flow across or within Schlemm's canal, such as transluminal fluid flow, transmural fluid flow, and longitudinal fluid flow.

BACKGROUND

Glaucoma is a potentially blinding disease that affects millions of people worldwide. Typically, glaucoma is characterized by elevated intraocular pressure. Increased pressure in the eye can cause damage to the optic nerve which can lead to permanent vision loss if left untreated. Consistent reduction of intraocular pressure can slow down or stop the progressive loss of vision associated with glaucoma. In addition, patients are often diagnosed with pre-glaucoma and ocular hypertension when they exhibit symptoms likely to lead to glaucoma, such as somewhat elevated intraocular pressure, but do not yet show indications of optic nerve damage. Treatments for glaucoma, pre-glaucoma and ocular hypertension primarily seek to reduce intraocular pressure.

Increased intraocular pressure is caused by sub-optimal efflux or drainage of fluid (aqueous humor) from the eye. Aqueous humor or fluid is a clear, colorless fluid that is continuously replenished in the eye. Aqueous humor is produced by the ciliary body, and then flows out primarily through the eye's trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Schlemm's canal is the eye's primary drainage vessel. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Aqueous humor flow out of the eye can be restricted by blockages or constriction in the trabecular meshwork and/or Schlemm's canal. When such flow is blocked, increased ocular pressure may result. Increased intraocular pressure can lead to the collapse of Schlemm's canal. This, in turn, may result in a dramatic further increase in intraocular pressure and, ultimately, the onset of glaucoma.

Glaucoma, pre-glaucoma and ocular hypertension currently can be treated by reducing intraocular pressure using one or more modalities, including medication, incisional surgery, laser surgery, cryosurgery, and other forms of surgery. In the United States, medications or medical therapy are typically the first lines of therapy. If medical therapy is not sufficiently effective, more invasive surgical treatments may be used. In other countries, such as those with socialized medical systems or with nationalized health care systems, surgery may be the first line of therapy if it is considered a more cost effective treatment.

A standard incisional surgical procedure to reduce intraocular pressure is trabeculectomy, or filtration surgery. This procedure involves creating a new drainage site for aqueous humor. Instead of naturally draining through the trabecular meshwork, a new drainage pathway is created by removing a portion of sclera and trabecular meshwork at the drainage angle. This creates an opening or passage between the anterior chamber and the subconjunctival space that is drained by conjunctival blood vessels and lymphatics. The new opening may be covered with sclera and/or conjuctiva to create a new reservoir called a bleb into which aqueous humor can drain. However, trabeculectomy carries both long and short term risks. These risks include blockage of the surgically-created opening through scarring or other mechanisms, hypotony or abnormally low intraocular pressure, expulsive hemorrhage, hyphema, intraocular infection or endophthalmitis, shallow anterior chamber angle, and others.

Bypass stents are also used to bridge a blocked trabecular meshwork. Stents can be inserted between the anterior chamber of the eye and Schlemm's canal, bypassing the trabecular meshwork. However, it is difficult to consistently and reliably implant a bypass stent from the anterior chamber into Schlemm's canal. The implant procedure is challenging and stents can become clogged and lose functionality over time. Others have inserted tubular elongated cylindrical hollow stents longitudinally into Schlemm's canal. Cylindrical hollow stents can be configured to allow circumferential fluid flow around the canal. These too can lose functionality over time as a result of occlusion or scarring.

Schlemm's canal is small (e.g., approximately 100 microns to 300 microns in cross-sectional diameter) and circular. Therefore, it can be difficult or expensive to design and manufacture hollow tubular stents of appropriate dimensions for use in opening Schlemm's canal. In addition, hollow tubular stents can be prone to failure and collapse or occlusion over time, as has been shown for cardiovascular stents. Hollow tubular stents incorporating thin walls are especially prone to failure. Further, the walls of tubular stents placed lengthwise along Schlemm's canal can have significant surface area contact with the trabecular meshwork and/or the collector channels, which can result in blockage of the meshwork or collector channels, substantially interfering with transmural flow across the walls of Schlemm's canal and into the eye's collector channels, and with transluminal flow across the lumen of Schlemm's canal, thereby preventing restoration of normal eye drainage.

In view of the above, easily manufacturable, minimally invasive devices for effective, long-term reduction in intraocular pressure are desirable. In addition, methods and kits incorporating such devices are desirable.

SUMMARY

Described here are devices, kits and methods for reducing intraocular pressure. The devices for reducing pressure within the eye comprise a support implantable circumferentially within at least a portion of Schlemm's canal, where the support is configured to restore or maintain at least partial patency of at least a portion of the canal. The support may have minimal surface area contact with the interior surface of the canal. This may, for example, allow the support to restore or maintain at least partial patency of the canal without substantially interfering with transmural or transluminal flow across the canal. The support may allow for good aqueous humor flow across the trabecular meshwork, across Schlemm's canal, and into the collector channels. The support may avoid substantial interference with aqueous humor flow by minimizing contact with, or obstruction of, the inner lumen of Schlemm's canal, and thereby allowing maximum transmural outflow of aqueous humor. The support may thereby utilize and restore the eye's natural drainage pathways.

The support may be capable of implantation into Schlemm's canal with minimal trauma to the eye and in a minimally invasive procedure. Additionally, the support may be relatively easily implanted into the eye, whether by glaucoma specialists or general ophthalmologists, for example. In some variations, the support may occupy at least a portion of a central core of Schlemm's canal. In certain variations, the support may completely traverse the central core of Schlemm's canal.

The support may contact at least one wall portion (e.g., two wall portions) of Schlemm's canal. As an example, the support may contact first and second interior wall portions of Schlemm's canal, where the first interior wall portion is coincident with an outer peripheral boundary of the trabecular meshwork, and the second interior wall portion has collector channels extending therefrom. In some variations, the support may have minimal surface area contact with the interior surface of Schlemm's canal by only tangentially touching the interior surface, and may position the majority of its mass in the central core of Schlemm's canal.

The support may comprise one or more biocompatible materials. As an example, at least a portion of the support may comprise one or more biocompatible polymers. Non-limiting examples of polymers which may be appropriate include acrylics, silicones, polymethylmethacrylate, polypropylene, and hydrogels. In addition, at least part of the support (e.g., all of the support) may comprise one or more biocompatible metals, such as gold or titanium, and/or one or more biocompatible metal alloys, such as stainless steel or nickel-titanium alloys (e.g., Nitinol). In some variations, at least a portion of the support may comprise one or more shape-memory materials. Suitable shape-memory materials include, but are not limited to, shape-memory polymers or shape-memory alloys, such as nickel-titanium alloys (e.g., Nitinol). In certain variations (e.g., certain variations in which a shape-memory material is used), the support may have a compressed state prior to and during implantation into Schlemm's canal, and an expanded state following implantation (e.g., to open the canal). This may, for example, allow for relatively easy and/or efficient delivery and placement of the support into Schlemm's canal.

In some variations, the support may comprise one or more biocompatible, biodegradable polymers. A biodegradable polymer may be, for example, collagen, a collagen derivative, a poly(lactide); a poly(glycolide); a poly(lactide-co-glycolide); a poly(lactic acid); a poly(glycolic acid); a poly(lactic acid-co-glycolic acid); a poly(lactide)/poly(ethylene glycol) copolymer; a poly(glycolide)/poly(ethylene glycol) copolymer; a poly(lactide-co-glycolide)/poly(ethylene glycol) copolymer; a poly(lactic acid)/poly(ethylene glycol) copolymer; a poly(glycolic acid)/poly(ethylene glycol) copolymer; a poly(lactic acid-co-glycolic acid)/poly(ethylene glycol) copolymer; a poly(caprolactone); a poly(caprolactone)/poly(ethylene glycol) copolymer; a polyorthoester; a poly(phosphazene); a poly(hydroxybutyrate) or a copolymer including a poly(hydroxybutyrate); a poly(lactide-co-caprolactone); a polycarbonate; a poly(esteramide); a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer; or a blend or copolymer thereof.

In certain variations, the support may comprise one or more active agents. For example, a support may be coated or impregnated with an active agent. Alternatively or additionally, an active agent may be dispersed within the support (e.g., by filling a cavity within the support). An active agent may include a prostaglandin, a prostaglandin analog (e.g., latanoprost), a beta blocker, an alpha-2 agonist, a calcium channel blocker, a carbonic anhydrase inhibitor, a growth factor, an anti-metabolite, a chemotherapeutic agent, a steroid, a non-steroidal anti-inflammatory agent, an antagonist of a growth factor, or a combination thereof. The release of an active agent may be controlled using a time-release system (e.g., by embedding and/or encapsulating the active agent within a time-release composition).

In some variations, the support may be solid, while in other variations, at least a portion of the support may be hollow or porous. The surface of the support may be smooth, rough, spiked, and/or fluted, and/or may have one or more other modifications. In certain variations, at least part of the support may comprise a mesh. The support may include at least one fenestration and/or one or more rod-like members in some variations.

In certain variations, the support may comprise at least two adjacent beads and/or other elements. Adjacent beads or other elements may have the same or different sizes and/or shapes, and may comprise the same or different materials. Beads and other elements may be spherical, spheroid, ovoid, cylindrical, cuboid, cubical, conical, discoid, helical, or segments thereof, or may have any other appropriate shape. In some variations, a support may comprise a connector linking at least two adjacent beads and/or other elements together. The connector may be rigid or flexible. Connectors, beads and/or other elements may be coupled (e.g., attached) to each other or may be integral with each other. If there is more than one connector (e.g., two connectors inserted between three beads), the connectors may be of the same or different lengths. The connectors may comprise the same material or materials as the beads they connect, or the connectors and beads may comprise different materials. In certain variations, a connector may function as a spacer configured to provide space between adjacent beads. In some variations, the support may comprise at least two discs separated by, and connected with, a connector. The discs may include fenestrations. The connector may also comprise a guide wire over which a fenestrated bead may be threaded into Schlemm's canal.

In some variations, the support may comprise one or more portions, such as elongated members, which may be straight, curved, twisted, tubular, fenestrated, fluted, porous, etc., and at least some of which may be integral with each other and/or coupled to each other. In some such variations, the portions may have fenestrated fins and/or blunt serrations, and/or may have one or more edges which may be straight, fluted, curvy, arched, or the like. In certain variations, the support may comprise one or more wires which may be straight and/or shaped into various configurations. The surface of a wire in the support may be smooth, or may have one or more modifications.

In certain variations, a device for reducing intraocular pressure may comprise a support implantable circumferentially within at least a portion of Schlemm's canal and configured to restore or maintain at least partial patency of at least a portion of Schlemm's canal, where the support comprises a ribbon member.

In some variations, the ribbon member may comprise at least one fenestration (e.g., multiple fenestrations, such as 2, 3, 4, 5, 10, 15, 20, 21, 22, 23, 24 or 25 fenestrations) and/or may be twisted and/or curved. The ribbon member may comprise a first elongated edge and a second elongated edge, where the first and second elongated edges are configured to contact (e.g., to continuously contact) an interior surface of Schlemm's canal when the device is implanted in Schlemm's canal. The device may not substantially interfere with transmural, transluminal and/or longitudinal flow along, within or across Schlemm's canal, when the device is implanted in Schlemm's canal. The ribbon member may be flat. In certain variations, the support may comprise a shape memory alloy, such as a nickel-titanium alloy (e.g., Nitinol). In some variations, the support may comprise a metal alloy, such as stainless steel or a nickel-titanium alloy (e.g., Nitinol). In certain variations, the support may comprise a metal, such as titanium.

In some variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising at least one fenestration. In certain variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising a plurality of fenestrations. In some variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising a nickel-titanium alloy and a plurality of fenestrations. In certain variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising stainless steel and a plurality of fenestrations. In some variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising titanium and a plurality of fenestrations. In certain variations, a device for reducing intraocular pressure may comprise a support implantable circumferentially within at least a portion of Schlemm's canal and configured to restore or maintain at least partial patency of at least a portion of Schlemm's canal, where the support comprises a twisted and curved ribbon member comprising a plurality of fenestrations. In some variations, a device for reducing intraocular pressure may comprise a support implantable circumferentially within at least a portion of Schlemm's canal and configured to restore or maintain at least partial patency of at least a portion of Schlemm's canal, where the support comprises a twisted and curved ribbon member comprising a nickel-titanium alloy and a plurality of fenestrations.

In certain variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising at least one fenestration, and the device does not substantially interfere with transmural, transluminal and/or longitudinal flow across, within or along Schlemm's canal, when the device is implanted in Schlemm's canal. In some variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising a plurality of fenestrations, and the device does not substantially interfere with transmural, transluminal and/or longitudinal flow across, within or along Schlemm's canal, when the device is implanted in Schlemm's canal. In certain variations, a device for reducing intraocular pressure may comprise a support implantable circumferentially within at least a portion of Schlemm's canal and configured to restore or maintain at least partial patency of at least a portion of Schlemm's canal, where the support comprises a twisted ribbon member comprising a plurality of fenestrations and a nickel-titanium alloy, and the device does not substantially interfere with transmural, transluminal and/or longitudinal flow across, within or along Schlemm's canal, when the device is implanted in Schlemm's canal.

In certain variations, a device for reducing intraocular pressure may comprise a support implantable circumferentially within at least a portion of Schlemm's canal and configured to restore or maintain at least partial patency of at least a portion of Schlemm's canal, where the support has a helical configuration. In some variations, a kit for reducing intraocular pressure may comprise a support implantable circumferentially within at least a portion of Schlemm's canal and configured to restore or maintain at least partial patency of at least a portion of Schlemm's canal, where the support has a helical configuration, and an introducer (e.g., a cannula) for delivering the support. Supports having a helical configuration may, for example, be in the form of a helix or a double helix. In certain variation, the helices of a double helix may have struts or connecters therebetween. In some variations, a kit may further comprise instructions on using the kit. In certain variations, a method for reducing intraocular pressure may comprise inserting a support circumferentially within at least a portion of Schlemm's canal, where the support is configured to restore or maintain at least partial patency of at least a portion of Schlemm's canal, and where the support has a helical configuration. The support may, for example, assume the helical configuration after being inserted within Schlemm's canal (e.g., as a result of the support being heat-formed and/or comprising one or more shape-memory materials).

In certain variations, a device for reducing intraocular pressure may comprise a support implantable circumferentially within at least a portion of Schlemm's canal and configured to restore or maintain at least partial patency of at least a portion of Schlemm's canal, the support comprising a surface (e.g., an outer surface) having a surface area. In some variations, less than about 90% (e.g., less than about 80%, less than about 70%, less than about 60%, less than about 50%, less than about 40%, less than about 30%, less than about 20%, less than about 10%, less than about 5%, less than about 3%, less than about 1%) and/or more than about 0.5% (e.g., more than about 1%, more than about 3%, more than about 5%, more than about 10%, more than about 20%, more than about 30%, more than about 40%, more than about 50%, more than about 60%, more than about 70%, more than about 80%) of the surface area of the surface (e.g., outer surface) of the support may contact the interior surface of Schlemm's canal when the support is in use.

In some variations, a device for reducing intraocular pressure may comprise a support implantable circumferentially within at least a portion of Schlemm's canal and configured to restore or maintain at least partial patency of at least a portion of Schlemm's canal, where the support comprises a first elongated member comprising a first edge and a second elongated member comprising a second edge, the second elongated member coupled to or integral with the first elongated member, and where the first and second edges contact an interior surface of Schlemm's canal when the support is at least partially disposed within Schlemm's canal. In certain variations, the support may further comprise a third elongated member comprising a third edge, and the third elongated member may be coupled to or integral with the first and second elongated members.

The support may extend approximately all the way around Schlemm's canal, if the support has a circumference approximately equal to the circumference of Schlemm's canal. Alternatively, the support may extend around about 95% or less (e.g., about 85% or less, about 75% or less, about 65% or less, about 50% or less, about 25% or less, about 15% or less, about 10% or less, about 5% or less) of the circumference of Schlemm's canal. In some variations, the support may extend from 0° to 360° (e.g., less than 360°, less than 270°, less than 180°, less than 150°, less than 120°, less than 90°, less than 60°, less than 45°, less than 30°, less than 15°) around the canal. For example, the support may extend about 30° to about 180° (e.g., about 50° to about 150°, about 80° to about 120°, about 30° to about 120°, about 100° to about 180°, about 120° to about 180°) around the canal. The support may be configured to contact the inner surface of the walls of Schlemm's canal at one, two, three or more points. In some variations, the support may be attached to tissue. The support may comprise a stiff arcuate member having a radius of curvature smaller or larger than that of Schlemm's canal.

In some variations, the support may be altered using electromagnetic radiation. For example, a laser having a wavelength absorbable by at least one localized portion of the support may be used to alter the support. In certain variations, electromagnetic radiation may be used to release an active agent from the support. In some variations, the support may be visually enhanced using fluorescence or phosphorescence emission. For example, the support may comprise a chromophore that fluoresces or phosphoresces upon excitation with a light source. In some variations, the emitted fluorescence or phosphorescence may be in the wavelength range of about 300 nm to about 800 nm. In certain variations, the support may comprise a chromophore that enhances postoperative monitoring of the support.

Kits for reducing intraocular pressure are also provided. The kits may contain a support that may be implanted circumferentially within Schlemm's canal, and that may be configured to restore or maintain at least partial patency of at least part of Schlemm's canal. When the support is at least partially disposed within the canal, the support may have minimal surface area contact with the interior surface of the canal, while also restoring or maintaining at least partial patency of at least a portion of the canal and not substantially interfering with transmural, transluminal, and/or longitudinal or circumferential flow across or within the canal. In some variations, the support may occupy at least a portion of a central core of Schlemm's canal. The kits may also contain an introducer for implanting the support within the canal. In certain variations, the kits may include a positioning device for adjusting the support within the canal, instructions for use, and/or one or more active agents. Some kits may contain at least two supports. If more than one support is included, the kits may include at least two introducers for delivering the supports. Multiple supports within the same kit may have the same or different shape, size, or composition. Multiple supports within the same kit may be connected together or may remain separate. In some variations, kits may include a fixation device for attaching a support to tissue. In other variations, kits may include a system for visually enhancing the appearance of the support.

In some variations, a kit for reducing intraocular pressure may comprise a first device comprising a first support implantable circumferentially within at least a portion of Schlemm's canal and configured to restore or maintain at least partial patency of at least a portion of Schlemm's canal, the first support comprising a ribbon member, and an introducer configured to deliver the first device into Schlemm's canal. The introducer may comprise a cannula and/or a pushing member. The kit may further comprise a second device comprising a second support implantable circumferentially within at least a portion of Schlemm's canal and configured to restore or maintain at least partial patency of at least a portion of Schlemm's canal. The first and second supports may have different sizes and/or shapes.

In certain variations, a kit for reducing intraocular pressure may comprise a first device comprising a first support implantable circumferentially within at least a portion of Schlemm's canal and configured to restore or maintain at least partial patency of at least a portion of Schlemm's canal, the first support comprising a twisted ribbon member, and an introducer configured to deliver the first device into Schlemm's canal. In some variations, a kit for reducing intraocular pressure may comprise a first device comprising a first support implantable circumferentially within at least a portion of Schlemm's canal and configured to restore or maintain at least partial patency of at least a portion of Schlemm's canal, the first support comprising a twisted ribbon member, and a cannula configured to deliver the first device into Schlemm's canal. In certain variations, a kit for reducing intraocular pressure may comprise a first device comprising a first support implantable circumferentially within at least a portion of Schlemm's canal and configured to restore or maintain at least partial patency of at least a portion of Schlemm's canal, the first support comprising a twisted ribbon member, and a cannula and pushing member configured to deliver the first device into Schlemm's canal. In some variations, a kit for reducing intraocular pressure may comprise a first device comprising a first support and a second device comprising a second support, where the first and second supports each are implantable circumferentially within at least a portion of Schlemm's canal and configured to restore or maintain at least partial patency of at least a portion of Schlemm's canal, the first and second supports each comprising a twisted ribbon member, and an introducer (e.g., a cannula) configured to deliver the first and second devices into Schlemm's canal. The first and second devices may have the same size or may have different sizes. The first and second devices may have the same shape or may have different shapes.

Methods for reducing intraocular pressure are also described. The methods may include inserting a support circumferentially within Schlemm's canal. The support may be configured to restore or maintain at least partial patency of at least part of the canal. The support may or may not occupy at least a portion of a central core of Schlemm's canal, and may not substantially interfere with transmural and/or transluminal flow across the canal, and/or with longitudinal flow within the canal. In some variations, the methods may also include dilating Schlemm's canal prior to insertion of the support. In certain variations, the methods may comprise anchoring the support to tissue. The methods may include implanting at least two supports. If more than one support is implanted within a single eye, the multiple supports may be positioned circumferentially adjacent to each other or circumferentially opposed (i.e., positioned about 180° apart) to each other within Schlemm's canal. Multiple supports within one eye may be connected or may remain separate. In some variations of the methods, the support may be illuminated with a light source to visually enhance the position of the support. In other variations of the methods, the support may be altered using electromagnetic radiation. For example, a laser absorbed by at least one localized portion of the support may be used to alter the support. The alteration may comprise the creation or enlargement of an aperture in the support. If electromagnetic radiation is used to alter a support, the alteration may occur before implantation or after implantation.

In certain variations, a method for reducing intraocular pressure may comprise inserting a first support comprising a ribbon member circumferentially within Schlemm's canal, where the first support maintains the patency of at least a portion of Schlemm's canal and does not substantially interfere with transmural flow across Schlemm's canal.

The method may comprise inserting the first support such that the first support is contained entirely within Schlemm's canal. In some variations, the first support may traverse at least a portion of a central core of Schlemm's canal. For example, the first support may completely traverse the central core of Schlemm's canal. In certain variations, the first support may contact first and second interior wall portions of Schlemm's canal, the first interior wall portion being coincident with an outer peripheral boundary of the trabecular meshwork, and the second interior wall portion having collector channels extending therefrom. The first support may conform to an interior surface of Schlemm's canal.

The first support may have a first configuration prior to being inserted within Schlemm's canal and a second configuration after being inserted into Schlemm's canal, where the first configuration is different from the second configuration. The first support may comprise a shape memory alloy, such as a nickel-titanium alloy (e.g., Nitinol).

The first support may be inserted within Schlemm's canal using an ab interno approach or an ab externo approach. The method may comprise using a cannula to insert the first support within Schlemm's canal.

In some variations, the first support may make only tangential contact with an interior surface of Schlemm's canal when the first support is disposed within Schlemm's canal. In certain variations, the first support may make only point contacts with an interior surface of Schlemm's canal when the first support is disposed within Schlemm's canal. When the first support is disposed within a cylindrical section of Schlemm's canal having an internal wall surface area C, the first support may contact less than 30% of C (e.g., less than 25% of C, less than 20% of C, less than 15% of C, less than 10% of C, less than 5% of C, less than 1% of C). The first support may occupy between about ⅛ and about ½ (e.g., between about ⅛ and about ⅓, between about ¼ and about ½, between about ¼ and about ⅓) of the circumference of Schlemm's canal.

In some variations, the method may further comprise dilating Schlemm's canal prior to insertion of the first support. In certain variations, the method may further comprise inserting a second support circumferentially within Schlemm's canal. Any desired number of supports may be inserted within Schlemm's canal to fill any desired amount of the circumference of the canal, as appropriate. For example, in some cases the first support may occupy between about ¼ and about ½ (e.g., between about ¼ and about ⅓) of the circumference of Schlemm's canal.

In certain variations, one or more supports described here may be delivered into Schlemm's canal while the supports are in one configuration, and then may assume a different configuration once the supports are at least partially disposed within Schlemm's canal. This may, for example, provide for relatively easy and efficient delivery and positioning of the supports within Schlemm's canal. As an example, a relatively straight elongated member (e.g., a wire) formed of one or more shape-memory alloys may be implanted into Schlemm's canal, and may assume a helical configuration once the elongated member is at least partially disposed within Schlemm's canal. Of course, certain variations of supports may maintain the same configuration whether within or outside of Schlemm's canal.

In some variations, supports described herein may restore or maintain at least partial patency (e.g., full patency) of at least a portion of Schlemm's canal such that the canal (or at least a portion thereof) has a diameter of at least about 50 microns (e.g., at least about 75 microns, at least about 100 microns, at least about 125 microns, at least about 150 microns, at least about 175 microns, at least about 200 microns, at least about 225 microns, at least about 250 microns, at least about 275 microns, such as about 300 microns, at least about 350 microns, at least about 400 microns, at least about 450 microns) and/or at most about 500 microns (e.g., at most about 450 microns, at most about 400 microns, at most about 350 microns, at most about 300 microns, at most about 275 microns, at most about 250 microns, at most about 225 microns, at most about 200 microns, at most about 175 microns, at most about 150 microns, at most about 125 microns, at most about 100 microns, at most about 75 microns). In some cases, supports described herein may be used to stretch Schlemm's canal.

In certain variations, a method for reducing intraocular pressure may comprise inserting a first support comprising a ribbon member circumferentially within Schlemm's canal such that the first support is contained entirely within Schlemm's canal, where the first support maintains the patency of at least a portion of Schlemm's canal and does not substantially interfere with transmural flow across Schlemm's canal. In some variations, a method for reducing intraocular pressure may comprise inserting a first support comprising a twisted ribbon member circumferentially within Schlemm's canal, where the first support maintains the patency of at least a portion of Schlemm's canal and does not substantially interfere with transmural flow across Schlemm's canal. In certain variations, a method for reducing intraocular pressure may comprise inserting a first support comprising a twisted ribbon member circumferentially within Schlemm's canal, where the first support traverses at least a portion of a central core of Schlemm's canal, maintains the patency of at least a portion of Schlemm's canal and does not substantially interfere with transmural flow across Schlemm's canal. In some variations, a method for reducing intraocular pressure may comprise inserting a first support comprising a twisted ribbon member circumferentially within Schlemm's canal, where the first support completely traverses a central core of Schlemm's canal, maintains the patency of at least a portion of Schlemm's canal and does not substantially interfere with transmural flow across Schlemm's canal. In certain variations, a method for reducing intraocular pressure may comprise inserting a first support comprising a twisted ribbon member circumferentially within Schlemm's canal, where the first support completely traverses a central core of Schlemm's canal, maintains the patency of at least a portion of Schlemm's canal and does not substantially interfere with transmural flow across Schlemm's canal, and where the first support contacts first and second interior wall portions of Schlemm's canal, the first interior wall portion being coincident with an outer peripheral boundary of the trabecular meshwork, and the second interior wall portion having collector channels extending therefrom. In some variations, a method for reducing intraocular pressure may comprise using a cannula to insert a first support comprising a twisted ribbon member circumferentially within Schlemm's canal, where the first support maintains the patency of at least a portion of Schlemm's canal and does not substantially interfere with transmural flow across Schlemm's canal.

BRIEF DESCRIPTION OF THE DRAWINGS

FIGS. 8A and 8B show side and front views, respectively, of a support having an open network structure; FIGS. 8C and 8D show side and front views, respectively, of a support having a longitudinal zig-zag configuration that may contact the wall of Schlemm's canal at least three points (labeled $P_1$, $P_2$, $P_3$); FIGS. 8E and 8F show side and front views, respectively, of a support having a rod-like member with continuously fluted edges and fenestrations; and FIGS. 8G and 8H show side and front views, respectively, of another variation of a support having a rod-like member with continuously fluted edges.

FIG. 12A illustrates a variation of a support traversing the center of the central core of Schlemm's canal; FIG. 12B shows a cross-sectional view along line II-II'; FIG. 12C illustrates a variation of a support traversing the central core of the canal; FIG. 12D shows a cross-sectional view along line III-III'; FIG. 12E illustrates a variation of a support that occupies the majority of the central core of the canal; FIG. 12F shows a cross-sectional view along line IV-IV'; FIG. 12G illustrates a variation of support having an open network that occupies a portion of the central core of the canal; and FIG. 12H shows a cross-sectional view along line V-V'.

DETAILED DESCRIPTION

Described here are devices, kits and methods to reduce intraocular pressure by restoring or maintaining at least partial patency (e.g., full patency) of Schlemm's canal, so that at least a portion of the canal is patent or unobstructed. The devices, kits and methods operate to keep Schlemm's canal from collapsing while not substantially interfering with the eye's natural drainage mechanism for aqueous humor, in which transmural, transluminal and circumferential or longitudinal fluid flow into, across, around and out of Schlemm's canal occurs. In some variations, the devices may have minimal surface area contact with the interior surface of Schlemm's canal, when the devices are implanted within at least a portion of the canal. The supports may be capable of maximizing patency of the canal while minimizing contact with the porous inner wall of the canal and the collector channel-based outer wall of the canal. The supports may exhibit minimal or no interference with transmural flow (across the inner and outer walls of Schlemm's canal—i.e., into and out of Schlemm's canal), transluminal flow (across Schlemm's canal), and/or circumferential or longitudinal flow (along Schlemm's canal). In some cases, the devices may be implantable in Schlemm's canal with minimal trauma to the eye.

Figure 1:
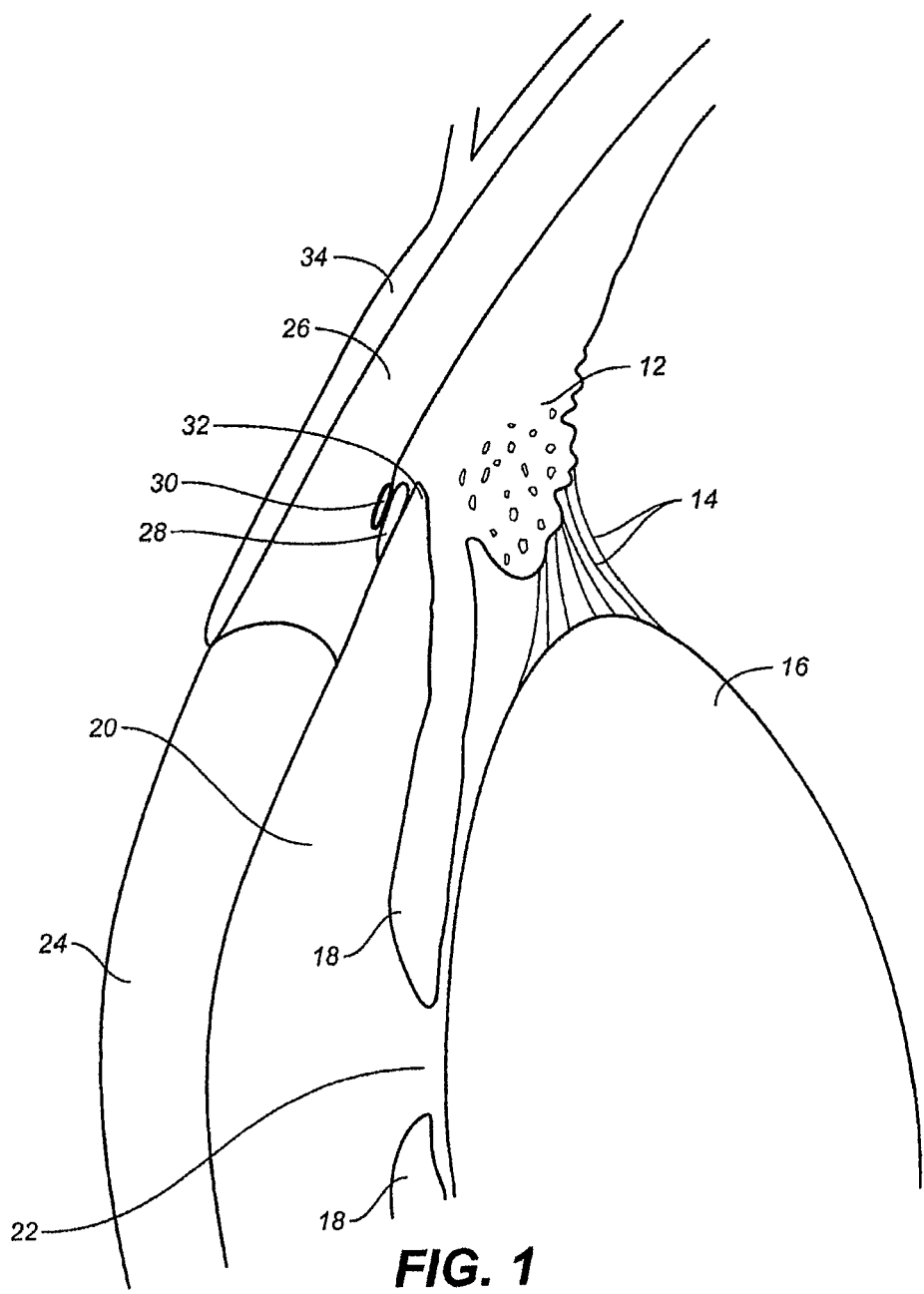
FIG. 1 provides a partial cross-sectional side view of a normal human eye.

With reference to the figures, FIG. 1 shows a partial cross-sectional view of the anatomy of a normal human eye. Ciliary body 12 is connected to iris 18 and to lens 16 via zonular fibrils 14. The anterior chamber 20 of the eye is bounded on its anterior (front) surface by cornea 24. In the center of iris 18 is pupil 22. Cornea 24 is connected on its periphery to sclera 26, which is a tough fibrous tissue forming the white shell of the eye. Trabecular meshwork 28 is located on the outer peripheral surface of anterior chamber 20. The trabecular meshwork extends 360° circumferentially around the anterior chamber. Located on the outer peripheral surface of meshwork 28 is Schlemm's canal 30. Schlemm's canal extends 360° circumferentially around the trabecular meshwork. At the apex formed between iris 18, meshwork 28 and sclera 26 is angle 32. Conjunctiva 34 is a membrane overlaying sclera 26 and lining the inside of the eyelid (not shown).

Figure 2:
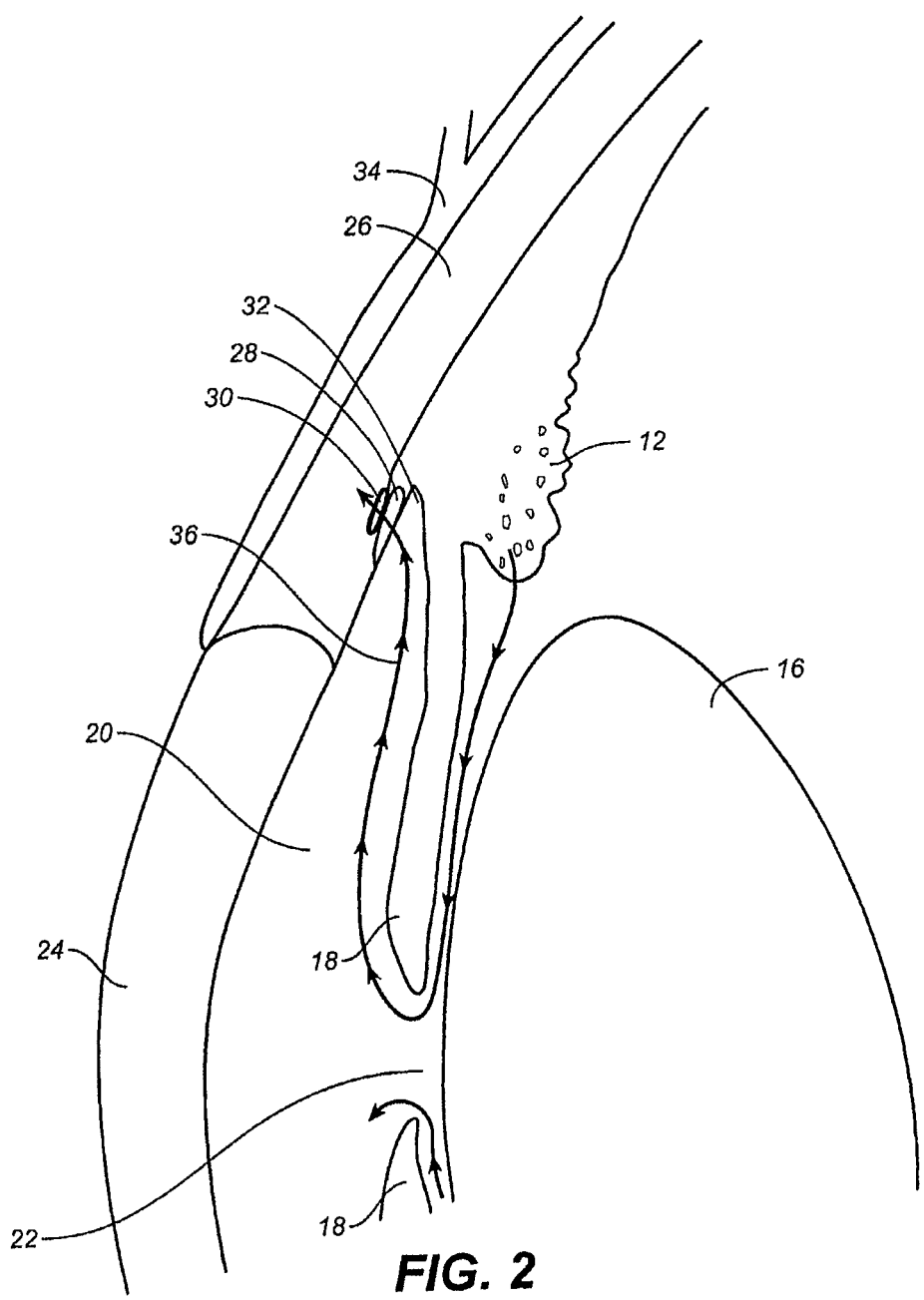
FIG. 2 provides a partial cross-sectional side view of a normal drainage path of fluid from the eye.

FIG. 2 shows a partial cross-sectional view of the flow of aqueous humor within and out of a normally functioning human eye. Aqueous humor is produced in ciliary body 12 and its path through and out of the eye is indicated by solid directional line 36. The aqueous humor flows from ciliary body 12, between lens 16 and iris 18, through pupil 22 into anterior chamber 20, across trabecular meshwork 28, across Schlemm's canal 30, into aqueous veins or collector channels (not shown) and finally into the bloodstream via conjunctival vasculature.

Figure 3:
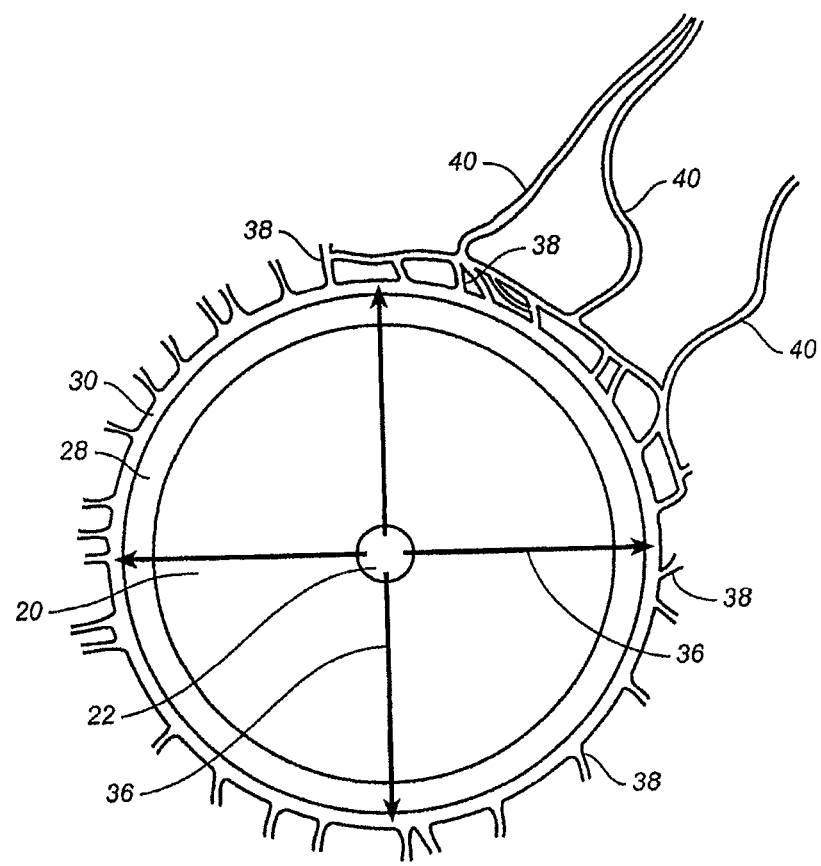
FIG. 3 shows a front view of normal fluid drainage from the eye.

FIG. 3 shows a front view of normal flow of aqueous humor out of the eye. Aqueous humor enters anterior chamber 20 via pupil 22. The fluid flows outwardly toward the periphery of the eye, with the general path of flow indicated by solid directional lines 36. The fluid crosses trabecular meshwork 28 and traverses Schlemm's canal 30 to reach aqueous veins or collector channels 38. In other words, the fluid flows transluminally across Schlemm's canal 30, and into collector channels 38. There are typically 25-50 (e.g., 25-30) collector channels located in a human eye, around the full 360° of Schlemm's canal. The collector channels may, for example, each have a diameter of about 25 microns to about 50 microns. Collector channels 38 are connected to vasculature 40, whereby the drained aqueous humor enters the bloodstream. Although the direction of net or bulk fluid flow is depicted as radially outward by directional lines 36 from pupil 22 for simplicity, actual fluid flow in an eye may follow more varied paths.

Figure 4A:
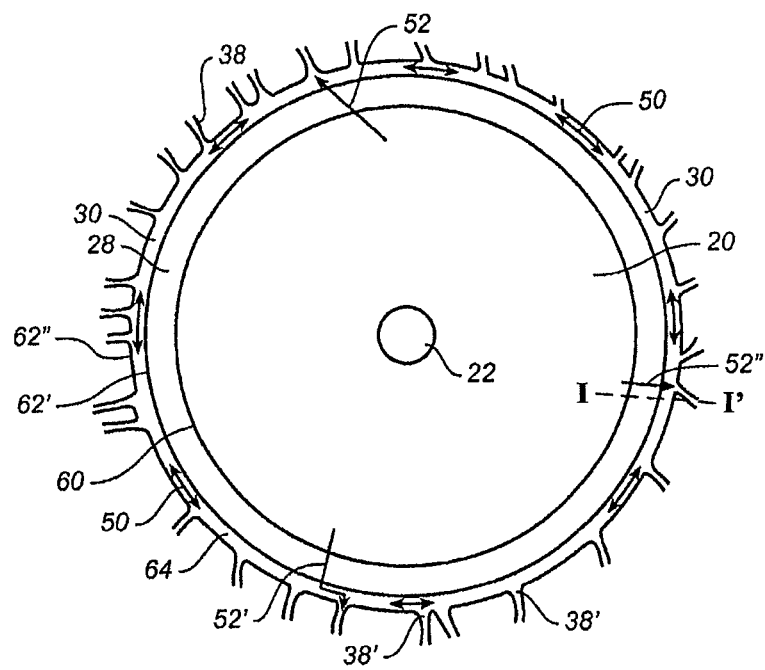
FIG. 4A shows an alternative front view of normal fluid drainage paths from the eye.
Figure 4B:
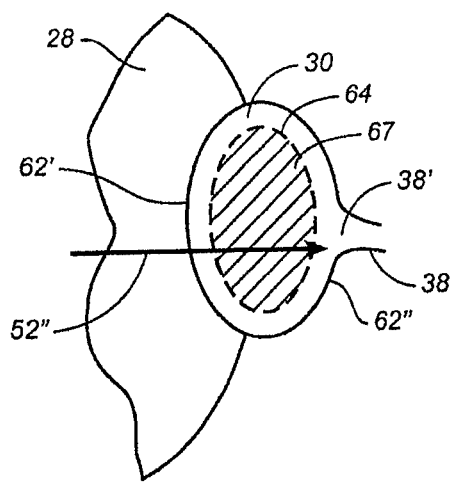
FIG. 4B shows a cross-sectional view along line I-I'.

Different fluid flow paths in and across Schlemm's canal are illustrated in FIGS. 4A and 4B. FIG. 4A shows a front view of an eye, and FIG. 4B shows an expanded cross-sectional view along line I-I'. Circumferential (i.e., longitudinal) flow along and around circular canal 30 is depicted by directional lines 50. Fluid that does not traverse canal 30 to reach collector channels 38 may not be effectively drained from the eye. Examples of fluid flow paths that can effectively drain the eye, including transluminal fluid flow paths (i.e., fluid flow paths that cross the lumen of Schlemm's canal) are illustrated by directional lines 52, 52', and 52". In each of these paths, fluid enters trabecular meshwork 28 along its inner peripheral surface 60 and exits the meshwork along its outer peripheral surface 62'. Meshwork outer peripheral surface 62' provides the inner peripheral surface or wall of Schlemm's canal 30. Transmural fluid flow across Schlemm's canal involves two instances of transmural flow across walls or boundaries. First, fluid must flow from trabecular meshwork 38 through inner peripheral surface or wall 62' of Schlemm's canal 30 to reach lumen 64 of the canal. Second, fluid must flow from lumen 64 through canal outer peripheral wall 62" through apertures 38' to enter collector channels 38. Thus, the fluid must also flow transluminally across the lumen of Schlemm's canal. Finally, the collector channels 38 feed the drained fluid into vasculature. Lumen 64 of canal 30 includes a central core region 67 that does not include the outer periphery of the lumen. As is clearly shown above, fluid flow from the eye differs from fluid flow in other vessels in the body where fluid need only flow longitudinally along the vessel, such as blood flowing through a vein.

Devices

Described here are devices for reducing intraocular pressure, where the devices comprise a support that may be implanted circumferentially in Schlemm's canal to restore or maintain at least partial patency of at least a portion of the canal. The support may or may not occupy at least a portion of a central core of Schlemm's canal. In some variations, the support may not substantially interfere with transmural and/or transluminal flow across the canal, and/or with longitudinal flow within the canal.

By "restore or maintain at least partial patency" of at least a portion the canal, it is meant that the support operates to keep at least a portion of the canal at least partially unobstructed to transmural or transluminal flow, such that fluid can 1) exit through the trabecular meshwork; 2) traverse the canal; and 3) drain via the collector channels. To restore or maintain at least partial patency of the canal, it is not necessary that the support leave the canal unobstructed in regard to circumferential flow. However, supports described here may, of course, be configured to leave the canal unobstructed to circumferential flow.

By "does not substantially interfere" with transmural flow, it is meant that the support does not significantly block either fluid outflow across and from the trabecular meshwork or fluid outflow to and through the collector channels. By "does not substantially interfere" with transluminal flow, it is meant that the support does not significantly block fluid flow across the lumen of the canal. In many variations, the support may allow between about 0.1 microliter per minute and about 5 microliters per minute aqueous outflux from the eye through the trabecular meshwork and collector channels.

The "central core of Schlemm's canal" refers to the region around the cross-sectional center of the canal in the interior space of the canal lumen (i.e., not including the periphery of the canal). Therefore, a device that occupies at least a portion of a central core of Schlemm's canal may traverse at least a portion of the canal's lumen. In some cases, a device may completely traverse the central core of Schlemm's canal.

Additionally, Schlemm's canal includes septae (or endothelial tubules), which are structures that are located periodically through the canal. Without wishing to be bound by theory, it is believed that septae may serve as structural bridges that help to keep the canal patent, by extending from the inner wall of the canal (a portion of the interior surface of the canal that is coincident with an outer peripheral boundary of the trabecular meshwork) to the outer wall of the canal (a portion of the interior surface of the canal having collector channels extending therefrom). In this way, septae may function similarly to bridge supports. It is believed that over time, septae (e.g., aged or faulty septae that have weakened or lost their structural integrity) may help to contribute to collapse of Schlemm's canal or portions thereof, in the presence of normal or high pressure. In such cases, devices described herein may help to replace lost structural septae function, thereby helping to restore or maintain the patency of the canal.

It is also believed that Schlemm's canal in some subjects may include pathologic septae that are essentially walls of scarring that form over time, compartmentalizing Schlemm's canal and thereby restricting or preventing longitudinal flow. In such cases, supports described herein may have tip portions that are blunted and that may be able to push through the pathologic septae, piercing them and thereby restoring longitudinal flow. It should be understood that the supports may alternatively or additionally comprise one or more other features that may be capable of disrupting or removing pathologic septae.

Devices described here need not comprise an open-ended tubular support placed longitudinally along Schlemm's canal—in other words, the devices and supports may be non-tubular. A longitudinal, open-ended tubular support may enable longitudinal flow along the canal. However, even if fluid can flow longitudinally (i.e., circumferentially) along Schlemm's canal, the eye may not be effectively drained unless the fluid eventually traverses or crosses the canal. That is, transmural fluid flow across two boundaries must occur: 1) fluid must flow from the trabecular meshwork through a canal inner wall coincident with an outer peripheral boundary of the trabecular meshwork to reach the canal lumen; and 2) fluid must flow from the canal lumen through apertures in the canal outer peripheral wall to reach the collector channels. Overall, transmural flow should occur. The collector channels may then further disperse the fluid and complete the natural draining process. A tubular support inserted longitudinally into the canal may have significant surface area overlap with the interior surface of the canal, such that transmural flow and/or transluminal flow across the canal may be significantly impeded. A longitudinal tubular support placed in Schlemm's canal may block flow into the canal from the trabecular meshwork and block flow out of the canal into the collector channels.

Devices described herein for treating elevated intraocular pressure include a support that is implanted within Schlemm's canal. In many instances, the device may reduce the intraocular pressure by 1-40 mm Hg, for example by at least 2 mm Hg. In other instances, the device may reduce intraocular pressure by at least 4 mm Hg, or at least 6 mm Hg, or at least 10 or 20 mm Hg. In still other instances, the device may operate to bring the intraocular pressure into the range of about 8 to about 22 mm Hg. The support may be configured in a variety of ways to at least partially prop open Schlemm's canal, thereby restoring or maintaining its patency without substantially interfering with or impeding transmural or transluminal fluid flow across Schlemm's canal. In some variations, the support may not interfere with or block longitudinal flow along or around the canal, while in other variations the support may interfere with or block longitudinal flow along or around the canal. In many instances, the support may be contained entirely within Schlemm's canal. In some variations, the support may be implanted within the canal, but may extend partially beyond Schlemm's canal (e.g., into the trabecular meshwork and/or into the anterior chamber).

In certain variations, a support that restores or maintains at least partial patency of Schlemm's canal to enable fluid flow between an inner wall of the canal and an outer wall of the canal may comprise elements or structures such as bead-like elements or beads. The elements or structures may be connected together (e.g., as a string of beads). Individual elements or beads may be inserted directly into Schlemm's canal, or a connected group of elements or beads may be inserted directly into Schlemm's canal. A more detailed description of supports incorporating elements or beads is provided below.

Figure 5A:
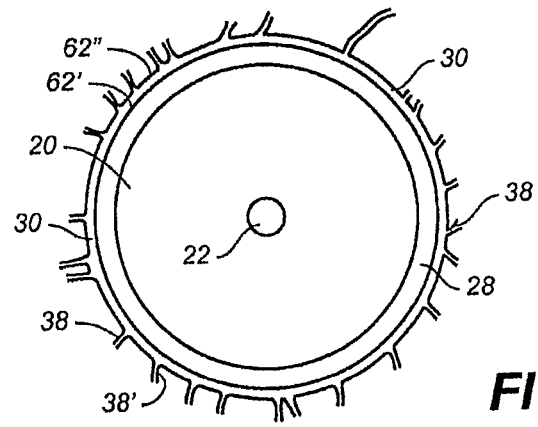
FIG. 5A provides a front view of an eye in which Schlemm's canal is narrowed or collapsed.

FIG. 5A illustrates a front view of an eye having a narrowed or collapsed Schlemm's canal 30, where canal outer peripheral wall 62" is very close to canal inner peripheral wall 62'. Although Schlemm's canal 30 is depicted in FIG. 5A as being uniformly narrow around the entire circumference of canal, it is possible that only a portion of Schlemm's canal is narrowed or collapsed. When Schlemm's canal is collapsed or narrowed, net efflux of aqueous from the anterior chamber to the collector channels 38 is diminished, thereby increasing intraocular pressure. As a result, the risk of pre-glaucoma, ocular hypertension, or glaucoma can increase.

Figure 5B:
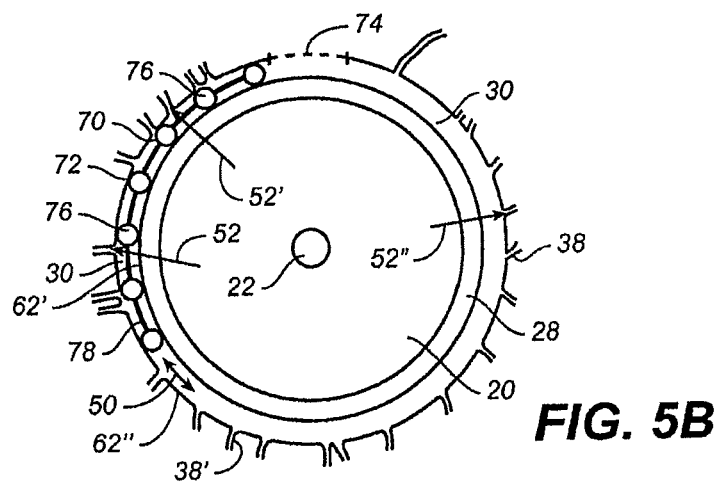
FIG. 5B shows a front view of a device including a support inserted into Schlemm's canal that allows transmural and transluminal flow across the canal.

FIG. 5B illustrates an example of a device 70 inserted into Schlemm's canal 30 through incision site 74. Device 70 in this example is positioned to one side of incision site 74. Device 70 includes support 72, which is configured to keep Schlemm's canal at least partially open to transmural fluid flow across both canal inner wall 62' and canal outer wall 62" to reach collector channels 38 via apertures 38'. Support 72 may allow for transluminal flow across the canal. In the example shown in FIG. 5B, support 72 includes elements or beads 76 connected with connectors 78. In this variation, the distance between canal inner wall 62' and outer wall 62" is approximately determined by the cross-sectional dimension of support 72, which is in turn determined by the largest cross-sectional diameter of the beads 76. Therefore, circumferential (i.e., longitudinal) fluid flow around and along the canal 30 indicated by directional line 50 may be inhibited by the insertion of support 72 into the canal. However, transmural flow across both walls or boundaries of the canal indicated by directional lines 52, 52', 52" may be enhanced by support 72, and fluid may be able to reach collector channels 38 and be drained from the eye. As a result, support 72 may effectively reduce intraocular pressure by utilizing the eye's natural drainage mechanism. Incision 74 need only be large enough to accommodate the diameter of beads 76, so that trauma to the eye is minimized. Beads or other elements may have cross-sectional dimensions in the range from about 50 microns to about 500 microns (e.g., about 100 microns to about 400 microns, about 200 microns to about 300 microns). Insertion of beads or other elements having relatively small cross-sectional diameters (e.g., about 50 microns) into Schlemm's canal opens the canal less than the normal cross-sectional diameter of the canal (which is, for example, approximately 100 microns to 300 microns in cross-sectional diameter), but may still restore or maintain at least partial patency of the canal. Insertion of beads or other elements having relatively large cross-sectional diameters (e.g., greater than about 300 microns) may open the canal as large as or larger than the canal's normal cross-sectional diameter and may also operate to stretch the trabecular meshwork. Stretching the trabecular meshwork may further enhance drainage.

Figure 5C:
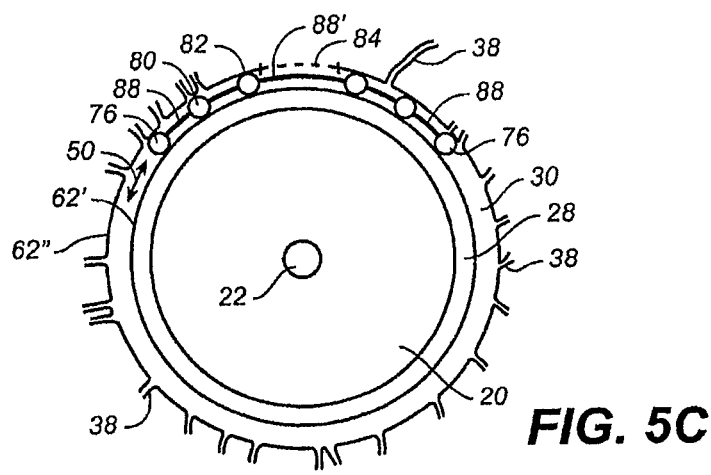
FIG. 5C illustrates an alternate design for a device inserted into Schlemm's canal that allows transmural and transluminal flow across the canal.

FIG. 5C illustrates an alternate configuration of a device 80 inserted into Schlemm's canal 30 through incision site 84. Device 80 includes a support 82 that extends to both sides of incision site 84. Support 82 includes elements or beads 76 connected with connectors 88 and 88'. In this example, connector 88' is of a different length from connectors 88. As in FIG. 5B, beads 76 may impede circumferential (i.e., longitudinal) fluid flow around and along canal 30 indicated by directional line 50. However transmural and transluminal flow across the canal is enhanced by support 82 that restores or maintains at least partial patency across the canal and allows fluid to reach collector channels 38. If the beads are fenestrated or comprise rough, spiked, and/or fluted perimeters (or other similar features), then circumferential fluid flow through or around the beads may also occur.

Figure 6A:
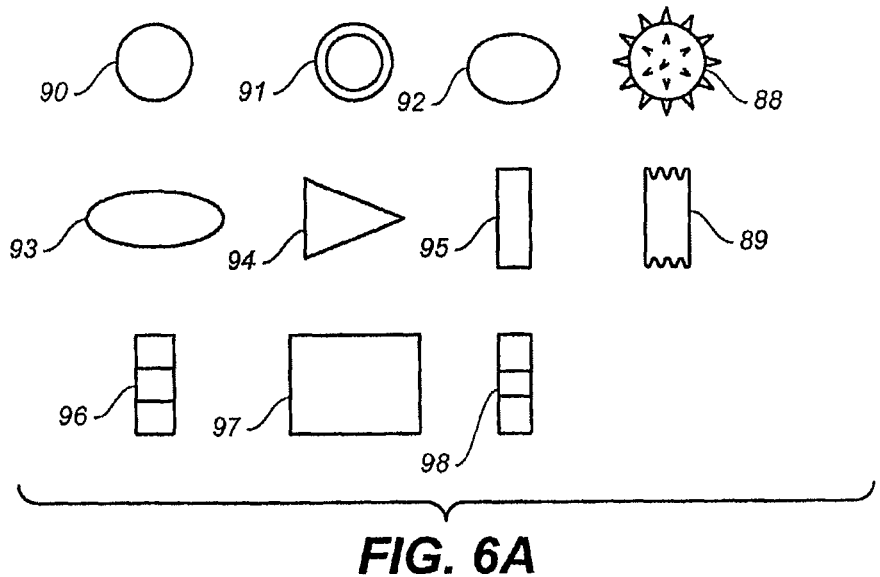
FIG. 6A shows side views of various element or bead configurations that may be used in the supports described herein.
Figure 6B:
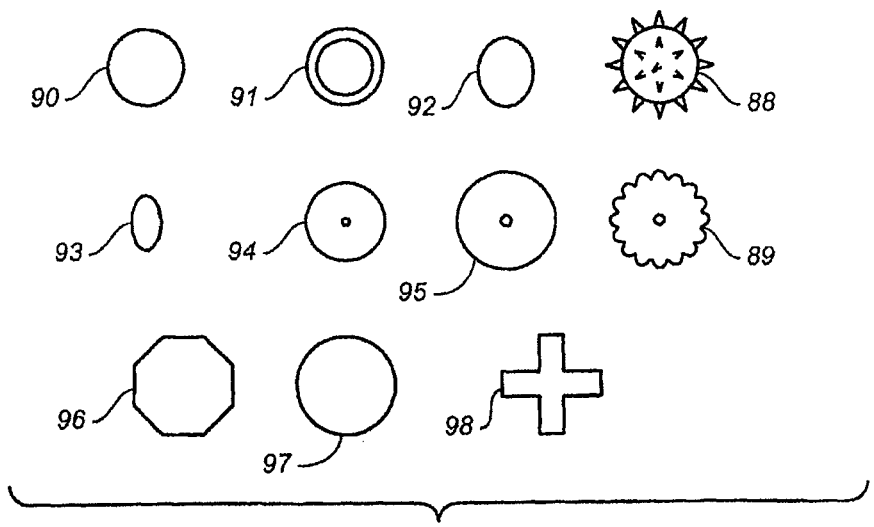
FIG. 6B shows the corresponding front views of the element or bead configurations shown in FIG. 6A.
Figure 6C:
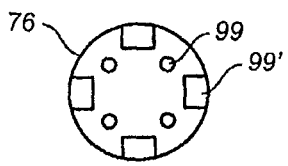
FIG. 6C illustrates an element or bead having fenestrations.

Elements or beads used in a support may be hollow and closed structures, open structures, solid structures, porous structures, or any combination thereof, and may be of any suitable shape. FIGS. 6A and 6B illustrate side and front views, respectively, of exemplary elements or beads that may be used in the supports described here. As shown, solid 90 or hollow 91, spherical 90, spheroid 92, ovoid 93, conical 94, disk-shaped 95, polyhedral 96, rod-like 97, or beads with fluted edges 98, rough edges, 89, or spiked edges 88 may be used. In some instances, it may be desired to round corners or edges of the beads or elements. As illustrated in FIG. 6C, elements or beads 76 may include fenestrations 99 and 99'. Fenestrations may have any suitable cross-sectional shape, such as round or quadrilateral. Although a disc-shaped bead 76 is shown in FIG. 6C, any shape of bead can be fenestrated.

Figure 7A:
FIG. 7A illustrates a support having multiple juxtaposed beads.
Figure 7B:
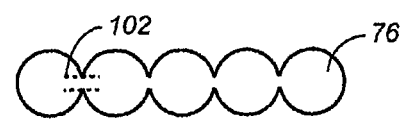
FIG. 7B illustrates a support having multiple juxtaposed and connected beads.
Figure 7C:
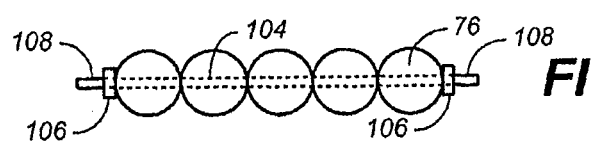
FIG. 7C shows an alternate configuration of a support having multiple juxtaposed and connected beads.
Figure 7D:
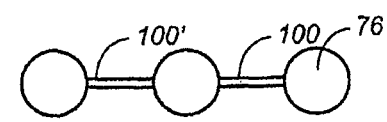
FIG. 7D shows a support having multiple, spaced-apart but connected beads.
Figure 7E:
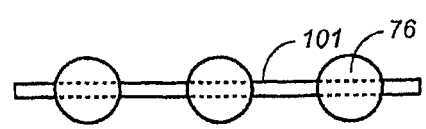
FIG. 7E illustrates beads threaded onto a connector.

As illustrated in the variations shown in FIGS. 7A-7E, two or more beads 76 in a support may be adjacent to each other. Adjacent beads may be juxtaposed (FIG. 7A), connected and juxtaposed (FIGS. 7B and 7C), or connected together with connectors 100 and 100' to form intervals between beads (FIG. 7D). In addition, beads may be threaded onto a connector 101 (FIG. 7E). Multiple beads used in a single support may have the same or different shapes, and may be made of the same or different materials.

Junctions 102 between beads or other elements as shown in FIG. 7B may be made using any suitable technique, such as by using an adhesive, chemical bonding, mechanical interlocking, and/or welding. Beads or other elements may also be juxtaposed and connected as shown in FIG. 7C by threading onto a guide element 104. Guide element 104 may comprise a fiber, a suture, a guide wire, a fixture, or the like. The beads or other elements may be fixed in a juxtaposed configuration on a guide element, for example, by knotting ends of the fiber or by providing other end-blocking devices 106, such as clips, caps, protrusions, or the like on ends 108 of element 104. Any or all of the beads or other elements may be attached to guide element 104. For example, beads or other elements occupying end positions may be attached to element 104 and may function as blocking beads to keep beads from sliding off ends 108 of element 104. Alternatively, beads may slide along element 104. Guide element 104 may be flexible, and may be formed of, for example, thin polymer threads, such as a suture, or metal wires. Alternatively, element 104 may be flexible but fixable, such as one or more shapeable metal wires that may be bent into a desired position and that may maintain that position against some amount of external stress or pressure. In other variations, guide element 104 may be rigid (e.g., a molded polymeric piece or a stiff metal piece).

As shown in FIG. 7D, multiple connectors 100, 100' may be used in a single support, with at least one connector inserted between adjacent beads 76 or other elements. If multiple connectors are used, they may be of the same or different lengths. In addition, multiple connectors within the same support may be made of the same or different materials, and the connectors and beads may be made of the same or different materials. Discrete connectors 100 and 100' may be inserted between beads 76 and attached to adjacent beads using any suitable method including using adhesives, chemical bonding, welding, mechanical interlocking, knots, or any combination thereof. In some variations, connectors 100 and 100' between beads may be configured to function as spacers between individual beads. As illustrated in FIG. 7E, beads 76 may also be threaded onto a connector 101. If the beads are threaded onto a connector, the beads may be maintained in fixed positions along the connector 101 by any suitable method, including using adhesives, chemical bonding, welding, clips, protrusions on the connector, mechanical interlocking locking between a connector and a bead, knots, or any combination thereof. Alternatively, some or all beads may slide along connector 101. Connectors 100, 100' and 101 may be flexible, such as thin polymer threads or metal wires. Connectors 100, 100' and 101 may also be flexible but fixable, such as shapeable metal wires. Alternatively, connectors 100, 100' and 101 may be rigid, such as molded polymeric connectors or stiff metal connectors.

Supports of the devices described here need not contain beads. As an example, a support may comprise one or more other elements, or may be a unitary structure of fixed or variable length. Supports may be solid, hollow, or porous, or any combination thereof. For example, a support may be partially solid and partially hollow. Examples of support configurations are shown in side view and front view in FIGS. 8A-8F. As illustrated in FIGS. 8A and 8B, a support may have an open network structure. Such a support may be fabricated out of shapeable metal wires, for example. The support illustrated in FIGS. 8A and 8B may have minimal surface area contact with the interior surface of Schlemm's canal—i.e., only point contacts at the end of wires or fibers 170. Alternatively, a support having an open network structure may be at least partially made from a mesh or foam. The mesh or foam may be made of any suitable material (e.g., metal and/or plastic). As shown in FIGS. 8C and 8D, the support may have a sinusoidal or zig-zag configuration extending along a selected length of Schlemm's canal. For the example shown in FIG. 8C, the support may contact the interior surface of Schlemm's canal at least three points, labeled $P_1$, $P_2$, and $P_3$, after implantation. In FIGS. 8E-8H, examples of rod-like supports having fluted edges are shown. In FIGS. 8E and 8F, fluted edges 110 extend longitudinally along sides 112 between ends 114 of the support to form structures 116. Structures 116 may include fenestrations 113. The support may include central bore 117. In FIGS. 8G-H, fluted edges 110' extend along sides 112' to form structures 116'. Structures 116' have serrated outer surfaces 115' extending between ends 114'. The support may include central bore 117'. In the variations illustrated in FIGS. 8E-8H, the support may contact the canal walls at least four points. In some variations, the support may be adjustable. The surface of the support may be rough, smooth, spiked or fluted, for example.

A common characteristic of the support configurations described here is that they need not have continuous or extensive contact with the interior surface of Schlemm's canal. Indeed, many of the described devices and structures may have minimal tangential, periodic, or sporadic contact with the interior surface, and/or may contact the interior surface only along certain lines and/or at certain points of the devices and structures. In some variations, less than about 90% (e.g., less than about 80%, less than about 70%, less than about 60%, less than about 50%, less than about 40%, less than about 30%, less than about 20%, less than about 10%, less than about 5%, less than about 3%, less than about 1%) and/or more than about 0.5% (e.g., more than about 1%, more than about 3%, more than about 5%, more than about 10%, more than about 20%, more than about 30%, more than about 40%, more than about 50%, more than about 60%, more than about 70%, more than about 80%) of the surface area of the outer surface of a support may contact the interior surface of Schlemm's canal when the support is in use. Devices and structures described here may, for example, have significantly less planar contact with the interior surface of Schlemm's canal than, for example, a hollow tubular stent, such as a hollow tubular cardiovascular stent.

As demonstrated by the example shown in FIGS. 8A and 8B, some supports only have point contacts with the interior surface of a canal wall. For the supports shown in FIGS. 5B and 5C, the rounded beads of each of the supports make only tangential contact with the interior surface of a canal wall. Bead shapes may be selected or designed to have minimal surface area contact with the interior surface of Schlemm's canal. For example, beads 98 having fluted edges as shown in FIGS. 6A and 6B may have low surface area contact with the interior surface of the canal. In addition, supports may have widely spaced apart beads—for example, the connectors illustrated in FIGS. 7D and 7E may function to space beads at desired intervals to reduce contact with canal walls yet operate to keep the canal open. As illustrated above with respect to FIGS. 8C and 8D, in some variations, a support may contact the interior surface of the canal at least two points, or at least three points (e.g., four points, five points, six points, seven points, eight points, nine points, 10 points, etc.).

Figure 9A:
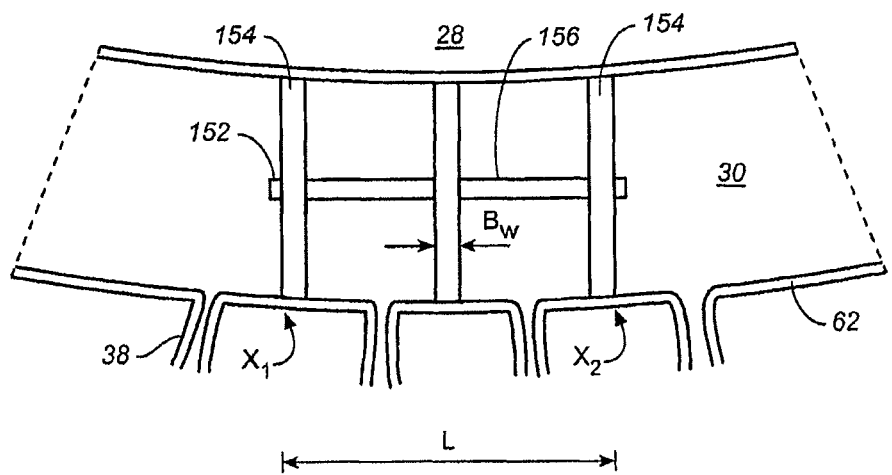
FIGS. 9A and 9B show expanded cross-sectional views of a support implanted within Schlemm's canal.
Figure 9B:
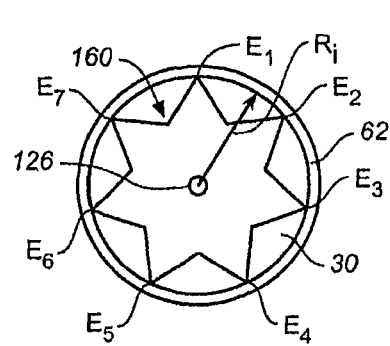

Expanded cross-sectional views of a support 152 implanted circumferentially in Schlemm's canal are provided FIGS. 9A and 9B. The fraction of canal wall surface area in contact with a support can be estimated by viewing the inside of Schlemm's canal as a slightly arcuate cylinder C having length L, extending circumferentially from a first end $X_1$ to a second end $X_2$ of support 152, and inside radius $R_i$. In some variations, the support may contact less than 90% (e.g., less than 80%, less than 70%, less than 60%, less than 50%, less than 40%, less than 30%, less than 20%, less than 10%, less than 1%, less than 0.1%) of the surface area of the cylinder C as described above. For example, the support 152 shown in FIGS. 9A and 9B contacts the interior surface of the canal wall 62 only at bead outer peripheral edges at $E_1$-$E_7$, along a distance of the bead width $B_w$. There is no contact with the interior surface of the canal where connectors 156 space apart beads 154, and no contact in fluted regions 160 of beads 154. The design feature of minimal support contact with the interior surface of the canal allows a support to restore or maintain at least partial patency of the canal without substantially interfering with transmural or transluminal flow across the canal. If a substantial portion of the surface area of the inner periphery of the canal adjacent to the trabecular meshwork or of the surface area of the outer periphery of the canal where the collector channels are located is blocked, effective fluid flow across or within the canal may be impaired.

Supports can have variable lengths and thicknesses. For example, the length of supports using beads may be adjusted by varying the number, type, or spacing of beads, or any combination thereof. The thickness of a support may be increased by adding one or more beads having larger dimensions. Unitary supports may also be built with varying lengths, or with adjustable (e.g., trimmable) dimensions. For example, for a support made of shapeable metal having a sinusoidal or zig-zag configuration as shown FIGS. 8C and 8D, a cross-sectional dimension 117 of the support may be decreased or increased by, for example, apply tension along dimension 119.

Figure 10A:
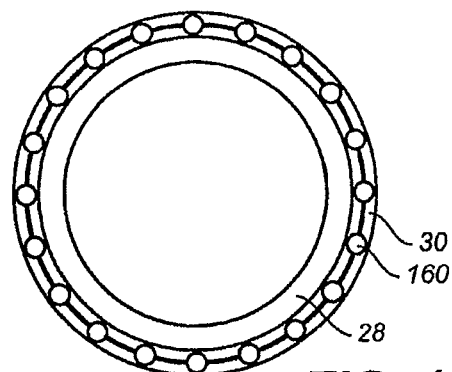
FIGS. 10A-10C illustrate various configurations of supports implanted into Schlemm's canal.
Figure 10B:
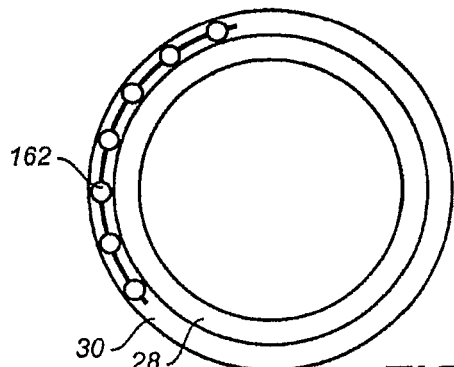
Figure 10C:
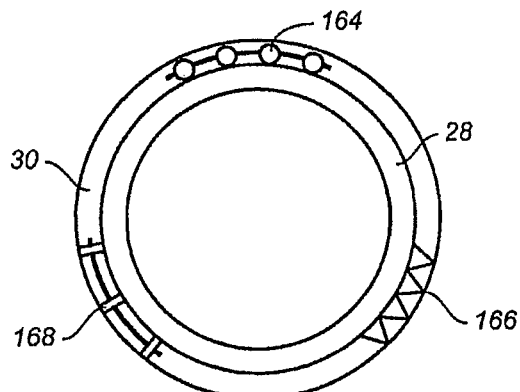

As illustrated in FIG. 10A, a support 160 may extend essentially around the entire circumference of Schlemm's canal 30. Alternatively, a support may extend approximately half way around the circumference of the canal (not shown). As shown in FIG. 10B, a support 162 may extend less than half way around the canal. As shown in FIG. 10C, a support 164 may extend a quarter or less of the circumference around the canal. In addition, more than one support 164, 166, or 168 may be inserted into a single Schlemm's canal. If multiple supports are inserted into a single canal, they can be of different shapes, lengths, materials or sizes, or at least two of the supports can be the same.

Figure 11A:
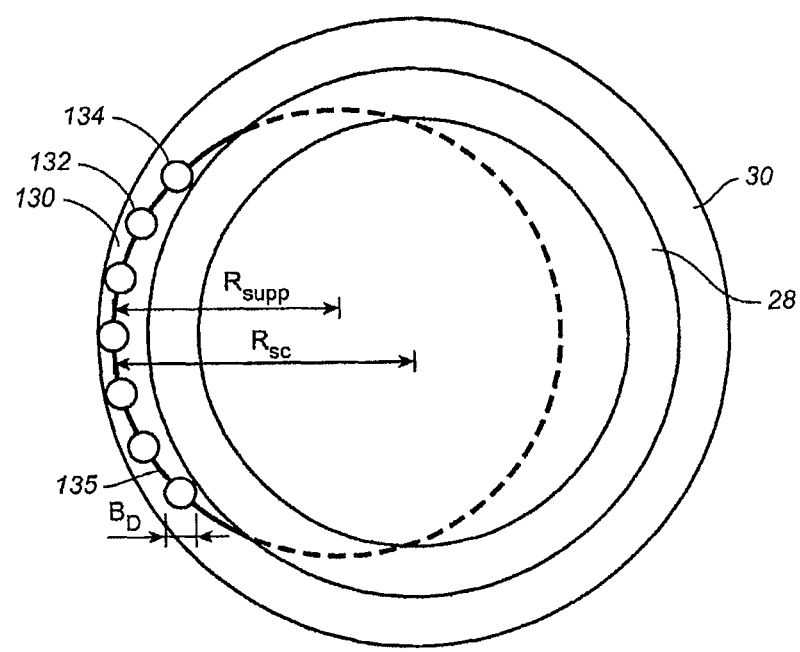
FIGS. 11A and 11B illustrate two configurations of supports having a smaller radius of curvature than Schlemm's canal.
Figure 11B:
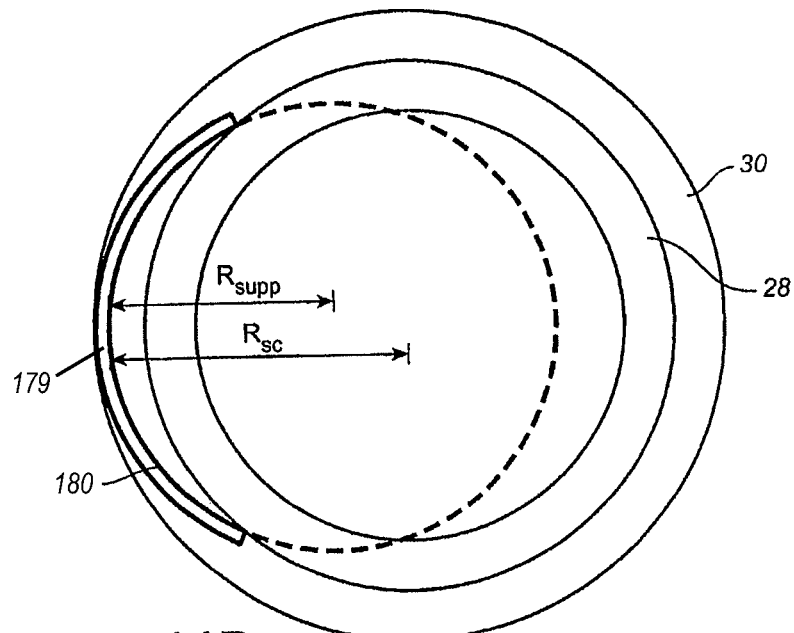
Figure 11C:
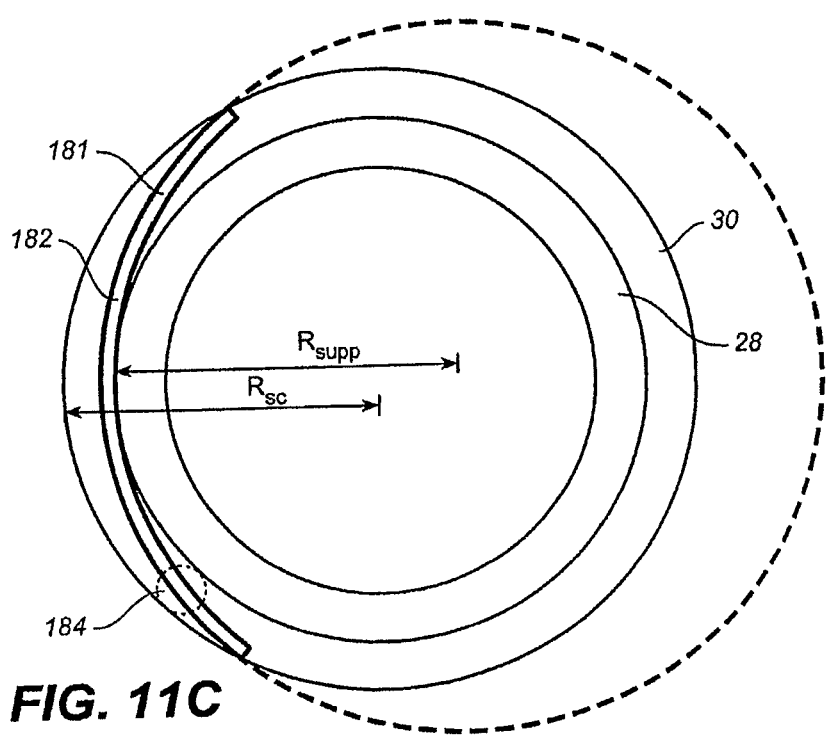
FIG. 11C shows a support having a larger radius of curvature than Schlemm's canal.

A support may be configured such that it will open the canal beyond a maximum cross-sectional dimension of the support itself. For example, FIG. 11A shows a device 130 comprising a support 132 that is inserted into Schlemm's canal 30. Support 132 comprises beads 134 which have a maximum cross-sectional dimension $B_D$. Support 132 comprises a stiff arcuate element 135 with a radius of curvature $R_{supp}$ smaller than the radius of curvature of Schlemm's canal $R_{SC}$. The smaller, fixed radius of curvature $R_{supp}$ of arcuate member 135 urges canal 30 to open more than $B_D$. In another variation shown in FIG. 11B, support 179 comprises an arcuate member 180 without beads having a radius of curvature $R_{supp}$ that is less than the radius of curvature $R_{SC}$ of the canal. Member 180 is sufficiently stiff to urge the canal open. In another variation shown in FIG. 11C, support 181 comprises an arcuate member 182 having a radius of curvature $R_{supp}$ larger than that of Schlemm's canal $R_{SC}$. Member 182 is also sufficiently stiff to urge the canal open. Arcuate members 135, 180 and 182 can comprise a shape memory material such as a nickel-titanium alloy (e.g., Nitinol). As indicated in FIG. 11C, support 181 can include beads 184. Alternatively or additionally, a support may include one or more other elements. To urge open the canal, the radius of curvature $R_{supp}$ of an arcuate members can be, for example, at least about 10% (e.g., about 10%, 20%, 30%, 40%, or 50%) smaller or larger than that of Schlemm's canal $R_{SC}$. For example, an arcuate member can have a radius of curvature of about 3 mm to about 8 mm. In some variations, the radius of curvature of an arcuate member $R_{supp}$ in a support may be at least about 3 mm (e.g., about 3 mm, or about 4 mm, or about 5 mm). In other variations, the radius of curvature $R_{supp}$ of an arcuate member in a support may be at least about 6 mm (e.g., about 6 mm, or about 7 mm, or about 8 mm).

As noted above, supports described here may assume a radius of curvature that is less or greater than that of Schlemm's canal. In some variations, a support may assume a radius of curvature that is less or greater than that of the trabecular meshwork. Moreover, in certain variations, a support may expand or remodel when at least partially positioned within Schlemm's canal. Upon such expansion or remodeling, the support may disrupt the trabecular meshwork or inner wall of the canal by expanding beyond the diameter of the canal itself. This may, for example, cause the support to push into the trabecular meshwork or pull on it and disrupt it. In some variations, a support may perforate the walls of the canal or the trabecular meshwork upon expanding and/or remodeling. A support may also perforate the walls of the canal or the trabecular meshwork upon being delivered to and/or positioned at a target site.

The supports described here may occupy at least a portion of a central core of Schlemm's canal and in some cases may completely traverse the central core. The central core of Schlemm's canal is the region around the cross-sectional center of the canal in the interior space of the canal lumen. A support that occupies at least a portion of the central core of the canal can traverse at least a portion of the canal lumen. For example, some variations of supports can traverse the cross-sectional center of the canal at least one point. Referring to FIG. 12A, a front view of a support 220 having beads 222 connected with connectors 224 is provided. FIG. 12B shows an expanded cross-sectional view along line II-II'. Support 220 occupies a portion canal central core 67 in canal lumen 64. Trabecular meshwork 28 is shown adjacent to canal 30. In this variation, support 220 traverses the cross-sectional center 66 of the canal. In other variations, supports can traverse the lumen of the canal off-center (e.g., appearing as a chord across the canal lumen in cross-section). Referring to FIG. 12C, a front view of an arcuate support 210 is shown. FIG. 12D shows an expanded cross-sectional view along line III-III'. Support 210 traverses and occupies a portion of central core 67 in lumen 64 of canal 30 without passing through canal center 66. In some variations, the support may occupy the majority of the central core of the canal. Referring to FIG. 12E, a front view of support 230 comprising disc-like beads 232 is shown. A cross-sectional view along line IV-IV' is shown in FIG. 12F. As illustrated in FIG. 12F, bead 232 with fenestrations 234 occupies the majority of central core 67 of canal 30. In other variations, the support occupies only a small portion of the central core of the canal. For example, in FIG. 12G, a front view of a support 240 having an open network structure is shown. A cross-sectional view along line V-V' is shown in FIG. 12H.

While certain variations of supports have been described, other variations of supports having any appropriate configuration may be used.

Figure 13A:
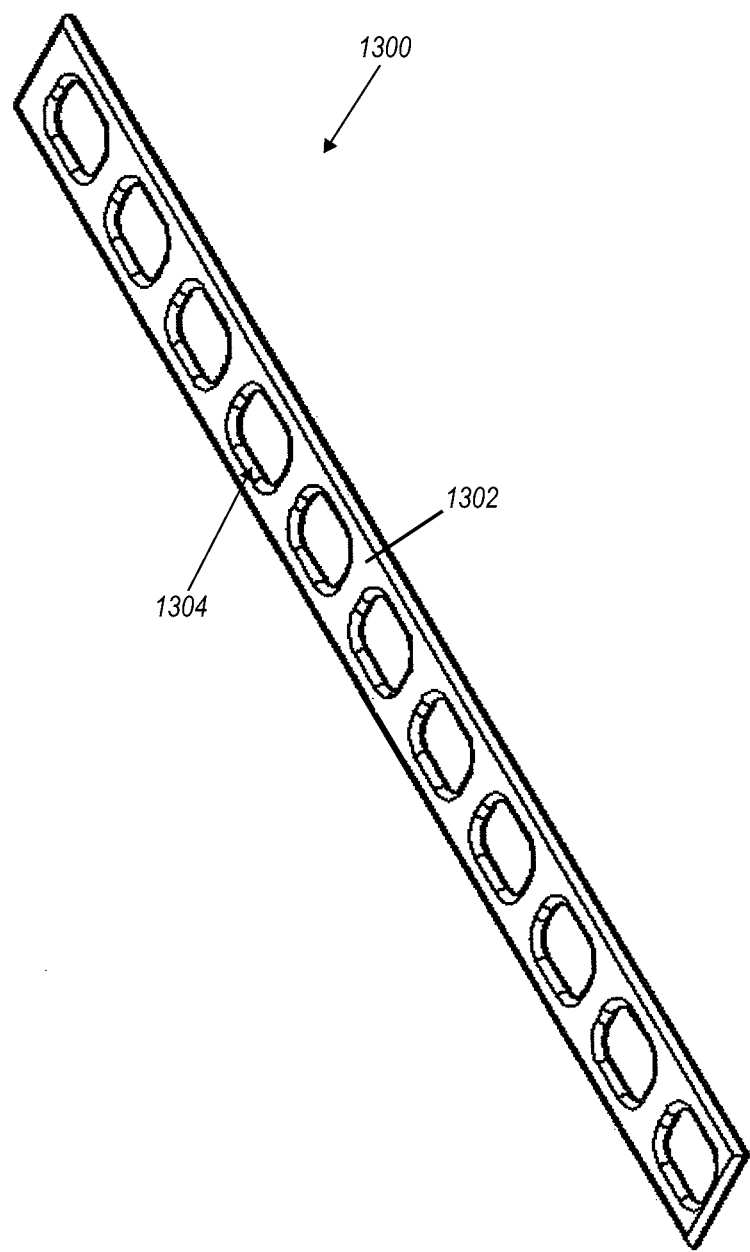
FIGS. 13A and 13B are illustrations of additional variations of supports that are implantable within Schlemm's canal.
Figure 13B:
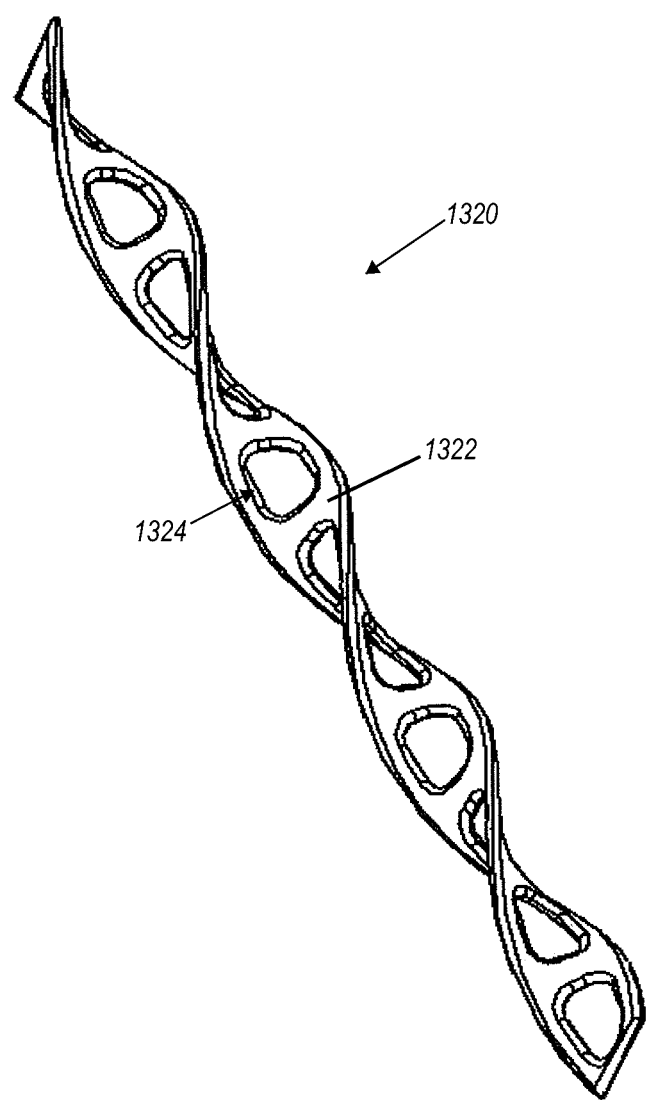

In some variations, a support may be relatively flat, or may comprise one or more relatively flat components. For example, FIG. 13A shows a support 1300 comprising a flat ribbon member 1302. As shown, ribbon member 1302 has multiple fenestrations 1304, although other variations of supports may comprise ribbon members having fewer fenestrations, fenestrations with different sizes or configurations, or even no fenestrations at all. Moreover, while not shown here, in some variations, a ribbon member or other support component may have rounded, relatively atraumatic edges. Additionally, supports described here may be curved or otherwise shaped, such that they are not necessarily straight and elongated. For example, FIG. 13B shows a support 1320 comprising a flat ribbon member 1322 having fenestrations 1324, where the flat ribbon member has been twisted into a configuration similar in appearance to a double helix.

Figure 14A:
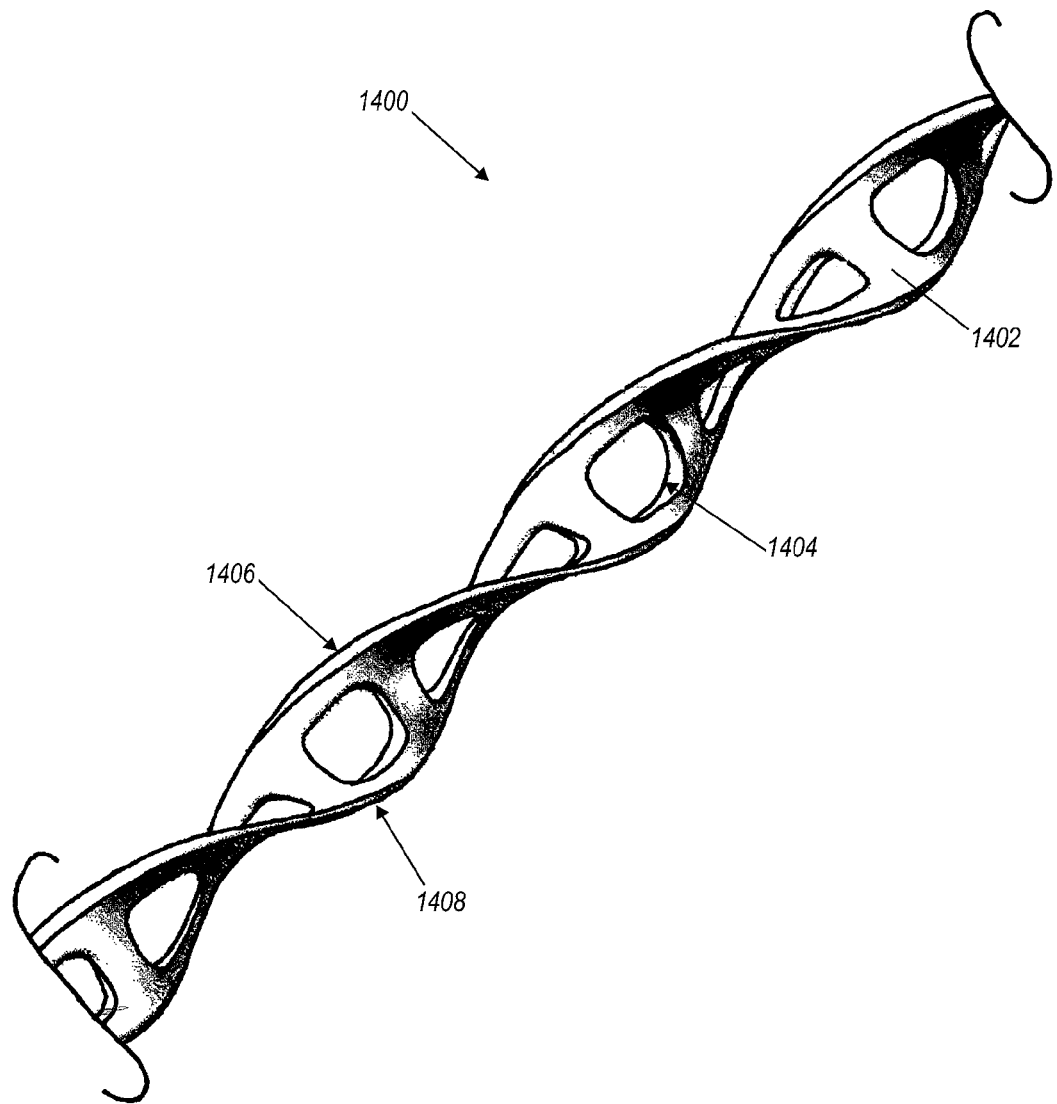
FIG. 14A is an illustration of another variation of a support that is implantable within Schlemm's canal.
Figure 14B:
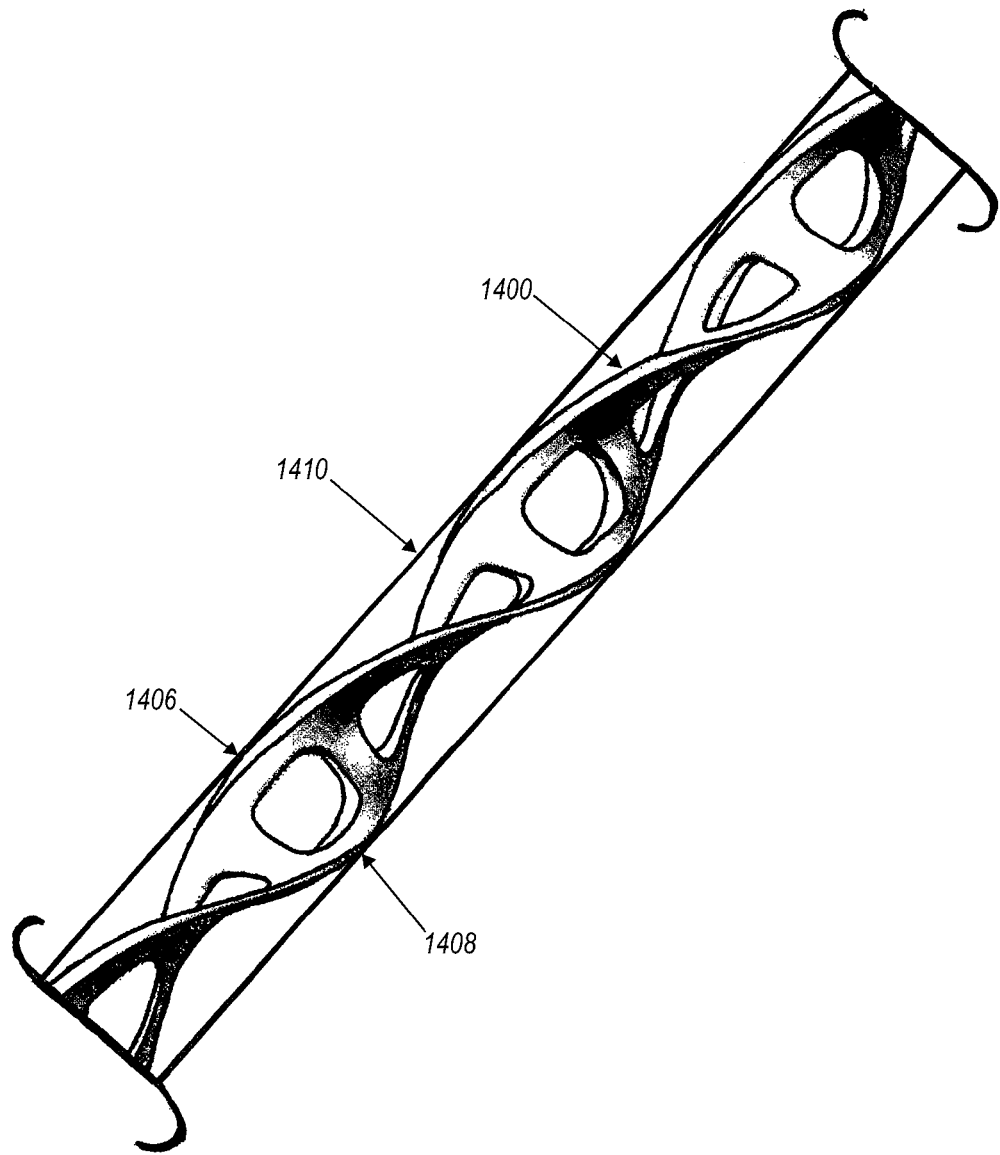
FIG. 14B is an illustrative depiction of the support of FIG. 14A positioned within a portion of Schlemm's canal.

FIG. 14A depicts another variation of a support 1400 comprising a ribbon member 1402 that has been twisted into a configuration similar in appearance to a double helix. As shown there, ribbon member 1402 comprises fenestrations 1404 and includes edges 1406 and 1408. FIG. 14B shows support 1400 disposed within Schlemm's canal 1410, with edges 1406 and 1408 contacting the interior surface of the canal. For any given cross-section of Schlemm's canal 1410, support 1400 contacts the canal's inner wall at two points (i.e., where edges 1406 and 1408 contact the wall). Of course, support 1400 is only one variation of a support and other variations of supports may contact Schlemm's canal at a different number of points for any given cross-section. The two contact points for support 1400 rotate as a result of the twisting of support 1400, eventually returning 360° to the same location on the next repeating unit. In some cases, a support such as support 1400 may complete a full 360° turn for every 0.5 millimeter to 2 millimeters (e.g., every 1 millimeter to 1.5 millimeters) of the support's length. For example, a support such as support 1400 may complete a full 360° turn approximately every millimeter of the support's length. Supports may have uniform twisting, or the degree of twisting of a support may vary along the support's length.

Figure 14C:
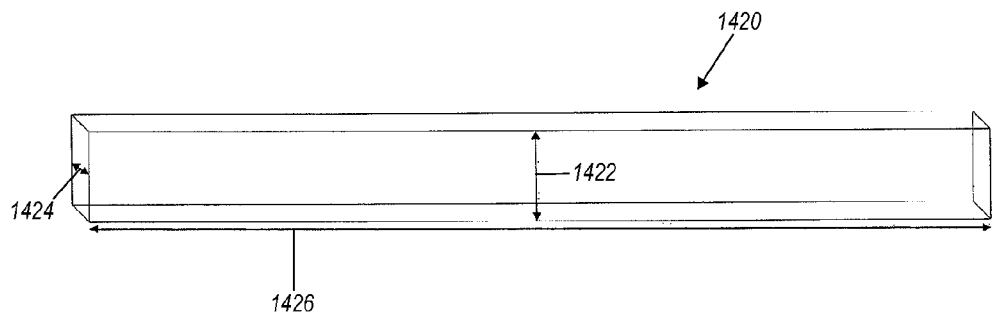
FIGS. 14C-14E depict a variation of a method that may be used to make a support that is implantable within Schlemm's canal.
Figure 14D:
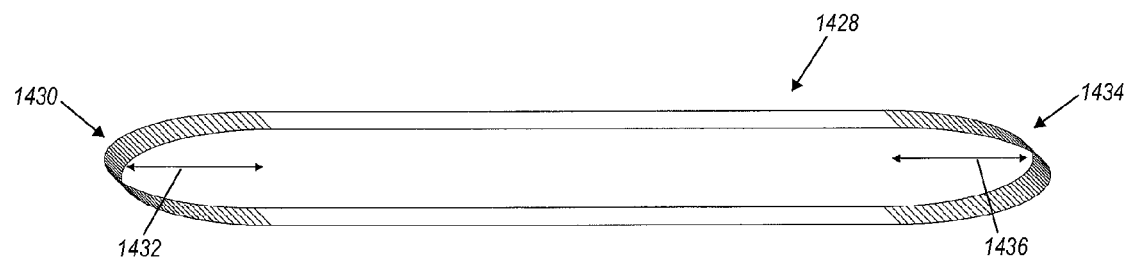
Figure 14E:
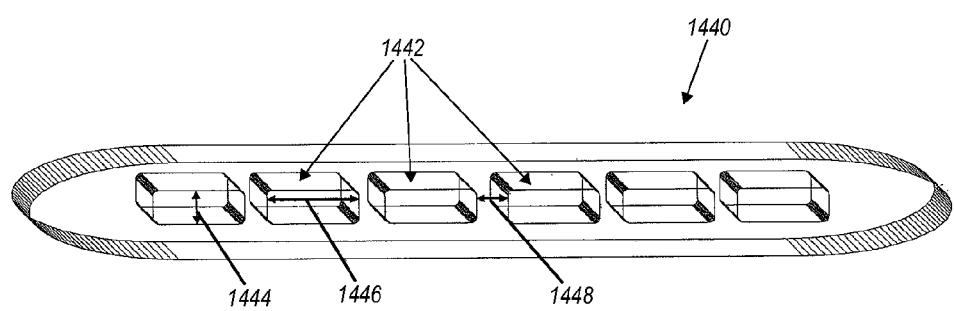

A support such as support 1400 may be formed using any appropriate method, one of which is depicted in FIGS. 14C-14E.

First, referring to FIG. 14C, a ribbon member 1420 (e.g., formed of titanium, stainless steel, Nitinol, etc.) is provided (e.g., by cutting a sheet of the material into individual ribbon members). Ribbon member 1420 has a width 1422, a length 1426, and a thickness 1424. In some variations, width 1422 can be from about 10 microns to about 750 microns (e.g., from about 10 microns to about 600 microns, such as 300 microns), length 1426 can be from about 1 millimeter to about 50 millimeters (e.g., from about 1 millimeter to about 40 millimeters, such as 10 millimeters or 15 millimeters), and/or thickness 1424 can be from about 10 microns to about 150 microns (e.g., from about 25 microns to about 100 microns, such as 50 microns). A ribbon member having a relatively large width may, for example, be suitable for use in a procedure that includes dilating Schlemm's canal. A ribbon member having a relatively long length may, for example, be suitable for use in the Schlemm's canal of an eye that has become enlarged as a result of a congenital glaucoma condition. The length of a ribbon member may be selected so that the resulting support occupies a desired amount of the circumference of Schlemm's canal, such as ⅛ to ½ (e.g., ⅛ to ⅓, ¼ to ½, ¼ to ⅓) of the circumference of Schlemm's canal.

Next, and as shown in FIG. 14D, the ends of the ribbon member are blunted or rounded, to form a first precursor 1428 to the support, where the first precursor has rounded ends 1430 and 1434. The ends may be blunted or rounded using a laser, for example. Blunting or rounding the ends of the ribbon member may, for example, render the ribbon member atraumatic. Ultimately, this may result in a support that is comparatively less traumatic upon delivery. Additionally, blunted or rounded ends may help to easily guide the support down Schlemm's canal. In some variations, a support may comprise rounded ends that are semicircular or elliptical, and that have a diameter of about 10 microns to about 750 microns (e.g., about 10 microns to about 600 microns, such as 300 microns).

In certain variations, a ribbon member may also be deburred (e.g., to remove slag, cutting materials and oxide).

Referring specifically now to FIG. 14E, fenestrations 1442 are then formed in the first precursor (e.g., using a laser), thereby forming a second precursor 1440 to the support. The fenestrations may, for example, provide for enhanced flow of aqueous humor through and across Schlemm's canal when the support is positioned within Schlemm's canal. Fenestrations 1442 each have a width 1444 and a length 1446, and each fenestration is separated from its neighboring fenestration by a distance 1448. In certain variations, width 1444 may be from about 1 micron to about 600 microns (e.g., 125 microns, 150 microns), length 1446 may be from about 1 micron to about 5000 microns (e.g., from about 1 micron to about 500 microns, such as 300 microns), and/or distance 1448 may be from about 1 micron to about 5000 microns (e.g., from about 1 micron to about 300 microns, such as 150 microns). Of course, while fenestrations 1442 are depicted as each having the same size and being located at the same distance from the next fenestration, in some variations, a support may comprise fenestrations of different sizes and/or fenestrations that are separated from each other by different distances. Moreover, any suitable number of fenestrations may be used. In some variations, a support may not have any fenestrations, or may have just one fenestration. In certain variations, a support may have multiple fenestrations, such as 2, 3, 4, 5, 8, 10, 15, 20 23, 24 or 25 fenestrations.

After second precursor 1440 has been formed, the second precursor may be twisted (e.g., around a mandrel, using heat treatment, and or using a vise or vise-like tooling), thereby forming support 1440. In some variations, the twisted support may then be curved, for example, to approximate the curvature of Schlemm's canal. In some cases, the curve may be heat-set into the support (e.g., by positioning the support in a mold having the desired curvature and heat-treating the support to set the curve). In certain variations, the support may be curved to a radius of curvature of about 2 millimeters to about 12 millimeters (e.g., about 3 millimeters to about 9 millimeters, or about 4 millimeters to about 8 millimeters, such as 6 millimeters). In certain variations, a support may not be curved (i.e., the support may be straight).

Additional steps may include electropolishing the support (e.g., to smooth its surface and edges and render it atraumatic) and/or applying a coating (e.g., heparin) to the support.

It should be understood that any of the features or characteristics of particular supports described herein, including methods of making and using the supports, may be applied to other supports as well, as appropriate.

Figure 14F:
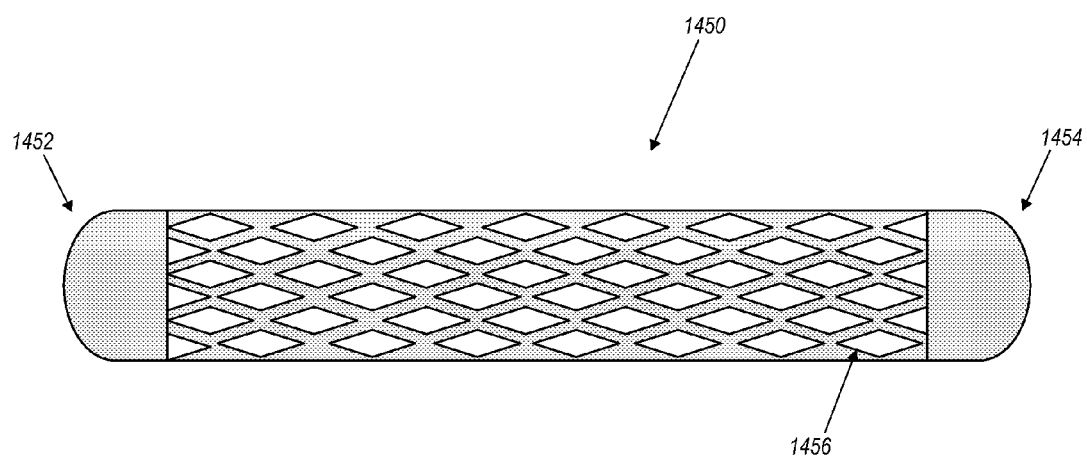
FIG. 14F depicts a variation of a component that may be used to make a support that is implantable within Schlemm's canal.

In variations in which ribbon members are used to form supports, the ribbon members may have any suitable size, shape and configuration. For example, a ribbon member may or may not include one or more fenestrations, and if the ribbon member includes at least one fenestration, the fenestration may have any appropriate shape, such as triangular, rectangular, square, oval, elliptical, circular, etc. In some variations, fenestrations may be in the form of lines or slits. Fenestration size and/or shape may be selected, for example, to enhance the longitudinal strength of the support as it is being positioned within Schlemm's canal (e.g., by using circular and/or elliptical fenestrations). FIG. 14F shows a ribbon member 1450 comprising atraumatic rounded ends 1452 and 1454, and having staggered diamond-shaped fenestrations 1456. For any one cross-section of ribbon member 1450, the amount of ribbon material (e.g., metal) and the amount of fenestration is the same as for any other cross-section of the ribbon member. This may, for example, provide for symmetrical twisting of the ribbon member during formation of the support. Of course, in some cases a ribbon member may include fenestrations (e.g., diamond-shaped fenestrations and/or staggered fenestrations) that do not provide the ribbon member with the above-described features and that do not provide for symmetrical twisting of the ribbon member. Additionally, while ribbon member 1450 comprises diamond-shaped fenestrations that are all of the same size, other variations of ribbon members may comprise fenestrations of different shapes and/or sizes. Moreover, fenestrations may be arranged in any suitable configuration.

Figure 15A:
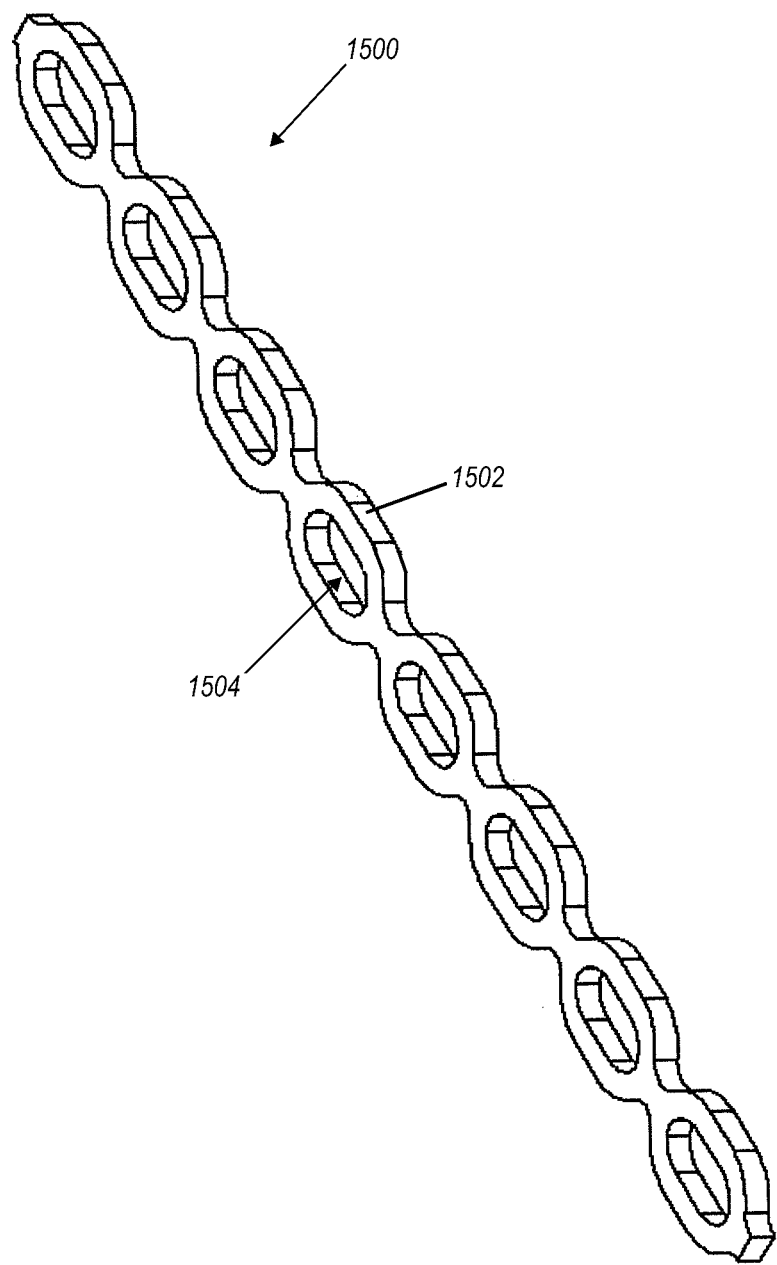
FIGS. 15A and 15B are illustrative depictions of further variations of supports that are implantable within Schlemm's canal.
Figure 15B:
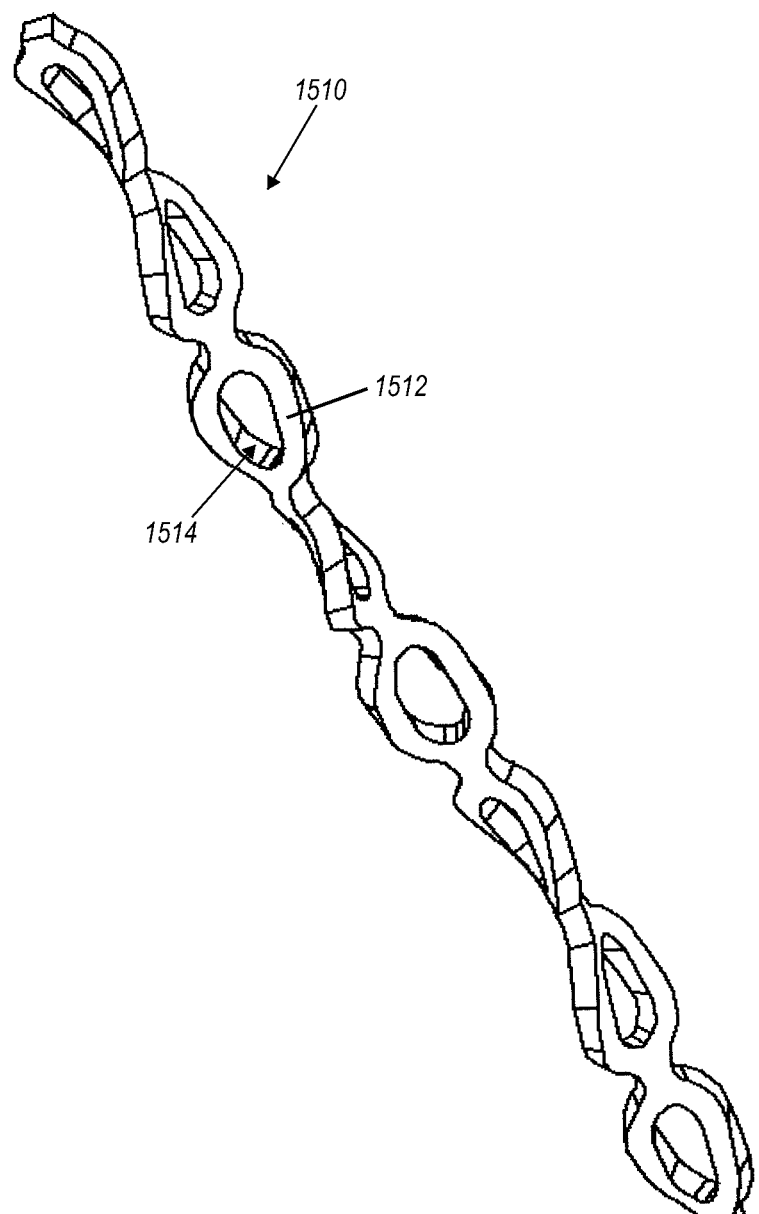

Certain variations of supports may have chain-like configurations. The individual chain "links" may be coupled to each other, or at least some of the individual chain "links" may be integral with each other. As an example, FIG. 15A shows a support 1500 comprising integral chain "link" components, such as component 1502, having a central opening 1504. Of course, as described above, in some variations such a support may be twisted, as is the case with support 1510 in FIG. 15B, which comprises integral chain "link" components, such as component 1512 having a central opening 1514, and which has a twisted configuration.

Figure 16A:
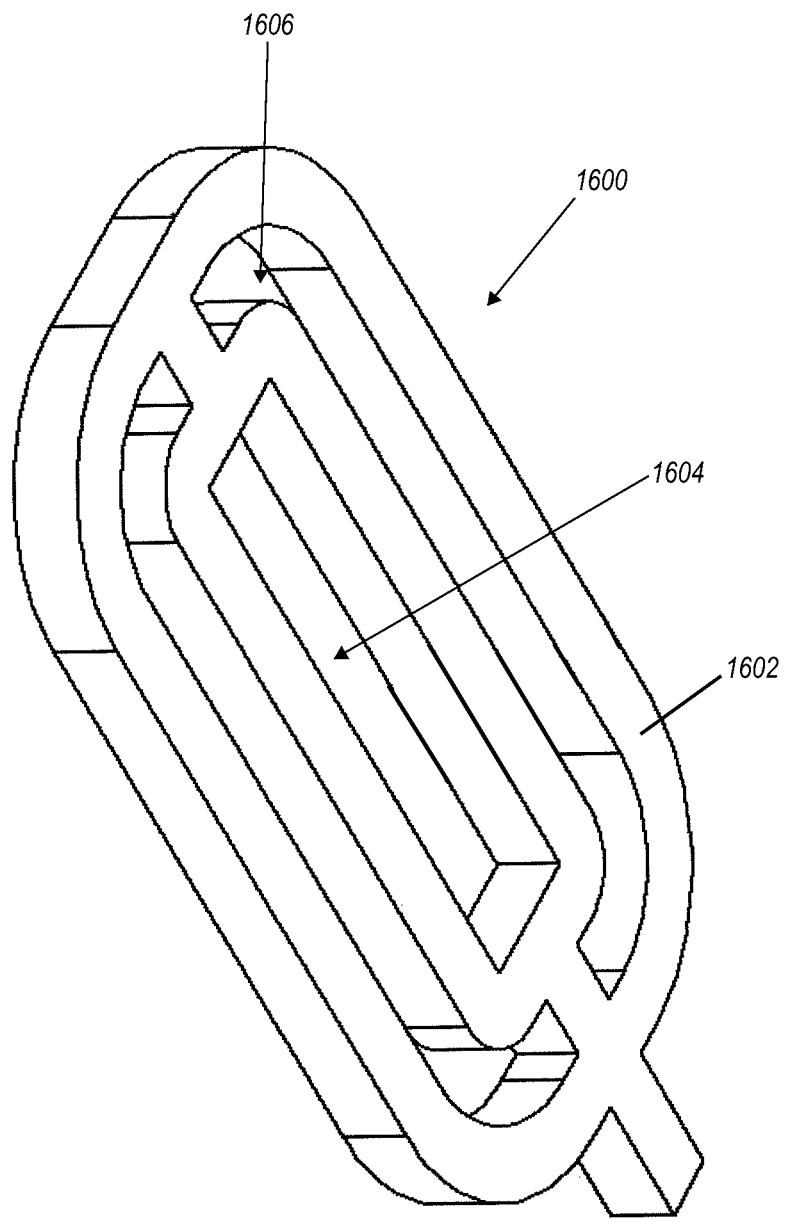
FIG. 16A is a perspective view of a variation of a component of a support that is implantable within Schlemm's canal.
Figure 16B:
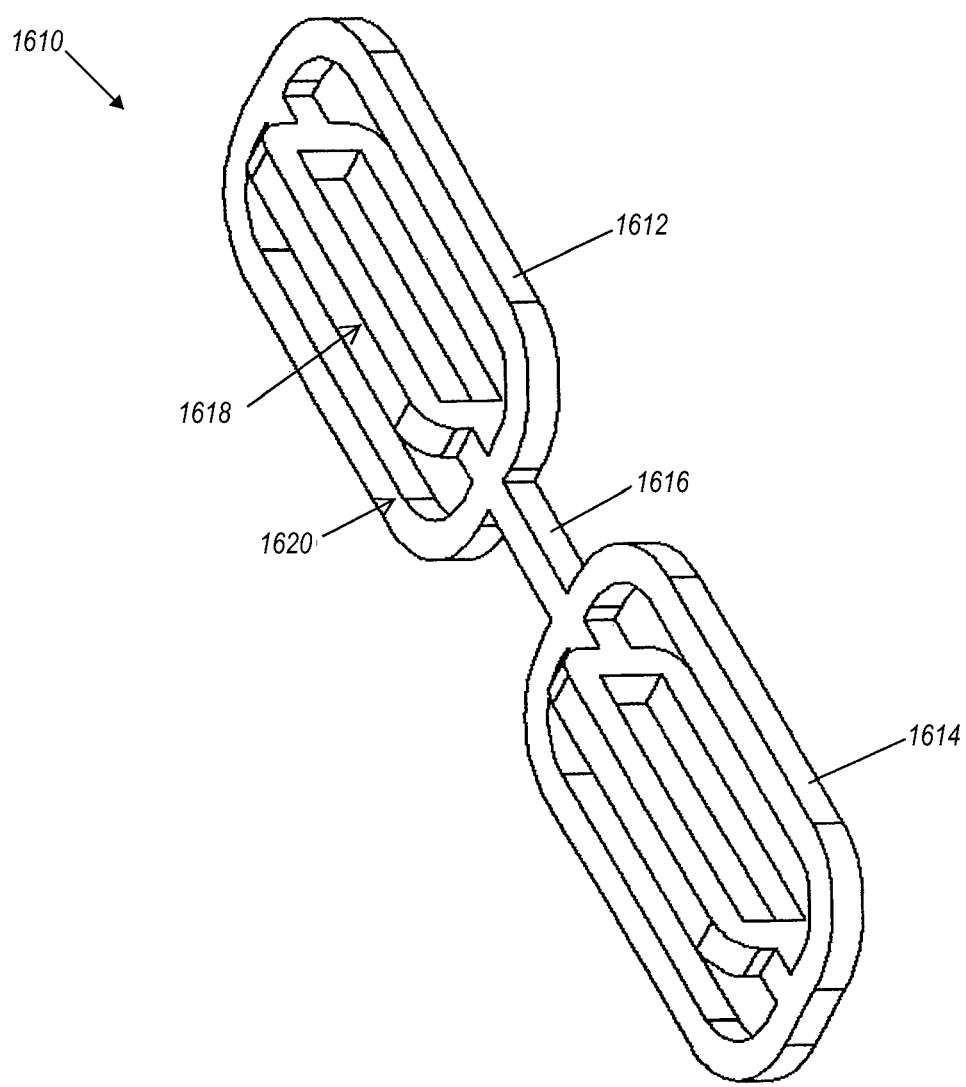
FIG. 16B is a perspective view of a variation of a support that is implantable within Schlemm's canal.

Any appropriate support components may be used. For example, FIG. 16A shows a support component 1600 comprising a body 1602 having various cut-outs (e.g., 1604 and 1606) that may be formed using, for example, a molding or machining process, such as a laser machining process. Component 1600 may, for example, form the entirety of a support, or may be coupled to, or integrally formed with, one or more identical components and/or one or more different components, to form a support. In some variations, and as discussed above, various portions of a support may lie along different planes. As an example, FIG. 16B shows a support 1610 comprising identical components 1612 and 1614 integrally coupled to each other by a connector 1616, where each component comprises portions lying along different planes (such as portions 1618 and 1620 of component 1612).

Figure 17A:
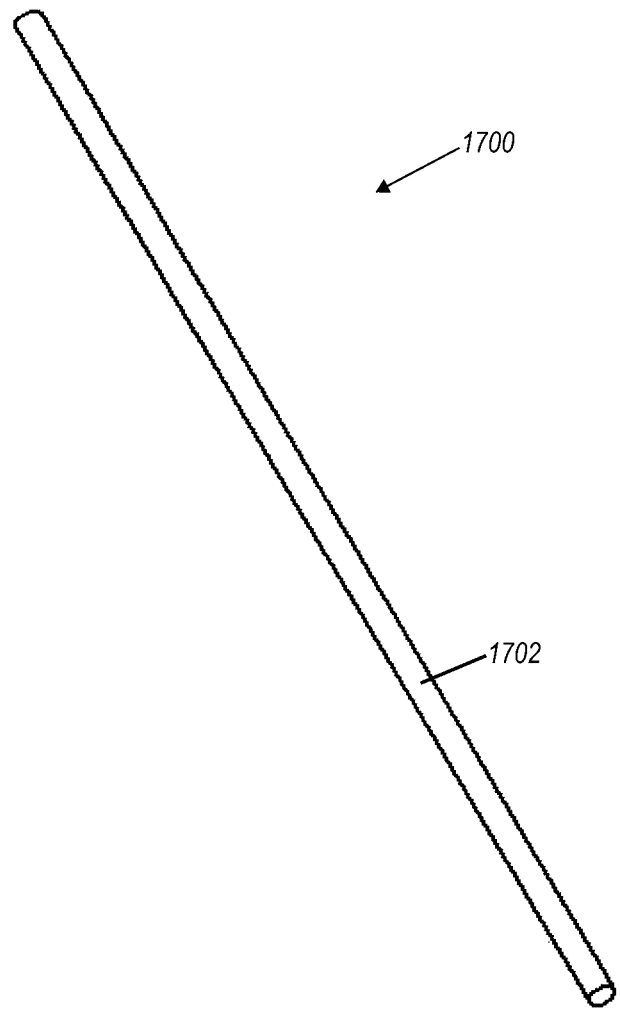
FIGS. 17A-17E are illustrative depictions of variations of supports that are implantable within Schlemm's canal.

In some variations, a support may comprise at least one elongated member. The elongated member may be straight, curved, bent, etc. In certain variations, the elongated member may be delivered into Schlemm's canal in a first configuration (e.g., straight), and then may assume a second configuration (e.g., curved, helical, double helical, etc.) during and/or after being initially positioned within at least a portion of the canal. For example, FIG. 17A shows a support 1700 comprising an elongated member 1702 in a straight configuration. Elongated member 1702 may be formed of, for example, a single wire. Because Schlemm's canal is relatively small in diameter (e.g., around 150-200 micrometers), it may be beneficial for a support to be formed of a small wire or wires.

In some variations, a support may be formed of a straight or curved wire that is inserted into the canal and that passively follows the path of the canal. Alternatively, a support may be inserted into the canal as a straight wire, and may then remodel to dilate the canal and restore patency, or to distend the canal so that it has a different radius of curvature. In certain variations, a support may be inserted into a canal as a curved wire, and may then remodel to dilate the canal and restore patency, or to distend the canal so that it has a different radius of curvature. The same effects as described above may be achieved in some variations with a support comprising multiple wires that may or may not be connected with each other or integral or unitary. In some variations, a support may be inserted into a canal and may dilate the canal without remodeling. For example, a support may be pushed into the canal to dilate the canal.

In certain variations, a support may be in the form of a continuous wire that props open Schlemm's canal or distends the trabecular meshwork on its own. Alternatively, a support may comprise a core comprising a continuous wire, as well as one or more additional wires and/or other features stemming from the core, where the additional wire(s) and/or other features prop open the canal or distend the trabecular meshwork. For example, a support may comprise one or more components or elements having the shape of a whisk. In certain variations, a support may comprise a discontinuous wire comprising stretches of a core element periodically interrupted by non-core elements that dilate Schlemm's canal or distend the trabecular meshwork. For example, a support may comprise a series of core wire elements alternating with a series of ring elements. It should be understood that in any variations of supports comprising wire cores, the wire core may be fenestrated and/or otherwise modified.

A wire or other support component may have a cross-section of any appropriate size and shape. For example, the cross-section of a wire or other support component may be circular, ovoid, planar, square, triangular with arced edges, or may have any other suitable shape. Moreover, a wire or other support component may comprise a smooth and continuous surface, a smooth and discontinuous surface (e.g., having different diameters along its length, different shapes along its length, such as a wire having a circular cross-section that turns planar in certain segments, or having symmetrical or asymmetrical shapes, curves, and/or diameters), or a surface that is not smooth. In variations in which the surface is not smooth, the wire or other support component may, for example, have continuously fluted edges or multiple edges (e.g., one, two, or three edges) that are parallel along the wire or component, discontinuously fluted edges that are parallel along the wire or component, continuously fluted edges that are perpendicular to the wire or component, discontinuously fluted edges that are perpendicular to the wire or component, continuously fluted edges that are swirled or angled along the wire or component, or discontinuously fluted edges that are swirled or angled along the wire or component. The periphery of the fluted edges may be bluntly serrated or undulating in some variations. Additionally, in certain variations a support may comprise fins that are both fluted and fenestrated.

In variations in which wires are used, the wires may have any appropriate dimensions. For example, a wire may have a diameter of up to about 500 micrometers (e.g., up to about 400 micrometers, up to about 300 micrometers, up to about 200 micrometers, up to about 100 micrometers, up to about 50 micrometers, up to about 25 micrometers, up to about 10 micrometers). The wire may alternatively or additionally have a diameter of at least about 10 micrometers (e.g., at least about 25 micrometers, at least about 50 micrometers, at least about 100 micrometers, at least about 200 micrometers, at least about 300 micrometers, at least about 400 micrometers). In certain variations, a wire may have a relatively thick diameter and may comprise fenestrations at any appropriate location (e.g., at its core, along its edges, or both).

Figure 17B:
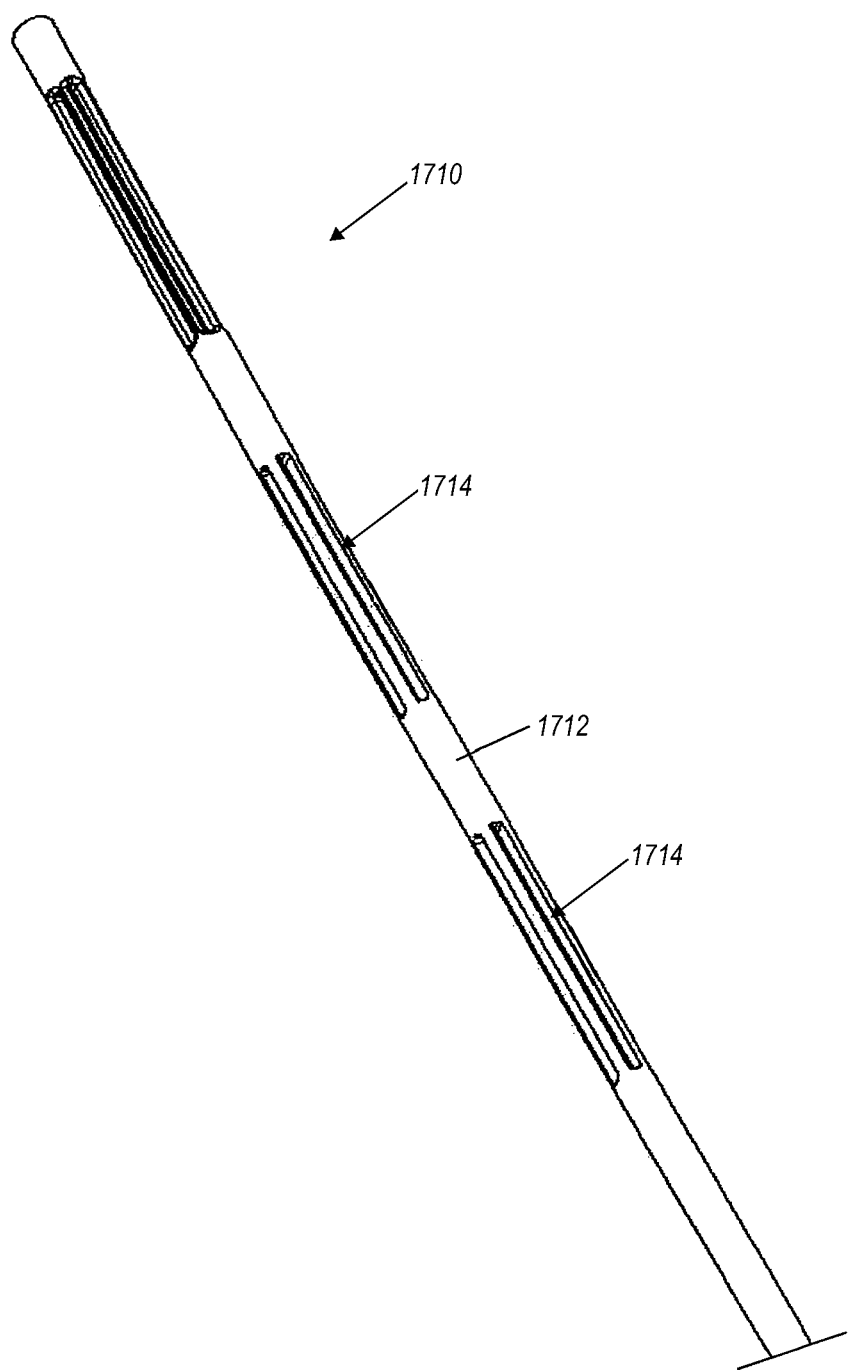
Figure 17C:
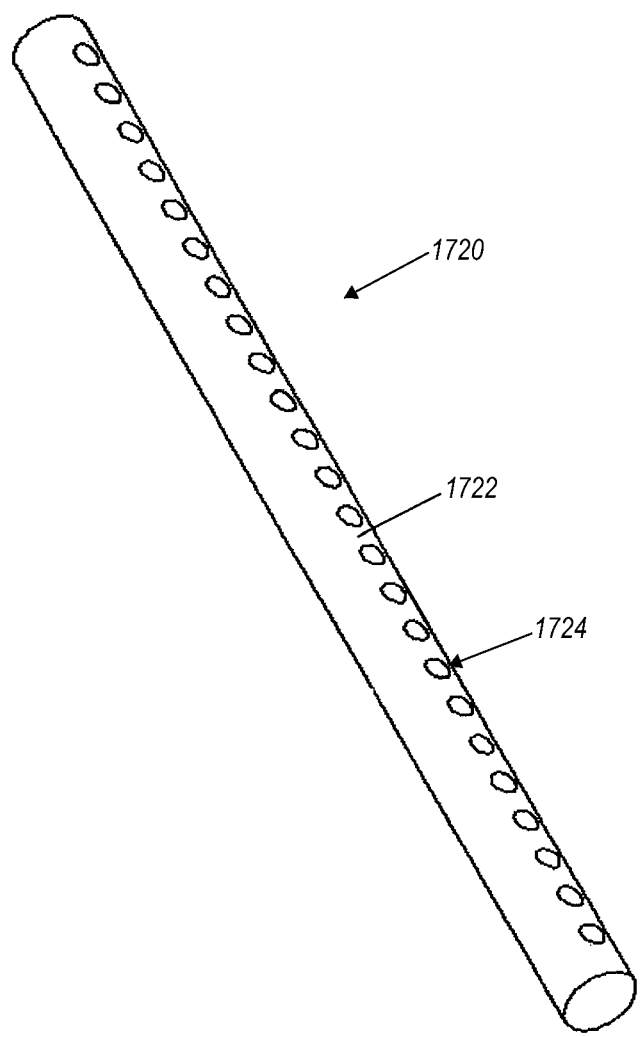

In some variations, an elongated member may comprise one or more surface features or other modifications that may, for example, allow for enhanced transmural and transluminal flow when the support is positioned within the canal. As an example, FIG. 17B shows a support 1710 comprising an elongated member 1712 having multiple fenestrations 1714. While fenestrations 1714 have the same size and shape and are evenly spaced relative to each other, some variations of supports may comprise one or more fenestrations and/or other features having different sizes and/or shapes, and/or that are not evenly spaced. FIG. 17C depicts a support 1720 comprising an elongated member 1722 having multiple apertures 1724 formed therein. Elongated members and portions thereof may be solid, tubular, or porous, or may have any other appropriate configurations. In certain variations, an elongated member may comprise at least one solid portion, at least one tubular portion, and/or at least one porous portion.

Figure 17D:
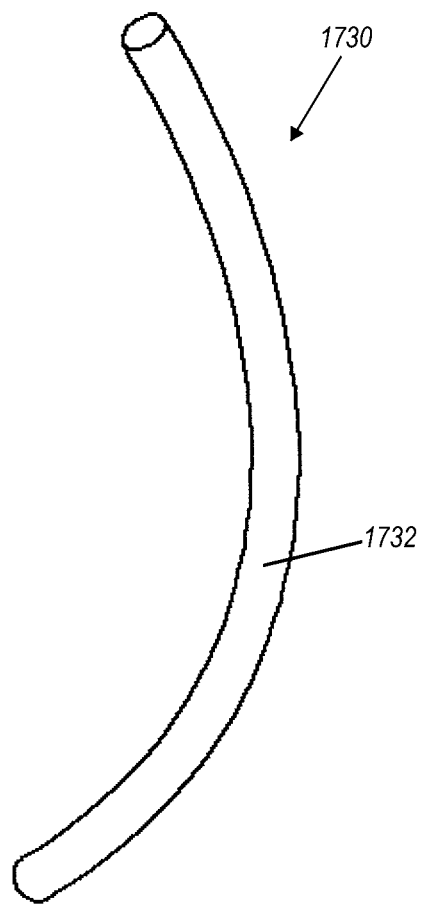
Figure 17E:
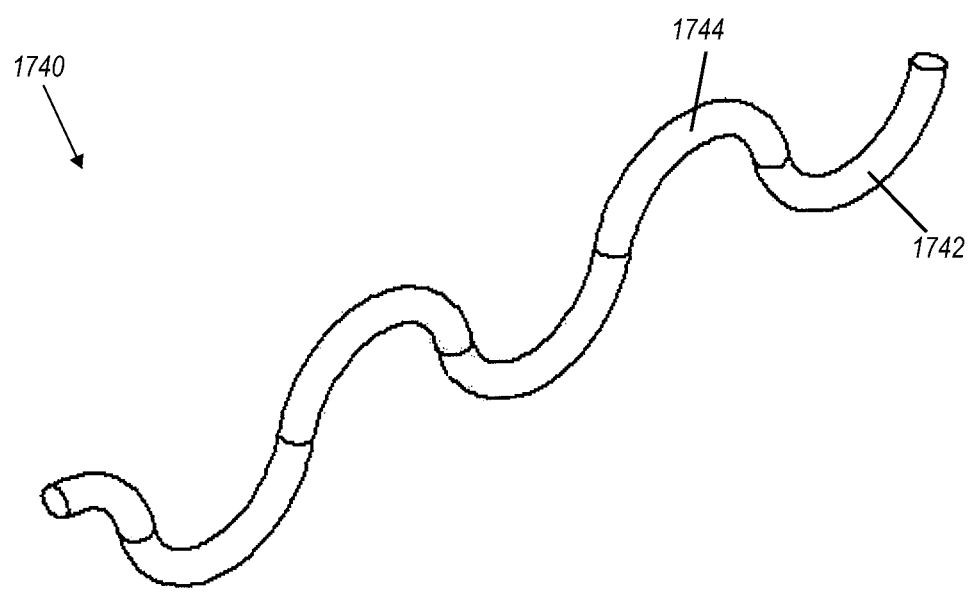
Figure 18:
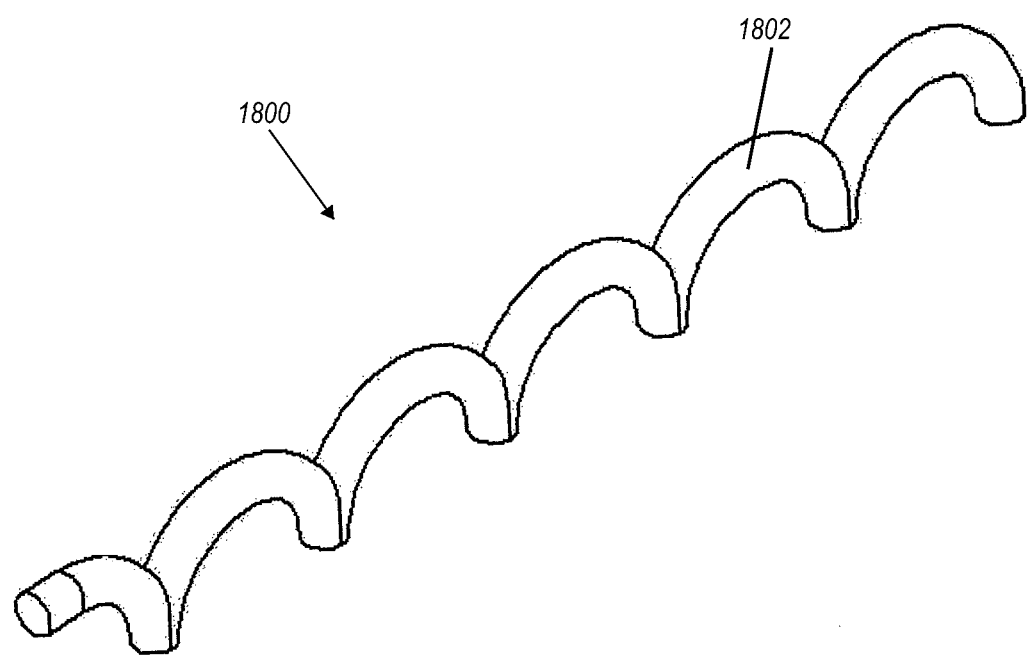
FIG. 18 is an illustrative view of another variation of a support that is implantable within Schlemm's canal.

As discussed above, in some variations a support may comprise a curved elongated member. The elongated member may have just one curve or may have multiple curves. As an example, FIG. 17D shows a support 1730 comprising a curved elongated member 1732. As shown there, elongated member 1732 has just one broad curve. However, FIG. 17E shows a support 1740 comprising multiple curved members (e.g., curved members 1742 and 1744) that are coupled to each other (e.g., via welding, adhesive, etc.). Of course, while curved members 1742 and 1744 are coupled to each other, in certain variations a support may alternatively or additionally comprise multiple curved portions that are integral with each other. For example, a support may comprise a single Nitinol wire shaped into a sinusoidal curve. The curved portions of a support may lie along the same plane, as shown in FIG. 17E, or along different planes. Moreover, some supports may comprise multiple curves, with some or all of the curves lying along the same plane, or some or all of the curves lying along different planes. Support 1740 essentially has a sinusoidal configuration, although other suitable configurations including multiple curves may also be used. As an example, FIG. 18 shows a support 1800 comprising multiple coupled or integral arcs or arches, such as arch 1802. The arches all lie along the same plane, but other variations of supports may comprise arches that lie along different planes. Moreover, arches or arcs may or may not be identical in size, radius of curvature, etc.

Other appropriate shapes and configurations may be used for supports that are implantable into at least a portion of Schlemm's canal. In some variations, helical configurations may be used. The configurations may comprise just one helical shape, or may comprise multiple helical shapes, such as a double helix. The helical shapes may just tangentially touch the interior surface of Schlemm's canal when disposed within the canal. In this way, they may provide sufficient support to restore or maintain at least partial patency of at least a portion of the canal, while also avoiding substantially interfering with transmural and transluminal flow across the canal. As a result, the canal's natural drainage passageways may be restored.

Figure 19A:
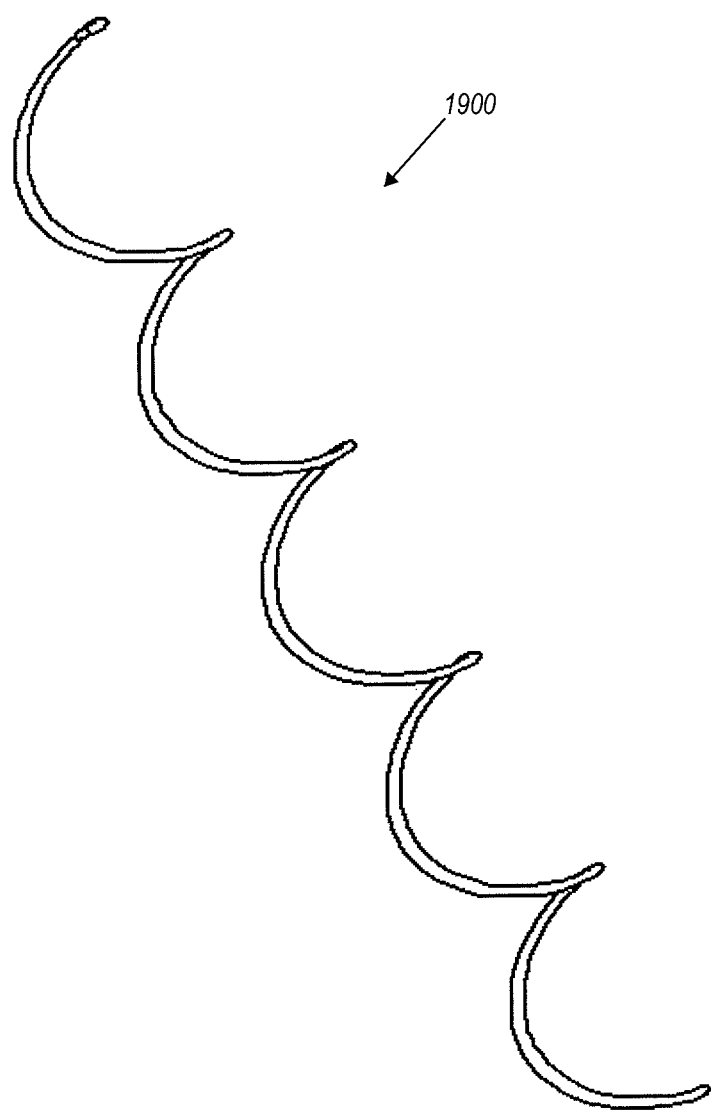
FIGS. 19A-19D depict variations of helical supports that are implantable within Schlemm's canal.
Figure 19B:
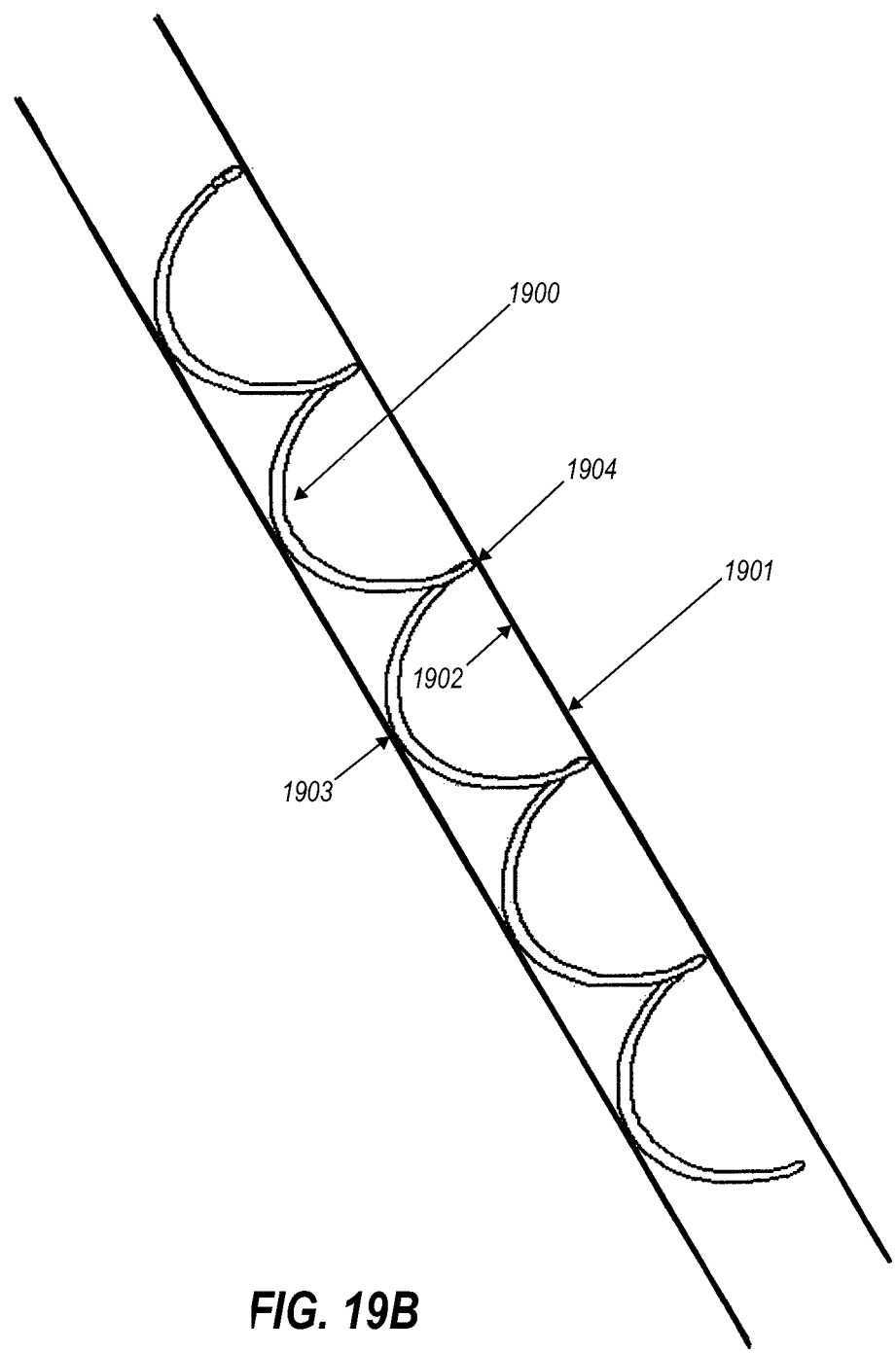
Figure 19C:
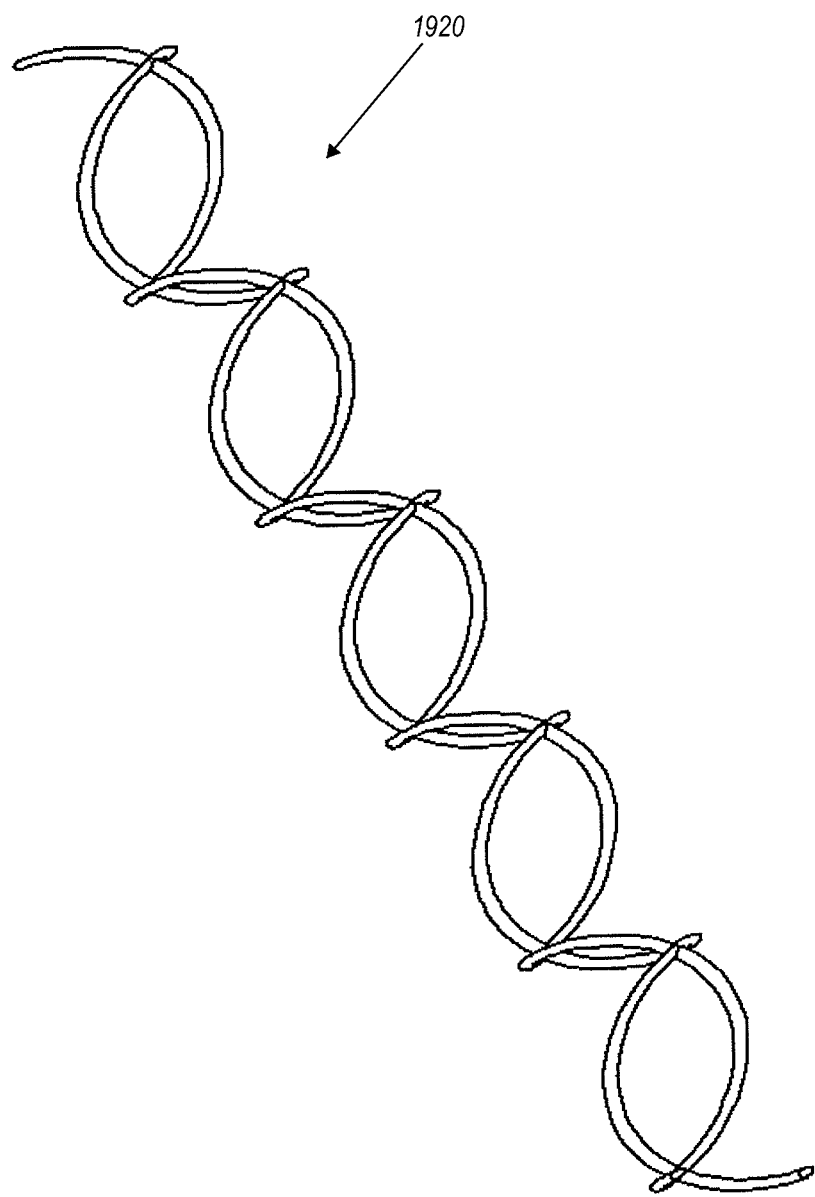
Figure 19D:
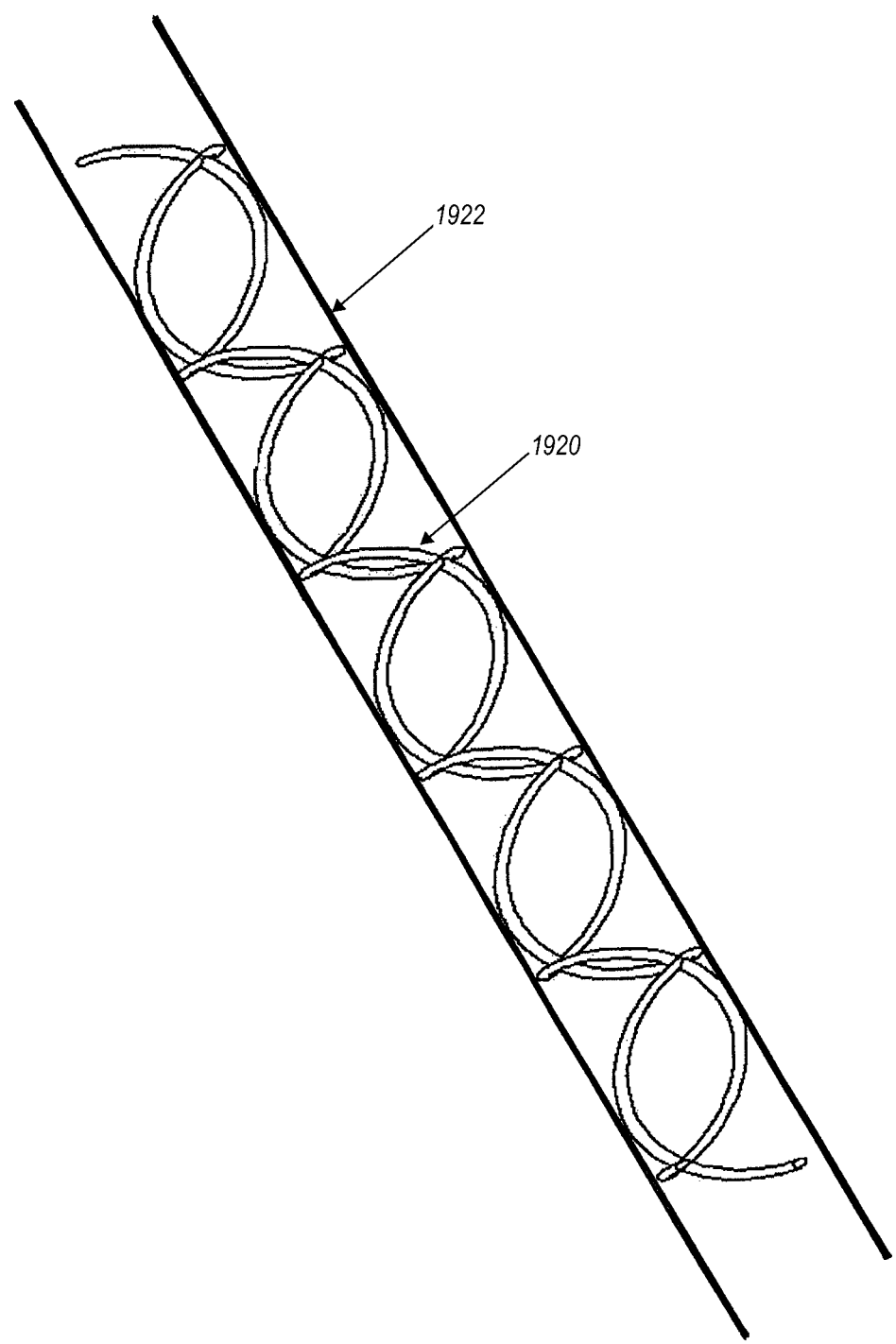

FIG. 19A shows an exemplary support having a helical configuration. As shown there, a support 1900 is in the form of a single helix. FIG. 19B shows support 1900 within Schlemm's canal 1901, where the support only tangentially touches the interior surface 1902 of the canal (e.g., at points 1903 and 1904). Of course, as discussed above, other helical configurations may alternatively or additionally be used within Schlemm's canal. As an example, FIG. 19C depicts a support 1920 in the form of a double helix, and FIG. 19D shows support 1920 disposed within Schlemm's canal 1922. Helices may in some cases have struts and/or other connectors therebetween. For example, a double helix may comprise first and second helices that are connected to each other by struts extending between them.

Supports having helical configurations, as well as other variations of supports described here, may be capable of restoring or maintaining at least partial patency of at least a portion of Schlemm's canal (e.g., the entirety of the canal) with minimal tangential touch. For example, a support, when at least partially disposed within the canal, may contact the interior surface of the canal only at tangent points. Additionally, the majority of a support may occupy the central core of Schlemm's canal, rather than the very periphery of the canal, and may avoid contacting the interior surface of the canal. As a result, the obstruction of aqueous flow at the valuable, porous inner and outer canal walls may be minimized or prevented. With restoration of canal patency and minimal wall obstruction, aqueous humor may again easily traverse the canal (e.g., in the case of a support having a helical configuration, through the open helical network).

In some variations, a support having a helical configuration, or another variation of a support described here, may be delivered at least partially into Schlemm's canal and expanded into its final configuration once the support is at least partially disposed within Schlemm's canal. Upon support delivery and expansion, dilation of the three primary and critical drainage structures may be restored: (1) juxtacanalicular tissue distension and pore dilation (inner wall), (2) dilation of Schlemm's canal, and (3) collector channel dilation (outer wall). Of course, such restoration may be achieved with other supports and/or delivery and positioning mechanisms described here, as well. With minimal wall obstruction, aqueous humor may again easily traverse the dilated canal lumen and walls through the open helical network.

In certain variations, a support may comprise multiple rings that are coupled to each other or integral with each other.

Figure 20A:
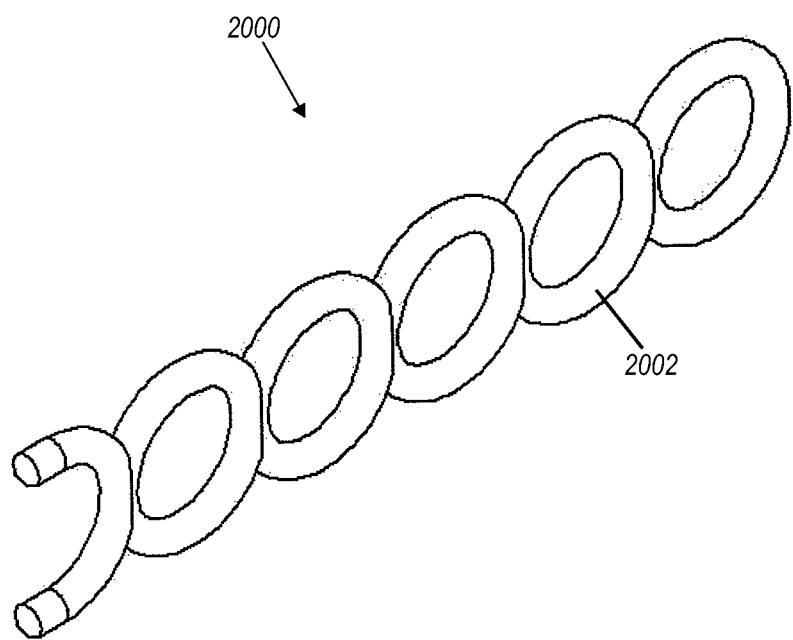
FIGS. 20A and 20B are illustrative depictions of variations of supports that comprise rings and that are implantable within Schlemm's canal.
Figure 20B:
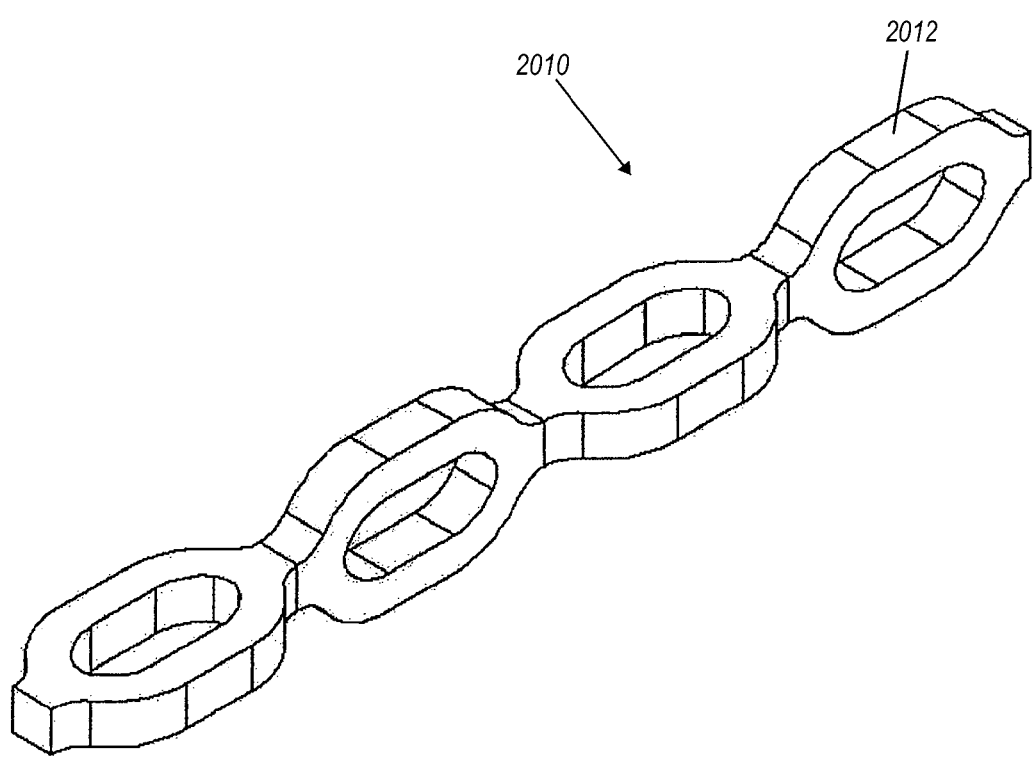

For example, FIG. 20A shows a support 2000 comprising multiple rings, such as ring 2002, all lying along the same plane. While the rings all have the same size, some variations of supports may comprise multiple rings having different sizes. Moreover, rings may have different shapes. For example, some rings may be rounded and circular, while other rings are oval and have somewhat beveled edges. Furthermore, some variations of supports may comprise rings that do not lie along the same plane. As an example, FIG. 20B shows a support 2010 comprising multiple rings, such as ring 2012, that are coupled to each other, where adjacent rings are positioned at a 90° angle with respect to each other.

Figure 21:
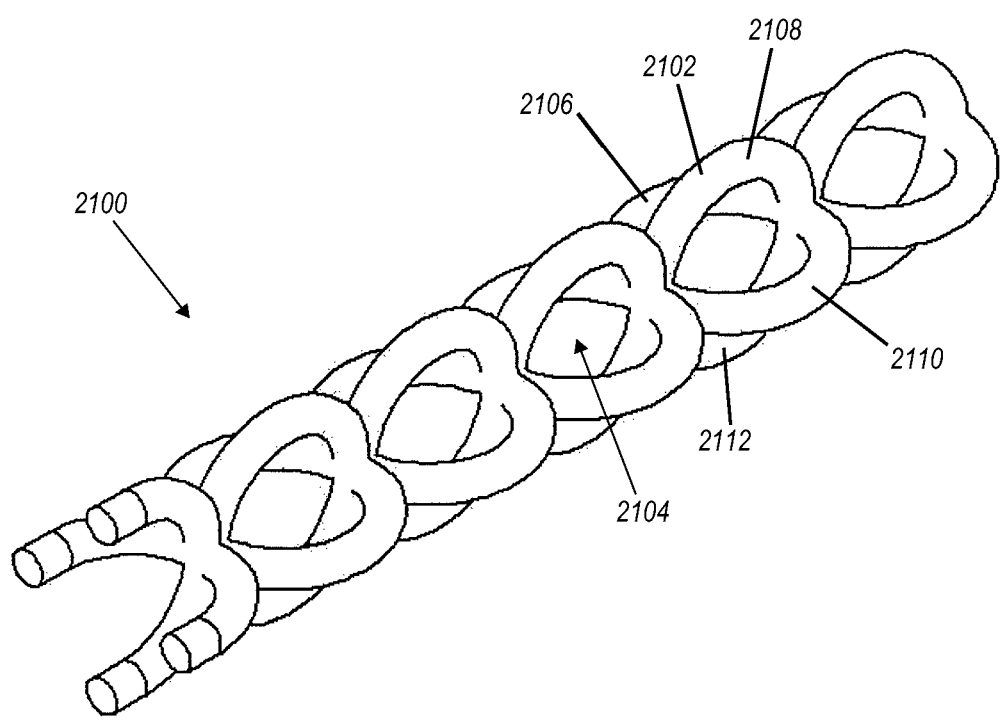
FIG. 21 depicts a variation of a support that is implantable within Schlemm's canal.

Still further variations of supports may be used. For example, FIG. 21 shows a support 2100 comprising multiple coupled components, such as component 2102, having a shape similar to an egg beater or whisk, with a central opening 2104. While each component comprises four curved portions (such as curved portions 2106, 2108, 2110 and 2112 of component 2102), other variations of supports may comprise components having a similar shape, but a different number of curved portions.

Figure 22A:
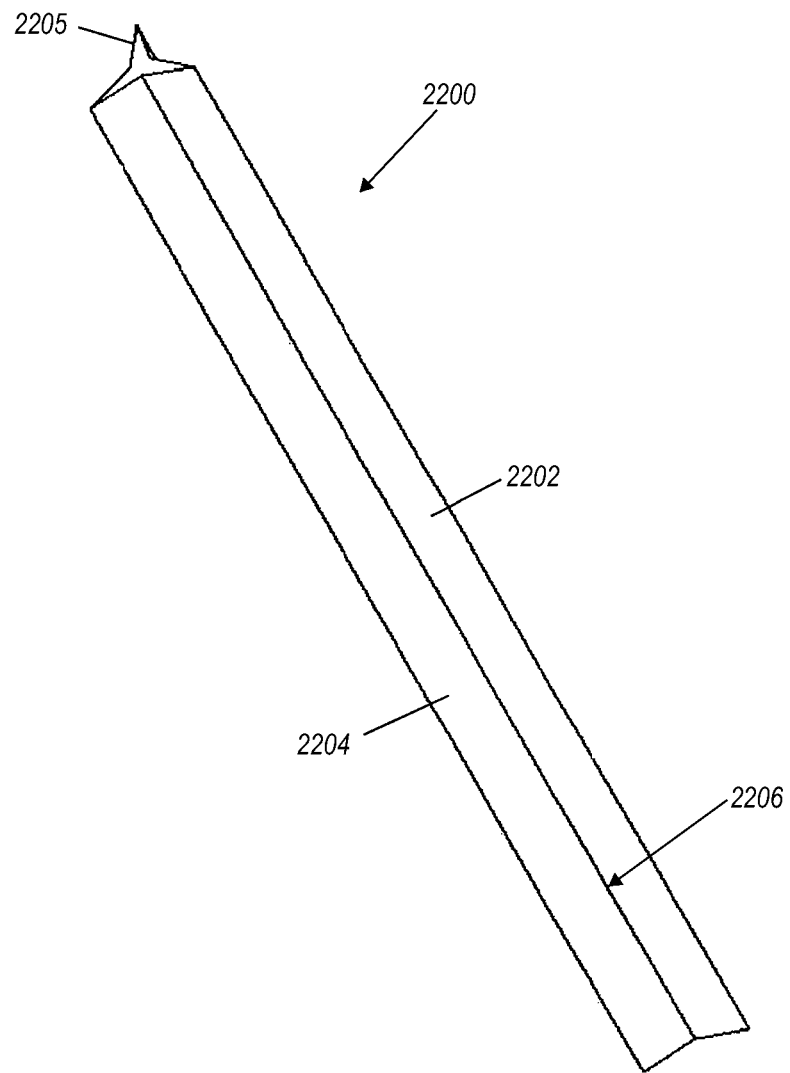
FIGS. 22A-22E show different variations of supports that are implantable within Schlemm's canal.

In some variations, a support may comprise one or more edges that are configured to contact the interior surface of Schlemm's canal during use. For example, FIG. 22A shows a support 2200 comprising three integral elongated members 2202, 2204 and 2205. The adjacent elongated members come together at a junction, such as junction 2206 between adjacent elongated members 2202 and 2204. When support 2200 is disposed within Schlemm's canal, the majority of the support may be located within the central core of the canal, with the edges of the support tangentially touching the interior surface of the canal.

Figure 22B:
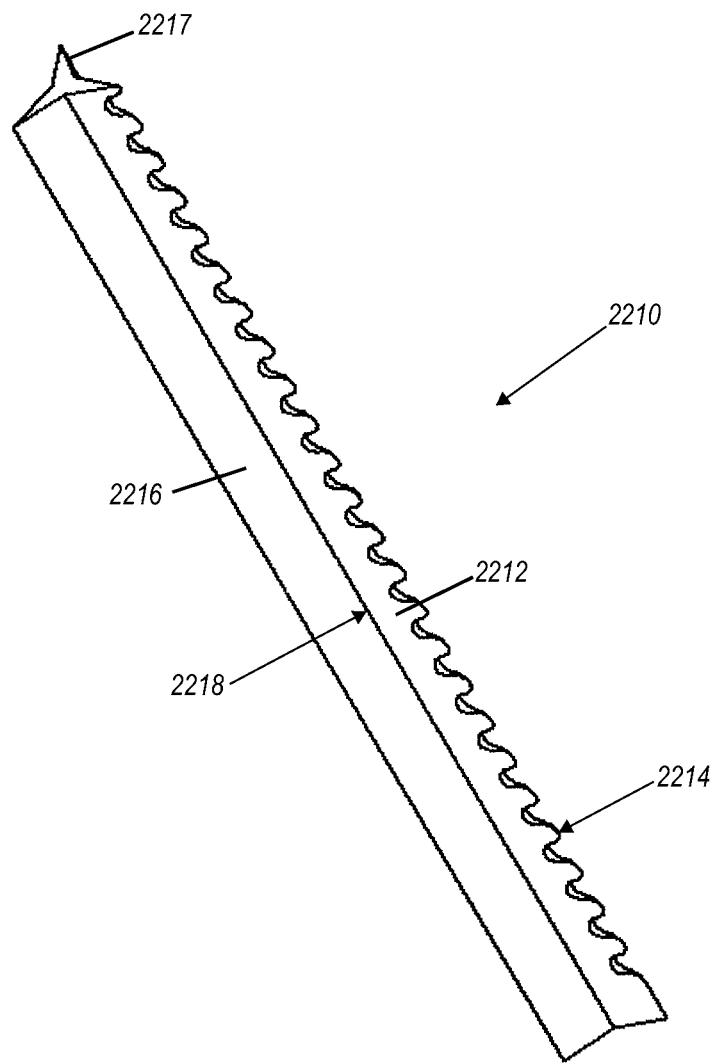

Of course, the edges of a support need not necessarily be linear. For example, FIG. 22B shows a support 2210 comprising three integral elongated members 2212, 2216 and 2217, where adjacent elongated members come together at a junction, such as junction 2218 between adjacent elongated members 2212 and 2216. As shown in FIG. 22B, elongated member 2212 has a curvy edge 2214. Such an edge may, for example, have relatively little contact with the interior surface of Schlemm's canal, while still having sufficient contact to help restore or maintain at least partial patency of at least a portion of the canal.

Figure 22C:
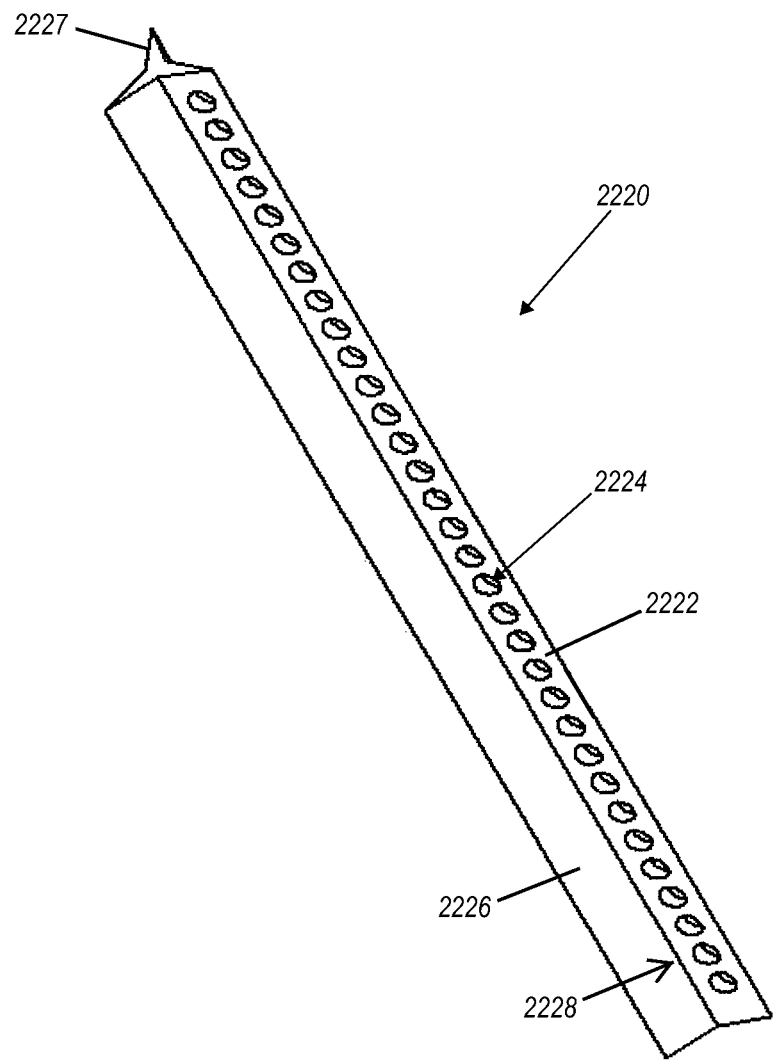
Figure 22D:
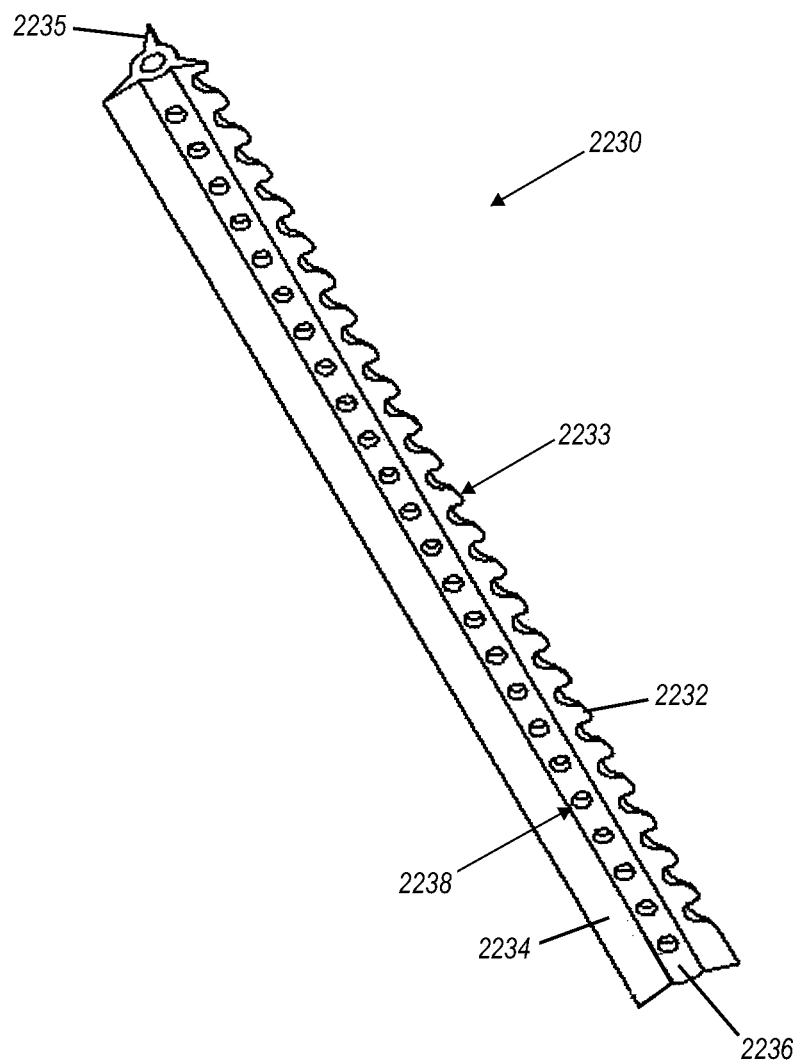

The different portions of a support may also comprise one or more modifications, such as apertures, fenestrations, pores, etc. For example, FIG. 22C shows a support 2220 comprising three integral elongated members 2222, 2226 and 2227, where adjacent elongated members come together at a junction, such as junction 2228 between adjacent elongated members 2222 and 2226. As shown in FIG. 22C, elongated member 2222 comprises multiple apertures 2224. While the apertures are all depicted as having the same general size and shape, other variations of supports may comprise apertures having different sizes and/or shapes. Moreover, some variations of supports may comprise combinations of one or more of the above-described features, as well as any other appropriate features. For example, FIG. 22D shows a support 2230 comprising a central tubular member 2236 and three integral elongated members 2232, 2234 and 2235 radiating from the central tubular member. Integral elongated member 2232 has a curvy edge 2233, while central tubular member 2236 comprises multiple apertures 2238. Central tubular member 2236 may be in the form of, for example, a wire having a lumen therethrough. Of course, while support 2230 comprises a single central tubular member, in some variations, a support may alternatively comprise multiple tubular members, or may alternatively or additionally comprise at least one non-tubular elongated member, such as a central non-tubular elongated member (e.g., a central solid wire). The tubular members or non-tubular elongated members may or may not comprise one or more features, such as apertures, fenestrations, or the like.

While the above-described supports comprise three integral elongated members, it should be understood that supports may comprise any suitable number of elongated members and/or other components. For example, a support may comprise two elongated members and/or other components, or may comprise more than three elongated members and/or other components. The elongated members and/or other components may also have any number of edges. Moreover, at least some of the elongated members and/or other components may not be integral with each other. For example, at least two of the elongated members may be coupled (e.g., welded, adhesive-bonded, etc.) to each other. Additionally, any number of elongated members and/or other components in a support (e.g., all of the elongated members and other components) may comprise features such as fluted edges, curvy edges, fenestrations, apertures, pores, or the like, or any combination thereof. For example, in some variations, a support may comprise four elongated members, where each elongated member has fluted edges and/or fenestrations. A support may also include elongated members and/or other components having different features from each other.

Figure 22E:
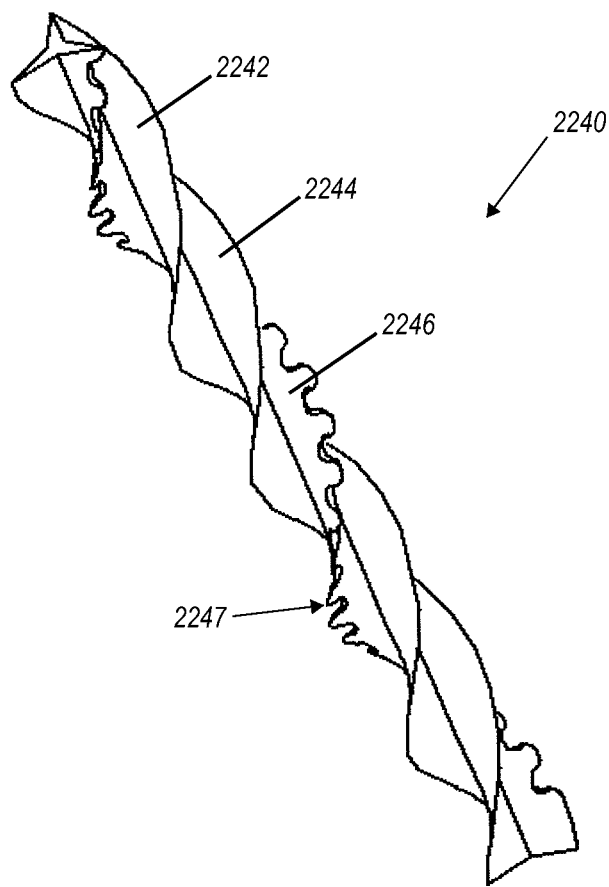

In certain variations, a support may comprise one or more twisted or otherwise non-linear portions. For example, FIG. 22E shows a support 2240 comprising three portions 2242, 2244 and 2246 that are twisted relative to each other, such that they form a somewhat helical configuration. It should be noted that any other support configurations shown herein may be twisted upon final assembly, as appropriate. As shown, the portions may at least partially comprise straight edges, and/or may at least partially comprise edges that are not straight, such as curvy edge 2247 of portion 2246.

Supports described here may have any suitable dimensions. For example, in some cases a single support may have a length (when curved, an arc length) of 10 millimeters. The dimensions of a support, such as its length, may depend on clinical need. For example, some patients (e.g., more severe glaucoma patients) may require multiple supports or longer supports for greater outflow restoration. It should be noted that multiple supports may be implanted simultaneously or at different times. In some variations, multiple supports may be used in a procedure, because it may be easier to insert multiple smaller supports rather than one longer support. As an example, in some variations, two supports that each have a length of 10 millimeters may be inserted into Schlemm's canal. Alternatively, in certain variations, one longer support may be used. In some cases, a single support may be used along the entire circumference of Schlemm's canal.

A support, such as a support comprising one or more wires, may comprise any of a variety of different materials. In general, a support may comprise one or more biocompatible materials, such as biocompatible polymers or plastics, polymer composites, ceramics or ceramic composites, glass or glass composites, metals, alloys (e.g., shape-memory alloys, superelastic alloys) or combinations or derivatives of these materials. Examples of biocompatible metals and metal alloys include stainless steel, gold, silver, titanium, tantalum, platinum and alloys thereof, cobalt and chromium alloys, and nickel-titanium alloys such as Nitinol. Examples of biocompatible polymers include high density polyethylene (HDPE), polyurethane, polycarbonate, polypropylene, polymethylmethacrylate (PMMA), polybutylmethacrylate, polyesters, polytetrafluoroethylene (PTFE), silicone, acrylic polymers, polyvinyl alcohol, polyvinyl pyrrolidone, polyvinyl chloride, ethyl vinyl acetate, collagen, collagen derivatives, flexible fused silica, polyolefins, NYLON® polymers, polyimide, polyacrylamide, fluorinated elastomers, and copolymers and blends thereof. In addition, biocompatible hydrogels may be used in supports and devices described herein. As discussed in more detail below, biocompatible polymers may be biodegradable. In some variations, a component of a support, such as a wire, may comprise one or more hydrophilic materials, such as those that are used in contact lenses. The hydrophilic material(s), when incorporated into the support, may be capable of restoring or maintaining at least partial patency of Schlemm's canal and/or distending the trabecular meshwork, absorbing aqueous humor, and/or transferring aqueous humor out of Schlemm's canal. A support may be made of a single material or a combination of materials. In some variations, a support made from a first material may be coated with a second material (e.g., to enhance or improve its biocompatibility).

In some examples, a support may comprise one or more biodegradable polymers. Examples of suitable biodegradable polymers include collagen, a collagen derivative, a poly(lactide), a poly(glycolide), a poly(lactide-co-glycolide), a poly(lactic acid), a poly(glycolic acid), a poly(lactic acid-co-glycolic acid), a poly(lactide)/poly(ethylene glycol) copolymer, a poly(glycolide)/poly(ethylene glycol) copolymer, a poly(lactide-co-glycolide)/polyethylene glycol) copolymer, a poly(lactic acid)/poly(ethylene glycol) copolymer, a poly(glycolic acid)/poly(ethylene glycol) copolymer, a poly(lactic acid-co-glycolic acid)/poly(ethylene glycol) copolymer, a poly(caprolactone), a poly(caprolactone)poly(ethylene glycol) copolymer, a polyorthoester, a poly(phosphazene), a poly(hydroxybutyrate) or a copolymer including a poly(hdroxybutyrate), a poly(lactide-co-caprolactone), a polycarbonate, a poly(esteramide), a polyanhydride, a poly(dioxanone), a poly(alkylene alkylate), a copolymer of polyethylene glycol and a polyorthoester, a biodegradable polyurethane, a poly(amino acid), a polyetherester, a polyacetal, a polycyanoacrylate, a poly(oxyethylene)/poly(oxypropylene) copolymer, and blends and copolymers thereof.

At least a portion of a support may be made from a shape-memory material. For example, shape-memory alloys (e.g. a nickel-titanium alloy) may be used. In addition, shape-memory polymers (e.g., polymers made from copolymerizing monomers oligo(e-caprolactone) dimethacrylate and n-butyl acrylate or polymers based on styrene acrylate, cyanate ester and epoxies) may be used. In some variations in which a shape-memory material is used in the support, the support can have a compressed state prior to and during implantation, and an expanded state following implantation. The use of a compressed state support comprising a shape-memory material can allow for a smaller incision and facilitate insertion into a narrowed or compressed Schlemm's canal. Once implanted, the support may be expanded using any suitable method (e.g., thermally activated by body heat or an alternate heat source) to adopt an expanded state, thereby opening the canal.

The support may include one or more active agents, such as a pharmaceutical. For example, a support may comprise one or more materials that function as a depot for one or more active agents. Examples of such materials include those that have been tested in the eye for intraocular lenses, such as polymethylmethacrylate (PMMA), silicone polymers, hydrogels, acrylic polymers, metals (e.g., gold) and alloys (e.g., shape-memory alloys such as Nitinol, superelastic alloys, etc.). Exemplary active agents include prostaglandins, prostaglandin analogs, beta blockers, alpha-2 agonists, calcium channel blockers, carbonic anhydrase inhibitors, growth factors, such as tissue growth factors and vascular endothelial growth factors, anti-metabolites, chemotherapeutic agents such as mitomycin-C, 5-fluorouracil, steroids, non-steroidal anti-inflammatory agents, antagonists of growth factors such as antagonists of vascular endothelial growth factors, or combinations thereof. An active agent may be provided as a coating on at least a portion of a support. An active agent may be delivered throughout the eye by dissolution or other dispersal mechanisms. Alternatively, at least a portion of a support may be impregnated with an active agent. In some variations, an active agent may be dispersed within at least a portion of a support. For example, a cavity in the support may be filled with the active agent.

The delivery of an active agent may be controlled by time-release. For example, the portion of a support containing an active agent may include a time-release coating or time-release formulation designed to gradually dissipate the active agent over a certain period of time. Biodegradable coatings and formulations for time-release of active agents are known in the art. In certain variations, a support may comprise multiple layers, where the layers each comprise an active agent. For example, support layers can be used to release a series of different agents, or a series of doses of the same agent. Such layers may be part of a coating applied to a support, or part of a support body. In addition, a support may comprise one or more biodegradable layers that do not contain any active agent, and that may be applied or interspersed between other layers to further control delivery of active agents to the eye.

Figure 23:
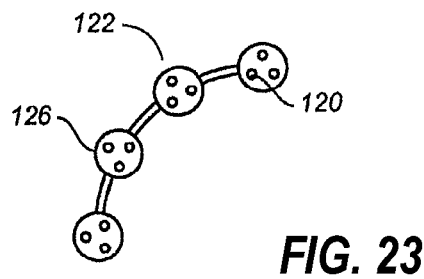
FIG. 23 shows an illustrative example of a support that may be modified using electromagnetic radiation.

In some variations, it may be desirable to change or alter a support using electromagnetic radiation. For example, at least a portion of a support may be fenestrated, perforated, bent, shaped or formed using a laser to enhance intraocular pressure reduction. As illustrated in FIG. 23, predetermined localized portions 120 of a support 122 may be designed to absorb light of a certain wavelength or wavelength range. Preferential absorption may be achieved by material selection and/or by doping with chromophores, for example. Upon irradiation with sufficient energy at the selected wavelength or wavelength range, the patterned regions 120 may ablate or melt, leaving new or enlarged perforations or indentations in the support. For example, a pulsed titanium sapphire laser operating between about 750 nm and about 800 nm may be used to ablate gold regions. If beads 126 in support 120 are hollow, then after irradiation and ablation, features 120 may become fenestrations. The fenestrations may be created to make support 122 more porous in nature and/or to allow release of an active agent from within a support (e.g., from within beads 126). Alternatively or additionally, it may be possible to use a mask in combination with electromagnetic radiation to alter a support, such as by patterning or machining. The modification of a support using electromagnetic radiation may be carried out prior to and/or subsequent to insertion.

In some variations, the visual appearance of a support may be enhanced under certain conditions to facilitate placement or to monitor the position and/or condition of the support. Visual enhancement can be achieved by incorporating into or onto the support chromophores that fluoresce or phosphoresce upon excitation with a light source. Chromophores may also assist a clinician in verifying the position of the support postoperatively using a gonioscope, for example. Light sources can include lasers, lamps, and light-emitting diodes. In some instances, transmission or absorption filters may be used to select the wavelength of the excitation source or to detect or view emission. Emission from a support capable of visual enhancement may be in the wavelength range of about 300 nm to about 800 nm. The chromophores may be an integral component of the material making up the support, doped into support material, or coated or sprayed onto the support. Visually-enhancing chromophores may be applied on a temporary basis, or on a permanent basis. An example of a suitable chromophore is fluorescein, which may be excited with any laser or lamp emitting at about 400 nm to about 500 nm. In addition, phosphorus-based chemiluminescent or photoluminescent pigments may be used, which may be selected to absorb at various wavelengths across the visible spectrum.

In some variations, the support may be capable of being attached to tissue. For example, the support may include a hook, loop, clip, extension, or the like that may be easily attached to tissue. The support may also be attached to tissue using sutures or adhesives. The support may be attached to tissue using more than one attachment method. For example, suturing may be used in combination with a loop, and/or an adhesive may be used in combination with a hook. In certain variations, a support may be allowed to self-position in Schlemm's canal. For example, a support, such as a helical or twisted support, may comprise one or more materials (e.g., shape-memory materials) that allow the support to be inserted into the canal in one configuration (e.g., substantially straight and elongated) and to adjust to reconfigure itself within the canal (e.g., into a helical or twisted configuration). In some variations, a support may be mobile within Schlemm's canal.

Kits

Kits for reducing intraocular pressure are provided, where the kits contain at least one support that may be implanted circumferentially within Schlemm's canal, and that may be configured to restore or maintain at least partial patency of at least a portion of Schlemm's canal. The support may occupy at least a portion of a central core of Schlemm's canal and/or may not substantially interfere with transmural or transluminal flow across the canal, and/or with longitudinal flow within the canal. The kits may also provide an introducer or delivery device for implanting the support in the canal. The support and introducer may be provided in a packaged combination in the kits. The kits may also include instructions for use (e.g., for implanting and inspecting the support).

An introducer may be inserted into the eye and may be capable of implanting a support at the desired implantation position within Schlemm's canal. For example, an introducer may include a tubular cannula through which a support may be passed. In addition to a cannula, an introducer may include a tubular or solid pusher rod that may be used to push or advance the support into and/or around Schlemm's canal. Alternatively, a pusher rod or plunger may be used without a cannula to introduce a support into the canal. A support may be installed into the lumen of a cannula prior to insertion, the distal end of the cannula positioned at or near the desired support location, and the pusher rod operated from the proximal end to push the support distally out of the distal end of the cannula and into the canal. The cannula and/or pusher rod may be flexible and small enough in diameter to extend at least partially around the canal. In some variations, a proximal end of a suture may be introduced into the canal via a cannula and the suture extended circumferentially around the canal. A distal portion of the suture may be connected to the support and force applied to the proximal end of the suture to pull the support into the canal. The support may then be positioned within the canal by pulling the suture in a distal or proximal direction. The suture may be used to anchor the support within the canal. In other variations, the support may be directly introduced into the canal using surgical forceps, or the like.

Figure 24A:
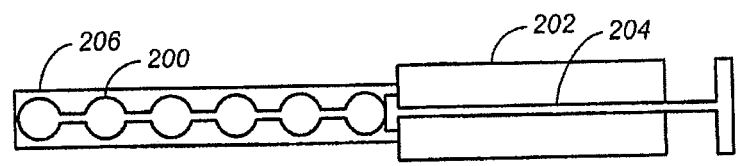
FIG. 24A illustrates a syringe that may be used to insert a support into Schlemm's canal.
Figure 24B:
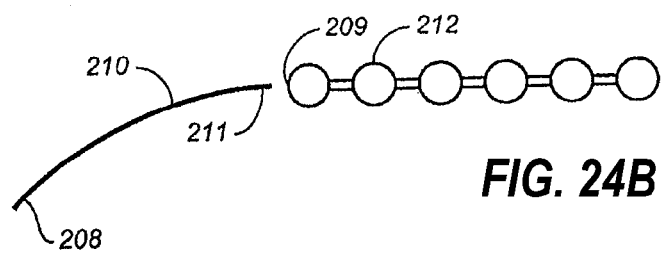
FIG. 24B illustrates a variation in which a support is threaded onto a guide element for insertion and positioning in Schlemm's canal.
Figure 24C:
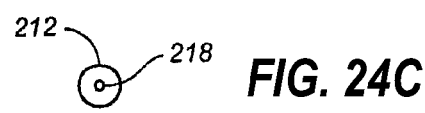
FIG. 24C illustrates a cross-sectional view of a support having a central bore to accommodate a guide element.
Figure 24D:
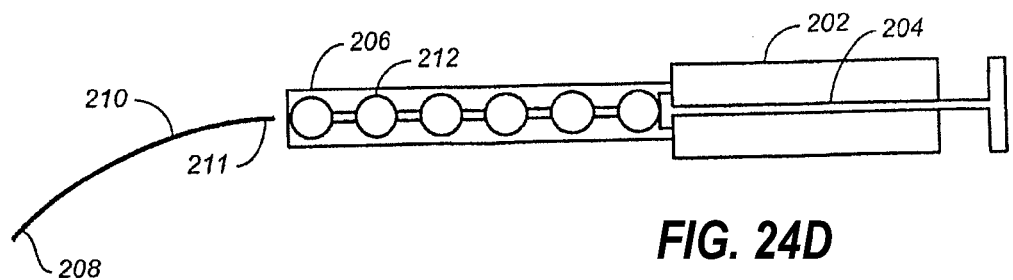
FIG. 24D illustrates a variation in which a syringe and a guide element are used for insertion and positioning of a support in Schlemm's canal.

FIGS. 24A-24D illustrate additional variations for introducing a support into Schlemm's canal. As shown in FIG. 24A, a support 200 may be introduced into the canal using a syringe 202 and a plunger 204. Syringe 202 has a distal end 206 that may be at least partially inserted into or placed adjacent to an opening in the canal. Force in a distal direction may be applied to plunger 204, thereby pushing support 200 into the canal. Referring to FIGS. 24B and 24C, distal end 208 of guide element 210 may be at least partially introduced into the canal. Guide element 210 may comprise a guidewire. Guide element 210 may be extended circumferentially along the canal to aid in positioning the support. Support 212 comprises central bore 218 capable of accommodating guide element 210 such that support 212 can be threaded onto guide element 210 and slidably positioned along the guide element. Once distal end 209 of support 212 is threaded onto guide element 210, support 212 may be pushed in a distal direction along guide element 210 to insert support 212 into the canal. In some variations, support 212 may remain threaded onto guide element 210, and guide element 210 may remain in the canal. In other variations, support 212 may be slid off distal end 208 of guide element 210, and the guide element may be pulled in a proximal direction for removal. Referring to FIGS. 24C and 24D, syringe 202 with plunger 204 may be used in combination with a guide element 210. In this variation, distal end 208 of guide element 210 may be inserted at least partially into Schlemm's canal. Guide element 210 may be extended circumferentially along the canal to aid in positioning the support. Support 212 has central bore 218 capable of accommodating guide element 210. Proximal end 211 of guide element 210 may be inserted into bore 218. Plunger 204 may be depressed in a distal direction to push support 212 into the canal and slide support 212 along element 210. Guide element 210 may remain in the canal or may be removed following insertion of the support. Supports 200 and 212 may be sufficiently resilient to withstand force encountered as they are pushed into the canal.

In some variations, a positioning device may be used with the introducer to position or adjust the support within the canal. A positioning device may include a rod, grippers, a clamp, a hook, or the like. In certain variations, a device or system capable of dilating the canal to facilitate insertion of a support may be included in the kits (e.g., a syringe or other device capable of injecting fluid into the canal).

In some variations, the kits may contain at least two supports. Multiple supports may be implanted within one eye or within multiple eyes. If the kits contain multiple supports, the kits may also contain multiple introducers. Alternatively, the same introducer may be used for implantation of multiple supports, especially if the multiple supports are being delivered to a single eye. If multiple supports are to be delivered with the same introducer, then the multiple supports may be preloaded into the introducer for sterility. If more than one support is included in a kit, the supports may be of different shapes, sizes, lengths, or materials. If the kits contain more than one support to be implanted into a single eye, the supports may be connected together.

The kits may comprise one or more active agents, such as a pharmaceutical agent. The active agent(s) may be included as an integral part of the support, or may be supplied in kits for application to the support or to the eye during or after implantation. Examples of active agents that may be supplied as part of the kits include prostaglandins, prostaglandin analogs, beta blockers, alpha-2 agonists, calcium channel blockers, carbonic anhydrase inhibitors, growth factors, such as tissue growth factors or vascular endothelial growth factors, antimetabolites, chemotherapeutic agents such as mitomycin-C, 5-fluorouracil, steroids, antagonists of growth factors, such as antagonists of vascular endothelial growth factor, and combinations thereof.

The kits may contain a fixation device for attaching a support to tissue. Such a fixation device may include sutures, hooks, barbs, clips, adhesives, and combinations thereof. In addition, the kits may include a system for visually enhancing the support to facilitate viewing, positioning, and monitoring of a support. A system for visually enhancing the support may include a light source, a transmission or absorption filter, a mirror, a composition comprising a chromophore capable of fluorescing or phosphorescing that can be applied to the support, or any combination thereof. Chromophores may assist a clinician in verifying the position of the support postoperatively using a gonioscope, for example. The light source may be capable of exciting a chromophore contained within or on the support such that the chromophore emits fluorescence or phosphorescence. The emission is preferably within the wavelength range of about 300 nm to about 800 nm. A suitable light source for such a system may comprise a laser, a light emitting diode, or a lamp. In some instances, transmission or absorption filters may be used to further select the wavelength range of the excitation source or view or detect emission from chromophores. One or more minors may be used to direct a light source or emitted light, or to view the support.

Methods of Use

Methods for reducing intraocular pressure are also provided. In general, the methods may comprise inserting a support circumferentially within at least a portion of Schlemm's canal, such that the support restores or maintains at least partial patency of at least a portion of the canal. The support may or may not occupy at least a portion of a central core of Schlemm's canal. In some variations, the support may not substantially interfere with transmural or transluminal flow across Schlemm's canal, and/or with longitudinal flow along the canal.

The methods may comprise inserting a support circumferentially into Schlemm's canal using an introducer and/or a positioning device. The introducer may include a cannula and a tubular or hollow pusher rod or an advancing wire. The cannula may, for example, comprise a distal exit port having a cutting, beveled and/or tapered tip that allows the cannula to cut through the trabecular meshwork (e.g., if ab interno) and/or to be introduced into Schlemm's canal (e.g., for ab interno and ab externo approaches). The support may be installed in the lumen of the cannula at its distal end and the pusher rod may be inserted into the lumen of the cannula at its proximal end and extended distally to push the support into position in the canal. In some instances, the cannula and/or the pusher rod may be flexible and small enough in diameter to at least partially extend circumferentially around the canal. In some variations of the methods, a positioning device may be used in addition to an introducer. The positioning device may comprise a second rod, a gripper, a hook, a clamp, or the like. Control of delivery or advancement into Schlemm's canal may be via a more proximal control that may be operable from outside the eye.

In certain variations, the methods may include illuminating a support with a light source to cause the support to fluoresce or phosphoresce, thus aiding the visual appearance of the support. The illumination of the support may occur during and/or after implantation to inspect the support (e.g., to monitor its position, condition and/or performance).

In some instances, the methods may also comprise dilating Schlemm's canal prior to and/or during insertion of the support. Dilation of the canal may be accomplished by injecting fluid into the canal. For example, a high viscosity fluid such as sodium hyaluronate, or another viscoelastic substance or other dilating fluid known in the art, may be used to dilate the canal. As an example, in some variations, a fluid (e.g., a viscoelastic fluid) may be used first to dilate Schlemm's canal, and then the support may be delivered into the canal. As another example, in certain variations, a support may be packaged in a fluid (e.g., a viscoelastic fluid), and may be delivered (e.g., injected) into Schlemm's canal concurrently with the fluid. As an additional example, in some variations, a support may be delivered into Schlemm's canal, and a fluid (e.g., a viscoelastic fluid) may be delivered (e.g., injected) into the canal after delivery of the support. In these cases the fluid may, for example, help to push the support along within Schlemm's canal.

The methods may include implanting more than one support into an eye. In some variations, the methods may include implanting two or more supports circumferentially adjacent to each other within the canal. In certain variations, the methods may include implanting supports circumferentially opposed to each other within the canal (e.g., two supports centered about 180° apart around the circumference of Schlemm's canal). Some variations of the methods may comprise connecting together multiple supports in a single eye.

In some variations, the methods may include anchoring the support to tissue surrounding Schlemm's canal. Anchoring the support to tissue may be accomplished in a variety of ways (e.g., by suturing, application of adhesives, installation of hooks, clips, or the like, or combinations thereof). In certain variations, the methods may comprise selecting the size of the support such that the support fits securely into the canal by a friction fit. Examples of arcuate supports that may be implanted with a friction fit are illustrated in FIGS. 11A-11C.

The methods described here may also include altering the support using electromagnetic radiation. For example, a support may include regions capable of preferentially absorbing a certain wavelength range. When electromagnetic radiation of the appropriate wavelength range with sufficient energy is incident upon the support, material in the preferentially absorbing regions may melt or ablate, resulting in perforations or indentations in the support at those regions. For example, a pulsed titanium sapphire laser emitting at about 750 nm to about 800 nm incident on gold may cause the gold to melt or ablate. The alteration of a support using electromagnetic radiation may occur before or after implantation of the support. For example, fenestrations may be created or enlarged in a support after the support has remained in an eye for a period of time to enhance drainage.

Delivery of the supports described here may comprise an internal approach (ab interno) or an external approach (ab externo), as appropriate.

In some variations, an external approach may comprise achieving access to Schlemm's canal by cutting down to it from the sclera until it is directly visualized. The support may then be implanted. For example, the conjunctiva may be incised and a scleral flap may be created. Schlemm's canal may be exposed and may be directly visualized (e.g., under a microscope). The same delivery system as described for the internal approach may be used; however, the external approach may not involve cutting through the trabecular meshwork.

In certain variations, an internal approach may comprise achieving access to Schlemm's canal by creating a full-thickness incision in the cornea, anterior most sclera, or corneo-scleral junction (i.e. the corneal limbus). Under endoscopic visualization, a combination of gonioscopic and microscopic visualization, or just microscopic visualization, a cutting blade or needle and a support or a delivery device containing a support may be passed through the anterior chamber to the trabecular meshwork. The trabecular meshwork may then be pierced or incised to allow eventual entry into the underlying lumen of Schlemm's canal (e.g., by cutting a hole with a needle or blade, creating a hole with a laser, creating a hole with electrical current (i.e., electrocautery), creating a hole with the tip of the support and/or delivery device, and/or using a delivery cannula that has a cutting surface on its distal tip). As an example, a trocar that has a cutting surface may be used to perforate the trabecular meshwork, and a guard or stop may be used to prevent over-insertion. As another example, a cannula for implant delivery could likewise have a cutting, tapered and/or beveled tip for piercing the trabecular meshwork prior to advancement of the cannula partially or completely within the canal for support implantation. In cases in which a cannula is used, the cannula may be inserted into Schlemm's canal by any appropriate amount, from 0 millimeters to the entire length of the support, or more. The support may then be implanted. In cases in which lasers are employed, any appropriate laser or lasers may be used, including but not limited to a 308 nm Xenon Chloride excimer laser (e.g., delivered through a fiber optic).

Upon achieving access to the canal, either by direct visualization (i.e., using an external approach) or by piercing the trabecular meshwork (i.e., using an internal approach), implantation of the support may proceed. In certain variations, a support may be delivered in a relatively straight form that provides for relatively easy delivery. The support may later assume a different shape (e.g., dictated by memory and temperature). Implantation may be achieved using any of a variety of different approaches, or combinations thereof. In some variations, a support may be directly pushed into Schlemm's canal using a forceps or specialized instrument to grasp the support while not damaging it. In certain variations, and as noted previously, a support may be contained in a cannula that may be partially or completely advanced into Schlemm's canal.

Support delivery may be achieved, for example, using a manual control or a proximal delivery control in cases in which a cannula is used, that is external to the eye and that is operated by the surgeon and/or surgical staff. The control may be in the form of, for example, a handheld actuator mechanism. When a support is delivered out of a cannula, in some variations, just the tip of the cannula is positioned in Schlemm's canal and the support is pushed out. In certain variations, a push-pull mechanism may be used to deliver a support from a cannula, whereby the cannula is pulled upon and the support is simultaneously pushed upon. Other non-limiting examples of tools that may be used to deliver a support include syringes or syringes in combination with pushing wires. A cannula and/or a delivered support may extend from 0° to 360° around the canal.

The support may then be delivered by a pusher wire that pushes the support into its resting place in the canal, and the cannula may be slowly withdrawn while the pusher wire holds the support in place, ultimately leaving the support unsheathed and resting in the canal. Alternatively or additionally, fluid pressure may be used to force the support out of the cannula. The support may, for example, have a blocking element at its end to capture the directional pressure of the fluid (e.g., like a sail). In some variations, a pusher wire may have a screw mechanism allowing the support to be pushed in using a screwing motion rather than a simple push (e.g., providing for relatively controlled delivery). In certain variations, a disengagement mechanism may be used to release a support from a cannula. In some variations, a cannula or support may have a tapered tip for facilitating delivery, dilating narrowed areas of Schlemm's canal, and piercing through septae that block the canal.

In certain variations of delivery methods in which a cannula is used, a viscoelastic or other type of solution or drug or dye (e.g., a fluorescent dye) may be injected from the cannula.

Cannulas used for delivery of supports described herein may in some cases have tips that are blunt, sharpened, tapered, or beveled, or that have a cutting surface or a partially cutting surface or a combination of these and/or any other suitable features (e.g., to facilitate insertion into Schlemm's canal). Cannulas may be made out of metals (e.g., titanium), metal alloys (e.g., stainless steel or nickel-titanium alloys such as Nitinol) and/or polymers (e.g., transparent polycarbonate or polypropylene, or any other suitable polymers). In certain variations, a cannula may comprise one or more elements (e.g., at the distal end of the cannula) configured to prevent excessive entry of the cannula. In other words, the element or elements would allow the cannula to perforate the trabecular meshwork, but not to go beyond and cause damage to Schlemm's canal (basically allowing only entry into Schlemm's canal). For example, a cannula with a beveled tip may be used to pierce through the trabecular meshwork, such that the bevel is completely within Schlemm's canal. However, a peg, pin or bump (or other element, such as a widening or tapering feature) on the cannula may prevent further insertion. In some cases, a cannula may comprise markings to denote the extent of insertion. In some variations, an element or elements may allow the cannula to be advanced further, but to a controlled length of insertion (e.g., that is equivalent to the length of the support). In certain variations, a cannula may be dyed or colored and/or may be fluorescent (e.g., to enhance visibility). Cannulas may have any appropriate dimensions, and in some cases may have a length of up to 2 or 3 inches, an external diameter of 10 microns to 800 microns, and/or an internal diameter of 20 microns to 780 microns. In some variations, a cannula may be pre-curved. Cannulas for use with the methods described here may also be flexible.

In some cases during delivery, a support may be threaded over a guidewire that may fit into a lumen of the support or through periodic fenestrations along the length of the support. The guidewire and support may be inserted together at the same time, or the guidewire may be inserted first, followed by running the support over it. Additional non-limiting examples of tools and techniques that may be used to deliver a support include forceps and pullthrough techniques.

In some variations of methods, elements or features of a support that are configured to contact an interior surface of Schlemm's canal may be spaced in such a way as to reduce the likelihood of one or more of the elements or features blocking one or more of the collector channels of the canal. In certain variations, a support may be rotated or otherwise moved during and/or after delivery into Schlemm's canal, to limit or prevent collector channel blockage. Delivery accuracy and placement may be monitored using one or more imaging techniques, such as ultrasonography, radiographic techniques, X-ray fluoroscopy, and/or other high-resolution imaging techniques (e.g., high-resolution ultrasonography), as well as interventional techniques (e.g., employing contrast material or dye or fluorescent material or dye).

In certain variations, a support may be at least partially coated with (e.g., embedded in) one or more biocompatible, dissolvable, or bioabsorbable materials which may provide several advantages. Possible advantages may include making the delivery of the support less traumatic to the eye (e.g., providing a silicone coating to minimize any trauma that may be associated with insertion of the support), protecting a delicate support structure during implantation and providing more delivery column strength for pushing and/or insertion, and/or enhancing visibility of the support during delivery (e.g., the material may be colored, may comprise chromophores, or may be fluorescent). In some variations, the coating may serve as a carrier or depot for one or more substances. In certain variations, the coating material(s) may contain a therapeutic agent (e.g., a drug), such as an antiglaucoma medication (e.g., to reduce pressure), an antifibrotic agent and/or antimetabolite (e.g., to reduce scarring), or an anti-inflammatory agent (e.g., to reduce inflammation and/or pain). Examples of anti-inflammatory agents include heparin, mitomycin, 5-fluorouracil, anti-metabolites and non-steroidal anti-inflammatories. Examples of anti-glaucoma medications include prostaglandins, beta-blockers, alpha adrenergic agonists, carbonic anhydrase inhibitors, and miotics. The material(s) may absorb on their own or in an accelerated manner (e.g., using an outside energy source). In certain variations, a support tip or coating may comprise one or more bioabsorbable materials containing a drug that may be absorbed within a certain time period (e.g., hours, days, weeks, or months) following insertion.

In cases in which multiple supports are delivered into Schlemm's canal, some or all of the supports may be delivered in the same procedure, or supports may be delivered in two or more different procedures. For example, one or more supports may be delivered to an eye using a first procedure, and one or more supports may be delivered to the same eye using a second procedure that occurs at a later date (e.g., 1 day, 1 week, 1 month, 1 year, 2 years, 3 years, 4 years, 5 years, etc. later).

In some cases, one or more supports described herein may be implanted in Schlemm's canal, and may be followed by one or more other treatments (e.g., surgery, medicine) at a later date. It is believed that use of supports described herein may advantageously improve the efficacy of later procedures, such as later excimer laser trabeculostomy, laser trabeculoplasty and other surgeries, and may also improve the efficacy of medications that are used at a later date.

Methods of Making

Any appropriate methods may be used to make the devices described herein. For example, in some variations, a support may be formed by twisting a substrate, such as a ribbon member. The substrate may, for example, be twisted around a mandrel. In some cases, one end of the substrate may be held by a tool (e.g., a vise), while another end of the substrate is held or grasped by another tool (e.g., a similar vise) that rotates to twist the substrate. Other non-limiting examples of methods that may be used to form the devices described herein include laser etching, lithography, and injection molding. As an example, in some variations, a support may be created using a lithography metal deposition process. As another example, in certain variations, a support may be formed by injecting a polymer into a prefabricated mold.

Devices, methods and kits for use with Schlemm's canal are also described, for example, in U.S. patent application Ser. No. 11/475,523 (published as US 2007/0298068 A1), which is incorporated herein by reference in its entirety.

While the inventive devices, methods and kits have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims.

As an example, it is envisioned that the devices, methods and kits may be applied to nonhuman eyes to reduce intraocular pressure (e.g., in dogs, cats, primates, or horses).

As another example, devices described herein may be positioned entirely within Schlemm's canal or only partially within Schlemm's canal. In some variations, a device may be positioned so that it extends or protrudes into the anterior chamber of the eye. For example, in certain variations, a device may have a configuration like support 1400 of FIGS. 14A and 14B, but may further include a bent or curved region that allows the support to protrude into the anterior chamber of the eye during use. Devices described herein may include any appropriate number of bent or curved regions, which may be used to position the devices in any suitable manner.

In some variations, devices comprising supports similar or identical to those described previously may be used to provide a bypass function (e.g., in addition to maintaining or restoring transmural, transluminal and/or longitudinal flow of aqueous humor). In some such variations, the operator (e.g., surgeon) may not fully insert the support, and may thereby allow a proximal portion of the support to be positioned in the anterior chamber (thereby serving as a bypass). In certain variations, after delivery of a support, the distal end of the support (which is inside Schlemm's canal) may be engaged with a hook or grasping device (tearing a small part of the overlying trabecular meshwork) and bent inward to the anterior chamber to provide the support with a bypass function. The proximal end of the support may not have been fully inserted into Schlemm's canal and may thereby already be serving a bypass function. Alternatively, the proximal end may have been fully inserted. In some variations, a support may comprise a proximal end and/or distal end that is configured to protrude from Schlemm's canal at an angle between 0° and 180° (e.g., 90°), across the trabecular meshwork, and into the anterior chamber. For example, the support may have an "L" shape. The proximal end of the support may serve a bypass function and may, for example, measure between about 10 microns and about 3 millimeters. The proximal end may have the same shape or configuration as the body of the support, or may have a different shape or configuration. In some cases, the proximal end may be in the form of a coil, or may be tubular or partially tubular. In variations in which the support has an "L" shape or a similar shape, the support may be packaged and/or delivered with one or more of the cannulas or other delivery devices described herein (e.g., bending upon exiting the cannula or delivery device, as a result of shape memory), or a cannula or other delivery device may be slit to accommodate the proximal bypass portion of the support.

As an additional example, in some cases it may be desirable to stretch Schlemm's canal. In such cases, a device may be configured (e.g., sized and shaped) to achieve such stretching when placed within the canal.

What is claimed is:

1. A device for reducing intraocular pressure comprising:
a twisted ribbon member implantable circumferentially within at least a portion of Schlemm's canal and configured to restore or maintain at least partial patency of at least a portion of Schlemm's canal,
wherein the twisted ribbon member comprises a double helix having a length, a first elongated edge, a second elongated edge, and a central longitudinal axis, the first and second elongated edges of the double helix being twisted along and about the central longitudinal axis, and comprising a plurality of struts extending therebetween in a direction substantially normal to the central longitudinal axis, and wherein the plurality of struts define a plurality of fenestrations spaced along at least a portion of the length of the twisted ribbon member.

2. The device of claim 1, wherein the first and second elongated edges are configured to contact an interior surface of Schlemm's canal when the device is implanted in Schlemm's canal.

3. The device of claim 2, wherein the first and second elongated edges are configured to continuously contact the interior surface of Schlemm's canal when the device is implanted in Schlemm's canal.

4. The device of claim 1, wherein the device does not substantially interfere with transmural flow across Schlemm's canal when the device is implanted in Schlemm's canal.

5. The device of claim 1, wherein the twisted ribbon member comprises a shape memory alloy.

6. The device of claim 5, wherein the shape memory alloy comprises a nickel-titanium alloy.

7. The device of claim 1, wherein the twisted ribbon member comprises a metal alloy.

8. The device of claim 7, wherein the metal alloy comprises stainless steel.

9. The device of claim 1, wherein the twisted ribbon member comprises a metal.

10. The device of claim 9, wherein the metal comprises titanium.

\* \* \* \* \*